United States Patent

Commerçon et al.

[11] Patent Number: 5,936,097
[45] Date of Patent: Aug. 10, 1999

[54] 4,9-ETHANO-BENZO(F)ISOINDOLE DERIVATIVES AS FARNESYL TRANSFERASE INHIBITORS

[75] Inventors: Alain Commerçon, Vitry-Sur-Seine; Alain Le Brun, Vigneux; Patrick Mailliet, Fontenay Sous Bois; Jean-François Peyronel, Palaiseau; Fabienne Sounigo-Thompson, Paris; Alain Truchon, Lyons; Martine Zucco, Thiais, all of France

[73] Assignee: Rhone-Poulenc Rorer, S.A., Antony, France

[21] Appl. No.: 08/981,840

[22] PCT Filed: Jul. 8, 1996

[86] PCT No.: PCT/FR96/01062

§ 371 Date: Jul. 23, 1998

§ 102(e) Date: Jul. 23, 1998

[87] PCT Pub. No.: WO97/03050

PCT Pub. Date: Jan. 30, 1997

[30] Foreign Application Priority Data

Jul. 10, 1995 [FR] France ............... 95/08296

[51] Int. Cl.⁶ .......... C07D 209/62; C07D 209/12; C07D 277/22; C07D 307/36
[52] U.S. Cl. .......... 548/425; 548/491; 548/494; 548/426; 548/146; 548/335.1; 548/469; 548/377.1; 549/506; 546/22; 546/276.7; 560/24; 585/400; 514/80; 514/410
[58] Field of Search ............... 548/491, 494, 548/425, 426, 146, 335.1, 469, 377.1; 549/506; 546/348, 22, 276.7; 560/24; 585/400; 514/80, 410

[56] References Cited

U.S. PATENT DOCUMENTS 4,465,688  8/1984  Schroot et al. ............ 424/274

FOREIGN PATENT DOCUMENTS

WO/9512612  5/1995  WIPO .

*Primary Examiner*—Johann Richter
*Assistant Examiner*—Dominic Keating
*Attorney, Agent, or Firm*—Finnegan, Henderson, Farabow, Garrett & Dunner, L.L.P.

[57] ABSTRACT

Novel products of formula (I):

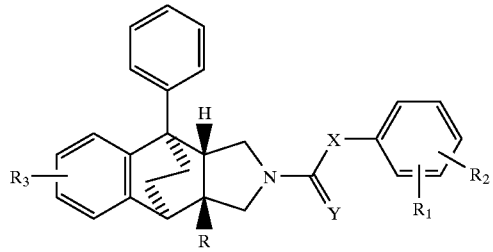

preparation thereof and pharmaceutical compositions containing said products are disclosed. In formula (I), R is a group of formula —$(CH_2)_m$—$X_1$—$(CH_2)_n$—Z, where $X_1$ is a simple bond or O or S, n is 0 or 1 and n is 0, 1 or 2, the $CH_2$ groups being optionally substituted by carboxy, alkoxycarbonyl, carbamoyl, alkylcarbamoyl, dialkylcarbamoyl, amino, alkylamino or dialkylamino, and Z is carboxy, $COOR_4$, where $R_4$ is alkyl, or $CON(R_5)(R_6)$, where $R_5$ hydrogen or alkyl and $R_6$ is hydrogen or optionally substituted alkyl, or else $R_5$ is hydrogen or alkyl and $R_6$ is hydroxy, optionally substituted alkoxy or amino, or $PO(OR_7)_2$, where $R_7$ is hydrogen or alkyl; or a group —NH—CO—T where T is hydrogen or optionally substituted alkyl; or else a group (a); $R_1$ and $R_2$ are hydrogen or halogen or optionally substituted alkyloxy or alkyl, or else $R_1$ and $R_2$ in the ortho positions form a heterocyclic ring containing 1 or 2 optionally substituted hereoatoms, or $R_1$ is hydrogen or halogen or optionally substituted alkyloxy or alkyl, and $R_2$ is thioalkyl; $R_3$ is hydrogen or halogen or alkyl alkenyl, alkyloxy, alkylthio, carboxy or alkyloxycarbonyl; X is O or S or —NH—, —CO—,methylene, ethylene, alkylidene or 1,1-cycloalkyl; and Y is O or S. The novel products of formula (I) are farnesyl transferase inhibitors having remarkable antitumoral and antineoplastic properties.

27 Claims, No Drawings

4,9-ETHANO-BENZO(F)ISOINDOLE DERIVATIVES AS FARNESYL TRANSFERASE INHIBITORS

This application is a 371 of PCT/FR96/01062, filed Jul. 08, 1996.

The present invention relates to new products of general formula:

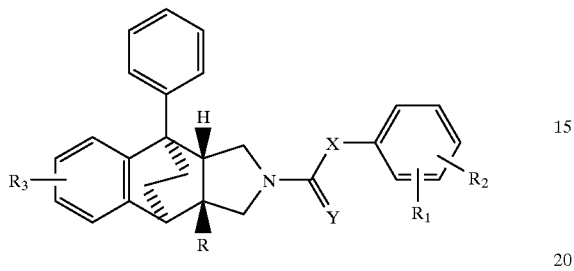

to their preparation and to the pharmaceutical compositions which contain them.

In the general formula (I), R represents:

a radical of general formula —$(CH_2)_m$—$X_1$—$(CH_2)_n$Z in which $X_1$ represents a single bond or an oxygen or sulphur atom, m represents an integer equal to 0 or 1 and n represents an integer equal to 0, 1 or 2, it being possible for the methylene radicals to be substituted by a carboxyl radical, an alkoxycarbonyl radical in which the alkyl part contains 1 to 4 carbon atoms, a carbamoyl radical, an alkylcarbamoyl radical in which the alkyl part contains 1 to 4 carbon atoms, a dialkylcarbamoyl radical in which each alkyl part contains 1 to 4 carbon atoms, an amino radical, an alkylamino radical containing 1 to 4 carbon atoms or a dialkylamino radical in which each alkyl part contains 1 to 4 carbon atoms and z represents a carboxyl radical, a $COOR_4$ radical, in which $R_4$ represents a straight or branched alkyl radical containing 1 to 3 carbon atoms, or a $CON(R_5)$ $(R_6)$ radical in which $R_5$ represents a hydrogen atom or a straight or branched alkyl radical containing 1 to 6 carbon atoms and $R_6$ represents a hydrogen atom or a straight or branched alkyl radical containing 1 to 6 carbon atoms optionally substituted by an amino, alkylamino containing 1 to 4 carbon atoms, dialkylamino in which each alkyl part contains 1 to 4 carbon atoms, hydroxyl, alkoxy containing 1 to 4 carbon atoms, mercapto, alkylthio containing 1 to 4 carbon atoms, alkyloxycarbonyl in which the alkyl part contains 1 to 4 carbon atoms, carboxyl, cyano, phenyl optionally substituted by one or a number of identical or different atoms or radicals chosen from halogen atoms and alkyl radicals containing 1 to 4 carbon atoms, alkoxy radicals containing 1 to 4 carbon atoms, dialkylamino radicals in which each alkyl part contains 1 to 4 carbon atoms, trifluoromethyl radicals or cyano radicals, 1- or 2-naphthyl, 2- or 3-furyl, 2- or 3-thienyl, 4- or 5-imidazolyl, 2-, 4- or 5-thiazolyl, 2-, 4- or 5-thiazolidinyl or 2-, 3- or 4-pyridyl radical or an indanyl or thiochromanyl radical or else $R_5$ represents a hydrogen atom or a straight or branched alkyl radical containing 1 to 6 carbon atoms and $R_6$ represents a hydroxyl radical, an amino radical or an alkyloxy radical containing 1 to 6 straight- or branched-chain carbon atoms optionally substituted by a phenyl radical, or a $PO(OR_7)_2$ radical in which $R_7$ represents a hydrogen atom or a straight or branched alkyl radical containing 1 to 6 carbon atoms, or an —NH—CO—T radical in which T represents a hydrogen atom or a straight or branched alkyl radical containing 1 to 6 carbon atoms optionally substituted by an amino, carboxyl, alkyloxycarbonyl, in which the alkyl part contains 1 to 4 carbon atoms, hydroxyl, alkyloxy containing 1 to 4 carbon atoms, mercapto or alkylthio, containing 1 to 4 carbon atoms, radical, or else a

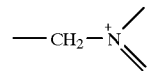

radical in which

preferably represents a pyridinium radical, $R_1$ and $R_2$, which are identical or different, represent a hydrogen or halogen atom or an alkyl radical containing 1 to 4 carbon atoms, an alkyloxy radical containing 1 to 4 carbon atoms optionally substituted by a dialkylamino radical in which each alkyl part contains 1 to 4 carbon atoms or forms, with the nitrogen atom, a saturated heterocycle containing 5 or 6 carbon atoms, an alkylthio radical containing 1 to 4 carbon atoms or an alkyloxycarbonyl radical in which the alkyl part contains 1 to 4 carbon atoms, or else $R_1$ and $R_2$, situated in the ortho position with respect to one another, form a saturated or unsaturated heterocycle containing 1 or 2 heteroatoms chosen from nitrogen and oxygen, optionally substituted by a halogen atom or by an alkyl radical containing 1 to 4 carbon atoms or an alkyloxy radical containing 1 to 4 carbon atoms, or else $R_1$ represents a hydrogen or halogen atom or an alkyl radical containing 1 to 4 carbon atoms, an alkyloxy radical containing 1 to 4 carbon atoms optionally substituted by a dialkylamino radical in which each alkyl part contains 1 to 4 carbon atoms, an alkylthio radical containing 1 to 4 carbon atoms or an alkyloycarbonyl radical in which the alkyl part contains 1 to 4 carbon atoms and $R_2$ represents a thioalkyl radical containing 1 to 4 carbon atoms, it being understood that, in this case, the product of general formula (I) exists in the form of a product twinned via a disulphide bridge, $R_3$ represents a hydrogen or halogen (iodine) atom or an alkyl radical containing 1 to 4 carbon atoms, an alkenyl radical containing 2 to 4 carbon atoms, an alkyloxy radical containing 1 to 4 carbon atoms or an alkylthio radical containing 1 to 4 carbon atoms, a carboxyl radical or an alkyloxycarbonyl radical in which the alkyl part contains 1 to 4 carbon atoms, X represents an oxygen or sulphur atom or an —NH—, —CO—, methylene, ethylene, alkylidene, such as vinylidene, or 1,1-cycloalkyl group containing 3 to 6 carbon atoms, and Y represents an oxygen or sulphur atom, in the racemic form, and the optical isomers of the product of general formula (I).

According to the invention, the new products of general formula (I) in which R, $R_1$, $R_2$ and $R_3$ are defined as above, Y represents an oxygen or sulphur atom and X represents a —CO—, methylene, ethylene, alkylidene or 1,1-cycloalkyl group can be obtained by reaction of an acid of general formula:

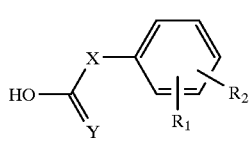

(II)

in which $R_1$, $R_2$ and X are defined as above and Y represents an oxygen or sulphur atom, of its methyl ester or of a derivative of this acid, such as a halide or the anhydride, with a product of general formula:

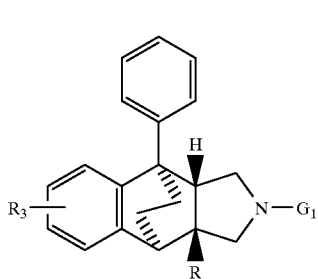

(III)

in which R and $R_3$ are defined as above and $G_1$ represents a hydrogen atom (which can be obtained from a product of general formula (III) in which $G_1$ represents a protective group for an amino functional group, such as a benzyl, benzyloxycarbonyl or tert-butoxycarbonyl radical, by hydrogenolysis in the presence of a catalyst such as palladium-on-charcoal, when $G_1$ represents a benzyl or benzyloxycarbonyl radical, or by hydrolysis in acid medium, when $G_1$ represents a tert-butoxycarbonyl or benzyloxycarbonyl radical), optionally followed, when R represents or contains a —$COOR_4$ or —$PO(OR_7)_2$ radical in which $R_4$ and $R_7$ represent an alkyl radical, by the saponification of the product obtained, to obtain a product of general formula (I) in which R represents or contains a carboxyl radical, or by the conversion, by means of a nucleophilic agent, of the product obtained, to obtain a product of general formula (I) in which R represents or contains a —$PO_3H_2$ radical.

Generally, the reaction of the product of general formula (II) in the acid form with the product of general formula (III) is carried out in an organic solvent, such as a halogenated aliphatic hydrocarbon, such as dichloromethane, in the presence of a coupling and/or activating agent, such as 1-ethyl-3-[3-(dimethylamino)propyl]carbodiimide hydrochloride, hydroxybenzotriazole, 1,3-dicyclohexylcarbodiimide or benzotriazol-1-yloxytris(dimethylamino)phosphonium hexafluorophosphate, at a temperature of between 0 and 50° C.

Generally, the reaction of the product of general formula (II) in the form of the methyl ester with a product of general formula (III) is carried out in an organic solvent, such as dioxane or a halogenated aliphatic hydrocarbon, such as dichloromethane, at a temperature of between 0° C. and the reflux temperature of the reaction mixture.

Generally, the reaction of the product of general formula (II) in the halide form with the product of general formula (III) is carried out in an organic solvent, such as a halogenated aliphatic hydrocarbon, such as dichloromethane, in the presence of a base (tertiary aliphatic amine), at a temperature of between 0 and 50° C.

Generally, the reaction of the product of general formula (II) in the anhydride form with the product of general formula (III) is carried out in an organic solvent, such as a halogenated aliphatic hydrocarbon, such as dichloromethane, in the presence of a base (tertiary aliphatic amine, pyridine or 4-dimethylaminopyridine), at a temperature of between 0 and 50° C.

Generally, the saponification of a product of general formula (I) in which R represents or contains an ester of general formula —$COOR_4$ to a product of general formula (I) in which R represents or contains a carboxyl radical is carried out by means of an inorganic base, such as sodium hydroxide or potassium hydroxide or sodium carbonate, in an organic solvent, such as an alcohol, for example methanol or ethanol.

Generally, the conversion of a product of general formula (I) in which R represents or contains a $PO(OR_7)_2$ radical to a product of general formula (I) in which R represents or contains a $PO_3H_2$ radical is carried out by the action of a nucleophilic agent, such as a trialkylsilyl (trimethylsilyl) halide (iodide) or of a sodium or lithium halide (sodium iodide), in the presence of a trialkylhalosilane (trimethylchlorosilane or trimethylbromosilane), in a polar solvent (carbon tetrachloride or acetonitrile), at a temperature of between 0 and 50° C., or by heating with an alkali metal halide (sodium iodide), followed by hydrolysis.

According to the invention, the new products of general formula (I) in which Y represents an oxygen or sulphur atom and X represents an oxygen atom can be obtained by reaction of a haloformate or of a halothioformate of general formula:

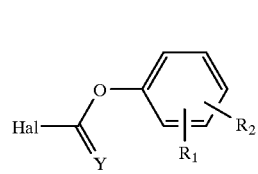

(IV)

in which Y represents an oxygen or sulphur atom, $R_1$ and $R_2$ are defined as above and Hal represents a halogen atom, with a product of general formula (III), and then, optionally, when R represents or contains a —$COOR_4$ or —$PO(OR_7)_2$ radical, the product obtained [lacuna] saponified, to obtain a product of general formula (I) in which R represents or contains a carboxyl radical, or the product obtained [lacuna] converted, by means of a nucleophilic agent, to a product of general formula (I) in which R represents or contains a —$PO_3H_2$ radical.

Generally, the reaction of the halide of general formula (IV) with the product of general formula (III) is carried out in organic or aqueous/organic medium, such as a dioxane/water mixture, in the presence of an inorganic base (sodium hydroxide) or organic base (triethylamine), at a temperature of between 0 and 50° C.

According to the invention, the new products of general formula (I) in which Y represents an oxygen or sulphur atom and X represents an NH group can be obtained by reaction of an isocyanate or of an isothiocyanate of general formula:

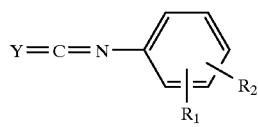

(V)

in which Y represents an oxygen or sulphur atom and $R_1$ and $R_2$ are defined as above, with a product of general formula (III), optionally followed, when R represents or contains a —COOR$_4$ or —PO(OR$_7$)$_2$ radical in which $R_4$ or $R_7$ represent an alkyl radical, by the saponification of the product obtained, to obtain a product of general formula (I) in which R represents or contains a carboxyl radical, or by the conversion, by means of a nucleophilic agent, of the product obtained, to obtain a product of general formula (I) in which R represents or contains a —PO$_3$H$_2$ radical.

Generally, the reaction of the product of general formula (V) with the product of general formula (III) is carried out in an inert organic solvent, such as tetrahydrofuran or toluene, in the presence of a coupling agent, such as 4-dimethylaminopyridine or 4-pyrrolidinopyridine, at a temperature of between 0 and 50° C.

Optional replacement of the —COOR$_4$ and PO(OR$_7$)$_2$ radicals respectively by carboxyl and PO$_3$H$_2$ radicals is carried out under the conditions described above.

According to the invention, the new products of general formula (I) in which $R_1$, $R_2$ and $R_3$ are defined as above, X represents an oxygen or sulphur atom or an —NH—, —CO—, methylene, ethylene, alkylidene or 1,1-cycloalkyl group and Y represents an oxygen or sulphur atom and R represents a radical of general formula —(CH$_2$)$_m$—X$_1$—(CH$_2$)$_n$—Z in which $X_1$, m and n are defined as above and Z represents a —COOR$_4$ radical in which $R_4$ represents a straight or branched alkyl radical containing 1 to 3 carbon atoms can be obtained by esterification of a product of general formula (I) in which $R_1$, $R_2$, $R_3$, X, Y, $X_1$, m and n are defined as above and Z represents a carboxyl radical.

Generally, the esterification is carried out by means of an alcohol of general formula R$_4$—OH in which $R_4$ is defined as above, in acid medium, or by means of an alkyl halide of general formula R$_4$—Hal in which Hal represents a halogen (iodine) atom, in alkaline medium (alkali metal or alkaline-earth metal carbonate, such as caesium carbonate), in an organic solvent, such as dimethylformamide, at a temperature of between 0 and 50° C.

According to the invention, the new products of general formula (I) in which $R_1$, $R_2$ and $R_3$ are defined as above, X represents an oxygen or sulphur atom or an —NH—, —CO—, methylene, ethylene, alkylidene or 1,1-cycloalkyl group and Y represents an oxygen or sulphur atom and R represents a radical of general formula —(CH$_2$)$_m$—X$_1$—(CH$_2$)$_n$—Z in which $X_1$, m and n are defined as above and Z represents a CON(R$_5$) (R$_6$) radical in which which $R_5$ and $R_6$, which are identical or different, represent a hydrogen atom or a straight or branched alkyl radical containing 1 to 6 carbon atoms and $R_6$ represents a hydrogen atom or a straight or branched alkyl radical containing 1 to 6 carbon atoms optionally substituted by an amino, alkylamino containing 1 to 4 carbon atoms, dialkylamino in which each alkyl part contains 1 to 4 crabon atoms, alkoxy containing 1 to 4 crabon atoms, alkylthio containing 1 to 4 carbon atoms, alkyloxycarbonyl in which the alkyl part contains 1 to 4 carbon atoms, carboxyl, cyano, phenyl optionally substituted by one or a number of identical or different radicals chosen from alkoxy radicals containing 1 to 4 carbon atoms or trifluoromethyl radicals, 1- or 2-naphthyl, 2- or 5 3-furyl, 2- or 3-thienyl, 4- or 5-imidazolyl, 4- or 5-thiazolyl or 2-, 3- or 4-pyridyl radical or an indanyl or chromanyl radical or else $R_5$ represents a hydrogen atom or a straight or branched alkyl radical containing 1 to 6 carbon atoms and $R_6$ represents a 10 hydroxyl radical, an amino radical or an alkyloxy radical containing 1 to 6 straight- or branched-chain carbon atoms optionally substituted by a phenyl radical can be obtained by reaction of a product of general formula HN(R$_5$) (R$_6$), in which $R_5$ and $R_6$ are defined as is above, with a product of general formula (I) in which $R_1$, $R_2$, $R_3$, X, Y, $X_1$, m and n are defined as above and Z represents a carboxyl radical.

When $R_5$ and $R_6$ each represent a hydrogen atom, it is particularly advantageous to react ammonia, 20 optionally in solution in an organic solvent, such as an alcohol (ethanol), in the presence of a coupling agent, such as N,N'-carbonyldiimidazole, 1,1-dicyclohexylcarbodiimide, 1-ethyl-3-[3-(dimethylamino)propyl]carbodiimide hydrochoride, 25 hydroxybenzotriazole or benzotriazol-1-yloxytris-(dimethylamino)phosphonium hexafluorophosphate, at a temperature of between 0 and 50° C.

When $R_5$ and $R_6$ do not each represent a hydrogen atom, it is particularly advantageous to react the amine of general formula HN(R$_5$) (R$_6$), in the presence of a coupling agent and/or of an activating agent, such as 1-ethyl-3-[3-(dimethylamino)propyl]carbodiimide hydrochloride, hydroxybenzotriazole, 1,1-dicyclohexyl-carbodiimide or benzotriazol-1-yloxytris-(dimethylamino)phosphonium hexafluorophosphate, in an organic solvent, such as a halogenated aliphatic hydrocarbon (dichloromethane), at a temperature of between 0 and 50° C.

When at least one of the $R_5$ and $R_6$ symbols is substituted by an amino radical, it is particularly advantageous to protect it by a protective group, such as a tert-butoxycarbonyl, benzyloxycarbonyl or benzyl radical, prior to the coupling of the amine of general formula HN(R$_5$) (R$_6$) to the appropriate acid, and then to replace the protective group by a hydrogen atom, for example by hydrogenolysis by means of hydrogen in the presence of a catalyst, such as palladium-on-charcoal, when it represents a benzyl or benzyloxycarbonyl radical, or by hydrolysis in acid medium, when it represents a tert-butoxycarbonyl or benzyloxycarbonyl radical.

When at least one of the $R_5$ and $R_6$ symbols is substituted by a carboxyl radical, it is particularly advantageous to protect it by a protective group, such as an alkyl radical optionally substituted by a phenyl radical, such as a benzyl radical, prior to the coupling of the amine of general formula HN(R$_5$) (R$_6$) to the appropriate acid, and then to replace the protective group by a hydrogen atom, for example by hydrogenolysis by means of hydrogen in the presence of a catalyst, such as palladium-on-charcoal, or by saponification under the conditions described above.

When, in the product of general formula (I), $R_5$ represents a hydrogen atom or an alkyl radical containing 1 to 6 carbon atoms and $R_6$ represents an alkyloxy radical substituted by a phenyl radical, replacement of the alkyloxy radical substituted by a phenyl radical by a hydroxyl radical, carried out, for example, by hydrogenolysis in the presence of a catalyst, such as palladium-on-charcoal, makes it possible to obtain a product of general formula (I) in which $R_5$ represents a hydrogen atom or an alkyl radical containing 1 to 4 carbon atoms and $R_6$ represents a hydroxyl radical.

According to the invention, the new products of general formula (I) in which $R_1$, $R_2$ and $R_3$ are defined as above, X represents an oxygen or sulphur atom or an —NH—, —CO—, methylene, ethylene, alkylidene or 1,1-cyclopalkyl group and Y represents an oxygen or sulphur atom and R represents a radical of general formula —NHCO—T in which T represents a hydrogen atom or an alkyl radical (1 to 6 carbon atoms) optionally substituted by an amino, carboxyl, alkyloxycarbonyl, hydroxyl, alkyloxy, mercapto or alkylthio radical can be obtained by reaction of an acid of general formula T—CO—OH, in which T is defined as above, with a product of general formula:

(VI)

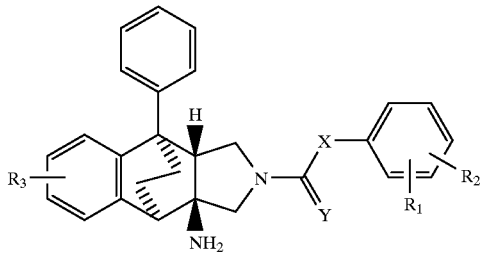

in which $R_1$, $R_2$, $R_3$, X and Y are defined as above, optionally followed by replacement of the protected ester functional groups or protected amine functional groups carried by T by carboxyl or amino radicals respectively, under the conditions described above.

Generally, the reaction of the acid of general formula T—CO—OH in the acid form with the product of general formula (VI) is carried out in an organic solvent, such as a halogenated aliphatic hydrocarbon, such as dichloromethane, in the presence of a coupling and/or activating agent, such as 1-ethyl-3-[3-(dimethylamino)propyl] carbodiimide hydrochloride, hydroxybenzotriazole, 1,1-dicyclohexylcarbodiimide or benzotriazol-1-oxytris (dimethylaminophosphonium hexafluorophosphate, at a temperature of between 0 and 50° C.

Generally, the reaction of the acid of general formula T—CO—OH in the halide form with the product of general formula (VI) is carried out in an organic solvent, such as a halogenated aliphatic hydrocarbon, such as dichloromethane, in the presence of a base (tertiary aliphatic amine), at a temperature of between 0 and 50° C.

Generally, the reaction of the acid of general formula T—CO—OH in the anhydride form with the product of general formula (VI) is carried out in an organic solvent, such as a halogenated aliphatic hydrocarbon, such as dichloromethane, in the presence of a base (tertiary aliphatic amine, pyridine or 4-dimethylaminopyridine), at a temperature of between 0 and 50° C.

When T is substituted by an amino radical, it is particularly advantageous to protect it by a protective group, such as a benzyloxycarbonyl or tert-butoxycarbonyl radical, prior to the coupling of the acid of general formula T—CO—OH to the appropriate amine, and then to replace the protective group by a hydrogen atom, for example by hydrogenolysis by means of hydrogen in the presence of a catalyst, such as palladium-on-charcoal, or by hydrolysis in acid medium.

When T is substituted by a carboxyl radical, it is particularly advantageous to protect it by a protective group, such as a methyl, ethyl or benzyl radical, prior to the coupling of the acid of general formula T—CO—OH to the appropriate amine, and then to replace the protective group by a hydrogen atom, for example by hydrogenolysis by means of hydrogen in the presence of a catalyst, such as palladium-on-charcoal, or by saponification under the conditions described above.

According to the invention, the new products of general formula (I) in which R represents a radical of formula

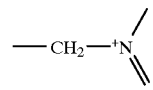

can be obtained by reaction of an excess of a tertiary amine and of a strong acid or of a derivative of this acid with a product of general formula:

(VII)

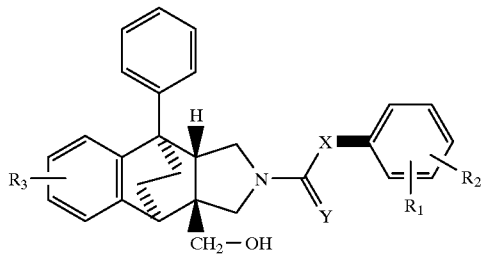

in which $R_1$, $R_2$, $R_3$, X and Y are defined as above.

The tertiary amine is preferably pyridine and the strong acid is preferably trifluoromethanesulphonic acid, optionally in the anhydride form.

According to the invention, the new products of general formula (I) in which Y represents a sulphur atom can be obtained by thionation from a product of general formula (I) in which Y represents an oxygen atom.

Generally, the thionation is carried out under the usual conditions by means of phosphorus pentasulphide in an organic solvent, such as tetrahydrofuran, at a temperature of between 0 and 50° C.

According to the invention, the products of general formula (I) in which one of the $R_1$ or $R_2$ symbols represents an alkoxycarbonyl radical can be obtained by acylation of a product of general formula (I) in which one of the $R_1$ or $R_2$ symbols represents a hydroxyl radical by means of an aliphatic acid or a derivative of this acid, such as a halide or the anhydride, under the usual esterification conditions.

The products of general formula (III) in which R represents a carboxyl radical or a radical of general formula $COOR_4$ can be obtained by the action of trifluoromethanesulphonic acid on a product of general formula:

(VIII)

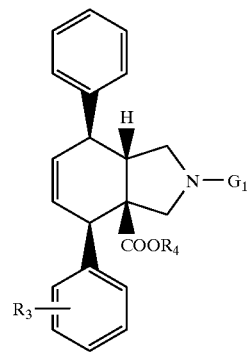

in which $R_3$ is defined as above, $G_1$ represents a benzyl radical and $R_4$ represents an alkyl radical containing 1 to 3 carbon atoms, optionally followed by saponification of the product obtained, and optionally followed, depending on the situation, by replacement of the benzyl radical by a hydrogen atom, by hydrogenolysis under the conditions described above, then, optionally, depending on the situation, by replacement of the hydrogen atom by a tert-butoxycarbonyl radical, by reaction with di-tert-butyl dicarbonate in an organic solvent, or by a benzyloxycarbonyl radical, by reaction with benzyl chloroformate in an organic solvent.

The product of general formula (VIII) can be obtained by reaction of an N-trialkylsilylmethyl-N-(alkoxymethyl) mine carrying a protective group for the amine functional group, such as a benzyl radical, such as N-trimethylsilylmethyl-N-(n-butoxymethyl)-benzylamine, which can be prepared under the conditions described in Chem. Pharm. Bull., 276 (1985), with a cyclohexadiene derivative of general formula:

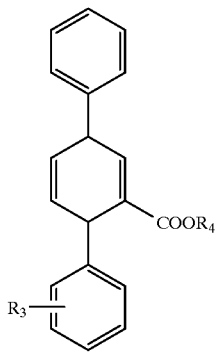

(IX)

in which $R_3$ and $R_4$ are defined as above.

Generally, the reaction is carried out in an organic solvent, such as a halogenated aliphatic hydrocarbon, such as dichloromethane, in the presence of a strong acid, such as trifluoromethanesulphonic acid, at a temperature of between 0 and 50° C.

The products of general formula (III) in which R represents a $(CH_2)_m$—$X_1(CH_2)_n$—Z radical in which m is equal to 0, $X_1$ represents a bond, n is equal to 0 and Z represents a —$COOR_4$ or —$CON(R_5)(R_6)$ radical can be obtained from a product of general formula (VIII) in which R represents a carboxyl radical by esterification and amidation under the conditions described above.

The product of general formula (IX) can be obtained by a Diels-Alder reaction between a 1,4-diphenylbutadiene, one of the phenyl radicals of which is optionally substituted by an $R_3$ radical as defined above, and propiolic acid by heating, optionally in the presence of hydroquinone, followed by esterification of the product obtained.

The products of general formula (III) in which m is equal to 1, $X_1$ represents a bond, n is equal to 0 and Z represents a —$COOR_4$, —$CON(R_5)(R_6)$ or $PO(OR_7)_2$ radical can be obtained from a product of general formula:

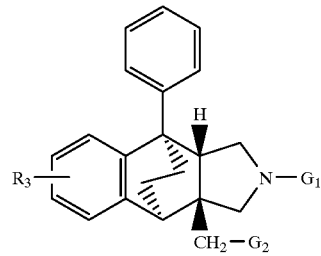

(X)

in which $R_3$ is defined as above and $G_1$ represents a protective group for the amine functional group (benzyl, benzyloxycarbonyl or tert-butoxycarbonyl) and $G_2$ represents a leaving group, such as a trifluoromethylsulphonyloxy radical.

More particularly, to obtain a product of general formula (III) in which Z represents a carboxyl, —$COOR_4$, in which $R_4$ represents an alkyl radical, or —$CON(R_5)(R_6)$ radical, it is particularly advantageous to pass through the intermediacy of the corresponding nitrile, which can be obtained by reaction of an alkali metal cyanide with the product of general formula (X) in a polar organic solvent, such as dimethyl sulphoxide, at a temperature of between 0 and 50° C., which is hydrolysed to the corresponding acid which can then be esterified or amidated under the usual conditions.

More particularly, to obtain a product of general formula (III) in which Z represents a —$PO(OR,)_2$ radical, it is particularly advantageous to react a trialkyl phosphite with a product of general formula (X) and then optionally to convert the phosphonate obtained to the corresponding phosphonic acid.

The products of general formula (III) in which R represents a $(CH_2)_m$—$X_1$—$(CH_2)_n$—Z radical in which m is equal to 1, $X_1$ represents an oxygen or sulphur atom, n is equal to 1 or 2, $G_1$ represents a protective group of the amine functional group and Z represents a carboxyl, —$COOR_4$, in which $R_4$ represents an alkyl radical, or —$CON(R_5)(R_6)$ radical can be obtained by reaction of an ester or of an amide of general formula:

H—$X_1$—$(CH_2)_n$—Z   (XI)

in which $X_1$, n and Z are defined as above, with a product of general formula (X) in an anhydrous organic solvent, such as dioxane, in the presence of an alkali metal hydride, such as sodium hydride, optionally followed, depending on the situation, by saponification of the product of general formula (III) thus obtained.

The products of general formula (III) in which m is equal to 1, $X_1$ represents a bond, n is equal to 1, it being possible for the methylene group to be substituted by a carboxyl or alkoxycarbonyl or carbamoyl or alkylcarbamoyl or dialkylcarbamoyl radical, $G_1$ represents a protective group for the amine functional group and Z represents a carboxyl, —$COOR_4$, in which $R_4$ represents an alkyl radical, or —$CON(R_5)(R_6)$ radical can be obtained by reaction of a malonic acid, anionized beforehand, or of a derivative of the malonic acid, preferably a diester, with a product of general formula (X) in an anhydrous organic solvent, such as dioxane, in the presence of an alkali metal hydride, such as sodium hydride, at a temperature of between 0° C. and the reflux temperature of the reaction mixture, followed, depending on the situation, by saponification, esterification, amidation or decarboxylation of the product of general formula (III) thus obtained.

The products of general formula (III) in which R represents an —NH—CO—T radical in which T is defined as above can be obtained by amidation of a product of general formula (III) in which $R_3$ is defined as above, $G_1$ represents a protective group for the amine functional group and R represents an amino radical by means of an acid of general formula T—CO—OH, in which T is defined as above, under the conditions described above for the amidation of a product of general formula (VI).

The products of general formula (III) in which R represents an amino radical or the products of general formula (VI) can be obtained according to the methods which make it possible to convert a carboxyl radical to an amino radical without affecting the remainder of the molecule.

Generally, the carboxyl functional group of a product of general formula (III) or (I) is converted to an amino radical via an isocyanate which can be obtained by pyrolysis of the acid azide, which can itself be obtained by reaction of an alkali metal azide with the corresponding acid halide.

The products of general formula (III) in which R represents a radical of general formula

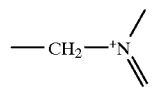

can be obtained by reaction of an excess of a tertiary amine and of a strong acid or of a derivative of this acid with a product of general formula:

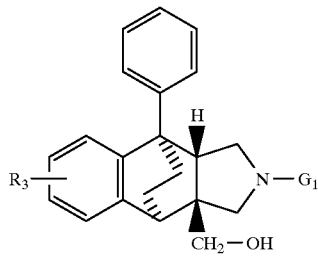

(XII)

in which $R_3$ is defined as above and $G_1$ represents a protective group for the amine functional group.

The products of general formula (VII) or of general formula (XII) can be obtained respectively by reduction of a product of general formula (I) or of a product of general formula (III) in which R represents a radical of general formula —COOR$_4$ in which $R_4$ preferably represents an alkyl radical containing 1 to 3 carbon atoms.

Generally, the reduction is carried out by means of a lithium aluminium hydride in an organic solvent, such as an ether, for example tetrahydrofuran, at a temperature of between 0 and 50° C.

The products of general formula (III) in which $R_3$ represents an iodine atom and $G_1$ represents a protective group for the amine functional group can be obtained by iodination of a product of general formula (III) in which $R_3$ represents a hydrogen atom and $G_1$ represents a protective group for the amine functional group.

Generally, the iodination can be carried out either by means of iodine in the presence of bis(trifluoroacetoxy) iodobenzene in an organic solvent, such as a halogenated aliphatic hydrocarbon, for example dichloromethane, at a temperature of between 0 and 50° C. or by reaction with iodine in the presence of ceric ammonium nitrate in acetic acid or methanol or by reaction with iodine in the presence of silver trifluoroacetate or by reaction with N-iodosuccinimide in the presence of hydroxy(toxyloxy) iodobenzene (Koser's reagent) in methanol or by reaction with benzyltrimethylammonium dichloroiodate in the presence of zinc chloride in acetic acid.

The products of general formula (III) in which $R_3$ represents an alkyl, alkenyl, alkyloxy, alkylthio, carboxyl or alkyloxycarbonyl radical can be obtained according to known methods which make it possible to replace an iodine atom by an alkyl, alkenyl, alkyloxy, alkylthio, carboxyl or alkyloxycarbonyl radical.

The products of general formula (III) in which $R_3$ represents an alkyl radical can be obtained by reaction of an alkali metal alkylide with a product of general formula (III) in which $R_3$ represents an iodine atom in an inert organic solvent, such as an ether.

The products of general formula (III) in which $R_3$ represents an alkenyl radical can be obtained by reaction of a boronic acid of general formula $R_3$—B(OH)$_2$ or of a stannane of general formula $R_3$—Sn(R')$_3$, in which R' represents an alkyl radical containing from 1 to 4 carbon atoms, in the presence of a catalyst, such as palladium in combination with a ligand (triphenylphosphine), in an aromatic solvent (benzene, toluene, xylene), at a temperature of between 0 and 100° C., with a product of general formula (III) in which $R_3$ represents an iodine atom.

The products of general formula (III) in which $R_3$ represents an alkyloxy or alkylthio radical can be obtained by reaction of an alkali metal alkoxide or sulphenate with a product of general formula (III) in which $R_3$ represents an iodine atom.

The products of general formula (III) in which $R_3$ represents a carboxyl radical can be obtained by oxidation, for example by means of sodium perborate, of a product of general formula formula (III) in which $R_3$ represents a formyl radical, which can itself be obtained by ozonolysis of a product of general formula (III) in which $R_3$ represents an alkenyl radical.

The products of general formula (III) in which $R_3$ represents an alkyloxycarbonyl radical can be obtained by esterification of a product of general formula (III) in which $R_3$ represents a carboxyl radical.

The isomers of the products of general formula (I) can be obtained according to the usual separation methods from the corresponding racemic product. It is particularly advantageous to carry out the separation by high performance liquid phase chromatography using a chiral stationary phase of modified Pirkle type, elution being carried out with a suitable solvent.

Use may preferably be made, as chiral stationary phase, of a phase in which the chiral selector, which is preferably 3,5-dinitrophenylalanine, is kept at a distance from the silica by an aminoalkyl arm containing 3 to 14 carbon atoms attached to the amine functional groups of an aminopropyl silica, the free silanol functional groups of which are blocked by trialkylsilyl radicals.

This chiral phase may be defined by the following structure:

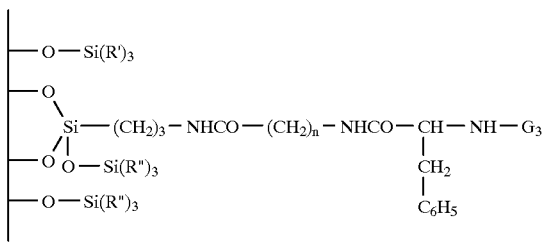

in which the R' symbols, which are identical or different, and the R" symbols, which are identical or different, represent alkyl radicals containing 1 to 10 carbon atoms, $G_3$ represents an electron-withdrawing group and n represents an integer between 3 and 13 inclusive, the porosity of which is in the region of 100 Å.

The chiral phase can be prepared by reaction of an aminopropyl silica with the anhydride of an aminoalkanoic acid containing 4 to 14 carbon atoms, the amine functional group of which is protected by a protective group, such as the tert-butoxycarbonyl radical, followed by blocking a part of the silanol functional groups by $Si(R')_3$ radicals as defined above, then, after removal of the protective groups for the amine functional group, by amidation by means of an amino acid of general formula:

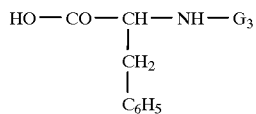

in which $G_3$ is defined as above, and finally blocking of the residual silanol functional groups by $Si(R")_3$ radicals as defined above.

Generally, the reaction of the anhydride of a protected aminoalkanoic acid with the aminopropyl silica is carried out in an anhydrous organic solvent, such as dimethylformamide, at a temperature in the region of 20° C.

Blocking of the silanol functional groups by —Si(R'$_3$) groups as defined above is carried out by reaction of a halotrialkylsilane with the aminopropyl silica, which has been grafted by aminoalkanoyl residues, in an organic solvent, such as methylene chloride, in the presence of a basic agent, such as pyridine.

Removal of the protective groups from the aminoalkanoyl residues is generally carried out, when the protective group is a tert-butoxycarbonyl radical, by the action of trifluoroacetic acid in an organic solvent, such as methylene chloride.

Amidation by means of phenylalanine in which the amine functional group is protected is carried out in the presence of a coupling agent, such as N-ethoxycarbonyl-2-ethoxy-1,2-dihydroquinoline, in an anhydrous organic solvent, such as dimethylformamide.

Blocking the residual silanol functional groups by —Si (R")$_3$ radicals as defined above is generally carried out by means of trialkylsilylimidazole in an organic solvent, such as methylene chloride.

The aminopropyl silica can be prepared by reaction of aminopropyltriethoxysilane with a silica in which the porosity is in the region of 100 Å in the presence of imidazole in an anhydrous organic solvent, such as an aromatic hydrocarbon, for example toluene.

The following examples illustrate the present invention.

EXAMPLE 1

450 g (2.2 mol) of (E,E)-1,4-diphenylbutadiene, 210 g (3 mol) of propiolic acid and 12.1 g (0.11 mol) of hydroquinone are heated at reflux for 24 hours under a nitrogen atmosphere in 2.5 liters of xylene. The crystals formed on cooling are filtered off, washed with xylene and then with petroleum ether and dried under reduced pressure. 454 g (76%) of cis-3,6 -diphenyl-1-4-cyclohexadienecarboxylic acid are thus obtained in the form of a light-beige powder, the characteristics of which are as follows: melting point= 179° C., $^1$H N.M.R. spectrum (250 MHz, d6-(CD$_3$)$_2$SO, δ in ppm): 4.40 (mt, 2H, CHAr), 5.78 and 6.92 (2 dmt, J=9 Hz, each 1H, CH=CH), 7.02 (mt, 1H, CH=), from 7.15 to 7.50 (mt, 10H, aromatic H of the two phenyls), 12.35 (unresolved peak, 1H, COOH).

200 g (0.73 mol) of enantiomer of cis-3,6-diphenyl-1-4-cyclohexadienecarboxylic acid are heated at reflux for 24 hours in 1.5 liters of methanol in the presence of 7.15 g (0.073 mol) of 96% sulphuric acid. After cooling, the methanol is concentrated under reduced pressure. The residue is taken up in 2 liters of dichloromethane and washed with 750 cm$^3$ of a saturated aqueous sodium hydrogencarbonate solution and then with water to neutrality. The organic phase is dried over magnesium sulphate and then stirred for 30 minutes with 2 kg of silica gel (70–230 mesh). After filtering off the silica and concentrating under reduced pressure, 185 g (88%) of the methyl ester of cis-3,6-diphenyl-1-4-cyclohexadienecarboxylic acid are obtained in the form of an orangey-yellow oil, the characteristics of which are as follows: mass spectrum (D.C.I.: NH$_3$) M/Z= 291 (MH$^+$)

116.2 g (0.4 mol) of the methyl ester of cis-3,6-diphenyl-1-4-cyclohexadienecarboxylic acid and 9.12 g (0.08 mol) of trifluoroacetic acid are heated to reflux in 600 cm$^3$ of dichloromethane. 335.4 g (1.2 mol) of N-trimethylsilylmethyl-N-(n-butoxymethyl)-benzylamine, which can be obtained according to Chem. Pharm. Bull., 276 (1985), are then added dropwise at reflux over approximately 2 hours. Stirring is maintained overnight, the temperature being allowed to rise to the region of 20° C. The reaction mixture is stirred with a 2N aqueous hydrochloric acid solution until the pH of the aqueous phase reaches 1. The organic phase is dried over sodium sulphate and concentrated under reduced pressure. The residual brown oil is taken up in 400 cm$^3$ of toluene. After standing for 48 hours, the crystals formed are filtered off. 123 g (67%) of the hydrochloride of the methyl ester of 2-benzyl-4,7-diphenyl-2,3,3a,4,7,7a-hexahydro-1H-isoindole-3a-carboxylic acid are obtained in the form of a light-beige powder, the characteristics of which are as follows: melting point= 208–212° C., $^1$H N.M.R. spectrum (250 MHz, CDCl$_3$, δ in ppm): from 2.55 to 2.80 (mt, 3H, CH$_2$ at 1 and H at 7a), 2.87 and 3.20 (2d, J=10 Hz, each 1H, CH$_2$ at 3), 3.30 (mt, 1H, H at 7), 3.38 (s, 3H, COOCH$_3$), 3.60 (mt, 1H, H at 4), 3.68 (s, 2H, NCH$_2$Ar), 6.08 (limit AB, 2H, CH=CH), from 7.20 to 7.45 (mt, 15H, aromatic H of the two phenyls at 4 and at 7 and aromatic H of the benzyl at 2).

200 cm$^3$ of trifluoromethanesulphonic acid are added dropwise over approximately 2 hours, while maintaining the temperature below 5° C., to a solution, cooled to 0–5° C., of 92 g (0.22 mol) of the methyl ester of 2-benzyl-4,7-diphenyl-2,3,3a,4,7,7a-hexahydro-1H-isoindole-3a-carboxylic acid in 1.4 liters of dry dichloromethane. After the end of the addition, the temperature of the reaction mixture is allowed to return to the region of 20° C. and the reaction mixture is then stirred for 20 hours. After cooling to 0° C., the mixture is hydrolysed with 130 cm$^3$ of water and then 460 cm$^3$ of 4N sodium hydroxide. After separation by settling, the aqueous phase is extracted with dichloromethane and the combined organic phases are then washed with water to neutrality. The orange residue, obtained by concentrating the dichloromethane, crystallizes on stirring in 800 cm³ of pentane. After filtration, the crystals are purified by high pressure chromatography on 2 kg of silica gel (15–40 mM), elution being carried out with a cyclohexane/ethyl acetate (98/2 by volume) mixture. 44 g (47%) of the methyl ester of (3aRS, 4SR, 9SR, 9aRS)-2-benzyl-4,9-ethano-9-phenyl-2,3,3a,4,9,9a-hexahydro-1H-benzo[f]-isoindole-3a-carboxylic acid are thus obtained in the form of a light-beige powder, the characteristics of which are as follows: melting point=125° C., ¹H N.M.R. spectrum (300 MHz, CDCl₃, δ in ppm): 1.45, 1.73 and 2.50 (3 mts, 1H, 1H and 2H respectively, CH₂CH₂), 2.38 and 3.25 (2 d, J=10 Hz, each 1H, CH₂ at 3), 2.36 and 2.75 (dd and d respectively, J=11 and 9 Hz and J=11 Hz, each 1H, CH₂ at 1), 3.30 (broad d, J=9 Hz, 1H, H at 9a), 3.35 and 3.70 (2 d, J=12.5 Hz, each 1H, NCH₂Ar), 3.42 (mt, 1H, H at 4), 3.58 (s, 3H, COOCH₃), 6.58 (broad d, J=7.5 Hz, 1H, H at 8), from 6.95 to 7.15 (mt, 3H, H at 5, H at 6 and H at 7), from 7.20 to 7.50 (mt, 10H, aromatic H of the phenyl at 9 and aromatic H of the benzyl at 2).

15 g (35 mmol) of the methyl ester of (3aRS, 4SR, 9SR, 9aRS)-2-benzyl-4,9-ethano-9-phenyl-2,3,3a,4,9,9a-hexahydro-1H-benzo[f]isoindole-3a-carboxylic acid, in solution in 360 cm³ of methanol, are reduced with 6.62 g of ammonium formate in the presence of 5.1 g of 5% (w/w) palladium-on-charcoal by heating at reflux for 3 hours. After cooling, the catalyst is separated by filtration and the methanol concentrated under reduced pressure. The oil obtained crystallizes on stirring in 200 cm³ of pentane. On filtering, 11.3 g (97%) of the methyl ester of (3aRS, 4SR, 9SR, 9aRS)-4,9-ethano-9-phenyl-2,3,3a,4,9,9a-hexahydro-1H-benzo[f]isoindole-3a-carboxylic acid are obtained in the form of white crystals, the characteristics of which are as follows: melting point=129–30° C., ¹H N.M.R. spectrum (200 MHz, d6-(CD₃)₂SO, δ in ppm): 1.36, 1.64 and from 2.15 to 2.45 (3 mts, 1H, 1H and 2H respectively, CH₂CH₂), 2.65 and 2.77 (2 dd, respectively J=11.5 and 3 Hz and J=11.5 and 7.5 Hz, each 1H, CH₂ at 1), 2.92 and 3.35 (2 d, J=11.5 Hz each 1H, CH₂ at 3), from 3.10 to 3.25 (mt, 1H, H at 9a), 3.45 (mt, 1H, H at 4), 3.52 (s, 3H, COOCH₃), 6.41 (broad d, J=7.5 Hz, 1H, H at 8), 7.04 (dt, J=7.5 and 2 Hz, 1H, H at 7), from 7.05 to 7.20 (mt, 2H, H at 5 and H at 6), from 7.30 to 7.60 (mt, 6H, aromatic H of the phenyl at 9 and NH).

2 g (6 mmol) of the methyl ester of (3aRS, 4SR, 9SR, 9aRS)-4,9-ethano-9-phenyl-2,3,3a,4,9,9a-hexahydro-1H-benzo[f]isoindole-3a-carboxylic acid and 1 g (6 mmol) of 2-methoxyphenylacetic acid, in solution in 50 cm³ of dichloromethane, are coupled by stirring in the presence of 1.27 g (6.6 mmol) of 1-ethyl-3-[3-(dimethylamino)propyl] carbodiimide dihydrochloride and 0.16 g (1.2 mmol) of hydroxybenzotriazole for 18 hours under a nitrogen atmosphere. After washing, by separation by settling, with 2 times 40 cm³ of water, the organic phase is dried over sodium sulphate and the dichloromethane is then evaporated under reduced pressure. The residue is purified by flash chromatography on silica gel (70–230 mesh), elution being carried out with a cyclohexane/ethyl acetate (70/30 by volume) mixture. 2.18 g (75%) of the methyl ester of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-carboxylic acid are thus obtained in the form of a light-beige powder, the characteristics of which are as follows: melting point=152–3° C., ¹H N.M.R. spectrum (400 MHz, d6-(CD₃)₂SO, at a temperature of 393 K, δ in ppm): 1.41, 1.66, 1.94 and 2.09 (4 mts, each 1H, CH₂CH₂), from 3.30 to 3.65 (mt, 6H, CH₂ at 1, COCH₂Ar, 1H of the CH₂ at 3 and H at 9a), 3.48 (mt, 1H, H at 4), 3.55 (s, 3H, COOCH₃), 3.70 (unresolved peak, 3H, OCH₃), 4.18 (d, J=12.5 Hz, 1H, the other H of the CH₂ at 3), 6.43 (broad d, J=7.5 Hz, 1H, H at 8), 6.90 (broad t, J=7.5 Hz, 1H, aromatic H para to the OCH₃), 6.96 (broad d, J=7.5 Hz, 1H, aromatic H ortho to the OCH₃), 7.06 (dt, J=7.5 and 2 Hz, 1H, H at 7), from 7.10 to 7.25 (mt, 4H, H at 5, H at 6 and aromatic H meta to the OCH₃), 7.39 (mt, 3H, aromatic H in the ortho and para positions of the phenyl at 9), 7.50 (t, J=7.50 Hz, 2H, aromatic H in the meta positions of the phenyl at 9).

EXAMPLE 2

2.1 g (4.35 mmol) of the methyl ester of (3aRS, 4SR, 9SR, 9aRS)-4,9-ethano-2-(2-methoxyphenyl)-acetyl-9-phenyl-2,3,3a,4,9,9a-hexahydro-1H-benzo[f]-isoindole-3a-carboxylic acid are heated at reflux for 18 hours in 27 cm³ of methanol and 45 cm³ of 1N sodium hydroxide. After cooling, the crystals formed are filtered off, then taken up in 200 cm³ of 1N hydrochloric acid and extracted with 2 times 100 cm³ of ethyl acetate. After concentrating the solvent under reduced pressure, the solid obtained is purified by recrystallizing from 50 cm³ of isopropyl ether. 1.36 g (67%) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-carboxylic acid are thus obtained in the form of white crystals, the characteristics of which are as follows: melting point=242–4° C., ¹H N.M.R. spectrum (400 MHz, d6-(CD₃)₂SO, at a temperature of 396 K, δ in ppm): 1.41, 1.66, 1.94 and 2.09 (4 mts, each 1H, CH₂CH₂), from 3.30 to 3.65 (mt, 6H, CH₂ at 1, COCH₂Ar, 1H of the CH₂ at 3 and H at 9a), 3.48 (mt, 1H, H at 4), 4.18 (d, J=12 Hz, 1H, the other H of the CH₂ at 3), 3.70 (unresolved peak, 3H, OCH₃), 6.42 (broad d, J=7.5 Hz, 1H, H at 8), 6.90 (broad t, J=7.5 Hz, 1H, aromatic H para to the OCH₃), 6.96 (broad d, J=7.5 Hz, 1H, aromatic H ortho to the OCH₃), 7.06 (dt, J=7.5 and 2 Hz, 1H, H at 7), from 7.10 to 7.25 (mt, 4H, H at 5, H at 6 and aromatic H meta to the OCH₃), 7.39 (mt, 3H, aromatic H in the ortho and para positions of the phenyl at 9), 7.50 (t, J=7.5 Hz, 2H, aromatic H in the meta positions of the phenyl at 9).

EXAMPLE 3

467 mg (1 mmol) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-carboxylic acid and 200 mg (1.2 mmol) of N,N'-carbonyldiimidazole are dissolved in 20 cm³ of dry dichloromethane. 10 cm³ of a 0.5N solution of ammonia in ethanol are then added and the mixture is then stirred for 16 hours at a temperature in the region of 20° C. After diluting with 50 cm³ of dichloromethane, the reaction mixture is washed successively, by separation by settling, with 50 cm³ of a 4N hydrochloric acid solution and then with 2 times 25 cm³ of a saturated sodium chloride solution, dried over sodium sulphate and concentrated under reduced pressure. The residue obtained is recrystallized from 13 cm³ of ethyl acetate. 350 mg (75%) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-carboxamide are thus obtained in the form of white crystals, the characteristics of which are as follows: melting point=262–4° C., ¹H N.M.R. spectrum (250 MHz, d6-(CD₃)₂SO, at a temperature of 383 K, δ in ppm): 1.36, 1.60, 1.88 and 2.05 (4 mts, each 1H, CH₂CH₂), from 3.20 to 3.65 (mt, 7H, CH₂ at 1, COCH₂Ar, 1H of the CH₂ at 3, H at 4 and H at 9a), 3.67 (unresolved peak, 3H, OCH₃), 4.22 (d, J=12.5 Hz, 1H, the other H of the CH$_2$ at 3), 6.37 (broad d, J=7.5 Hz, 1H, H at 8), 6.75 (unresolved peak, 2H, CONH$_2$), 6.88 (broad t, J=7.5 Hz, 1H, aromatic H para to the OCH$_3$), 6.94 (broad d, J=7.5 Hz, 1H, aromatic H ortho to the OCH$_3$), 7.02 (dt, J=7.5 and 2 Hz, 1H, H at 7), from 7.05 to 7.30 (mt, 4H, H at 5, H at 6 and aromatic H meta to the OCH$_3$), 7.39 (mt, 3H, aromatic H in the ortho and para positions of the phenyl at 9), 7.48 (t, J=7.5 Hz, 2H, aromatic H in the meta positions of the phenyl at 9).

EXAMPLE 4

From 500 mg (1.07 mmol) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-carboxylic acid, 113 mg (1.28 mmol) of N,N-dimethylethylenediamine, 246 mg (1.28 mmol) of 1-ethyl-3-(3-dimethylaminopropyl) carbodiimide hydrochloride and 14 mg (0.1 mmol) of hydroxybenzotriazole in solution in 30 cm$^3$ of dichloromethane, after stirring for 18 hours at a temperature in the region of 20° C. and recrystallizing the crude product obtained from 10 cm$^3$ of a cyclohexane/ethyl acetate (40/60 by volume) mixture, 530 mg (92%) (lacuna) (3aRS, 4SR, 9SR, 9aRS)-N-(2-dimethylaminoethyl)-4,9-ethano-2-(2-methoxyphenyl)acetyl-9-phenyl-2,3,3a,4,9,9a-hexahydro-1H-benzo[f]isoindole-3a-carboxamide are obtained in the form of light-beige crystals, the characteristics of which are as follows: melting point=99° C., mass spectrum: (D.C.I.: NH3) M/Z=538 (MH$^+$)

EXAMPLE 5

From 500 mg (1.07 nmol) of (3aRS, 4SR, 9SR, 9aRS)-4,9-ethano-2-(2-methoxyphenyl)acetyl-9-phenyl-2,3,3a,4,9,9a-hexahydro-1H-benzo [f]isoindole-3a-carboxylic acid, 95 mg (1.28 mmol) of N-methylethylenediamine, 246 mg (1.28 mmol) of 1-ethyl-3-(3-dimethylaminopropyl)carbodiimide hydrochloride and 14 mg (0.1 mmol) of hydroxybenzotriazole in solution in 30 cm$^3$ of dichloromethane, after stirring for 18 hours at a temperature in the region of 20° C. and recrystallizing the crude product obtained from 10 cm$^3$ of a cyclohexane/ethyl acetate (50/50 by volume) mixture, 525 mg (95%) [lacuna] (3aRS, 4SR, 9SR, 9aRS)-N-(2-methylaminoethyl)-4,9-ethano-2-(2-methoxyphenyl)acetyl-9-phenyl-2,3,3a,4,9,9a-hexahydro-1H-benzo[f]isoindole-3a-carboxamide are obtained in the form of light-yellow crystals, the characteristics of which are as follows: melting point=107° C., mass spectrum: (D.C.I. : NH3) M/Z=524 (MH$^+$)

EXAMPLE 6

From 500 mg (1.07 mmol) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-carboxylic acid, 735 mg (1.5 mmol) of the p-toluenesulphonate of the dibenzyl ester of aspartic acid, 290 mg (1.5 mmol) of 1-ethyl-3-(3 -dimethylaminopropyl)carbodiimide hydrochloride, 14 mg (0.1 mmol) of hydroxybenzotriazole and 152 mg (1.5 mmol) of triethylamine in solution in 30 cm$^3$ of dichloromethane, after stirring for 18 hours at a temperature in the region of 20° C. and then chromatographing the crude product obtained on silica gel (70–230 mesh), elution being carried out with a cyclohexane/ethyl acetate (70/30 by volume) mixture, 490 mg (67%) of the dibenzyl ester of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindolyl-3a-carbonyl]aspartic acid are obtained in the form of a white powder melting at 118° C.

470 mg (0.63 mmol) of the dibenzyl ester of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindolyl-3a-carbonyl]aspartic acid, in solution in 15 cm$^3$ of ethanol, are reduced by the action of hydrogen, at atmospheric pressure and in the presence of 50 mg of 20% (w/w) palladium hydroxide on charcoal, for 5 hours. After filtering off the catalyst and concentrating the ethanol under reduced pressure, the residue is recrystallized from toluene. 310 mg (83%) of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindolyl-3a-carbonyl]aspartic acid are thus obtained in the form of white crystals, the characteristics of which are as follows: melting point=194° C., mass spectrum (E.I.) M/Z=582 (M$^+$)

EXAMPLE 7

From 500 mg (1.07 mmol) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-carboxylic acid, 750 mg (1.5 mmol) of the p-toluenesulphonate of the dibenzyl ester of glutamic acid, 290 mg (1.5 mmol) of 1-ethyl-3-(3-dimethylaminopropyl)carbodiimide hydrochloride, 14 mg (0.1 mmol) of hydroxybenzotriazole and 152 mg (1.5 mmol) of triethylamine in solution in 30 cm$^3$ of dichloromethane, after stirring for 18 hours at a temperature in the region of 20° C. and then chromatographing the crude product obtained on silica gel (70–230 mesh), elution being carried out with a cyclohexane/ethyl acetate (80/20 by volume) mixture, 750 mg (96%) of the dibenzyl ester of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindolyl-3a-carbonyl]glutamic acid are obtained in the form of an oil which solidifies at approximately 30° C.

From 730 mg (0.96 mmol) of the dibenzyl ester of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindolyl-3a-carbonyl]glutamic acid, in the presence of 100 mg of 20% (w/w) palladium hydroxide on charcoal, after recrystallizing from a methanol/pentane (50/50 by volume) mixture, 200 mg (35%) of N-[(3aRS, 4SR, 9SR, 9aRS)-4,9-ethano-2-(2-methoxyphenyl)acetyl-9-phenyl-2,3,3a,4,9,9a-hexahydro-1H-benzo [fisoindolyl-3a-carbonyl]glutamic acid are obtained in the form of white crystals, the characteristics of which are as follows: melting point=168° C., mass spectrum (E.I.) M/Z=596 (M$^+$)

EXAMPLE 8

From 570 mg (1.2 mmol) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-carboxylic acid, 370 mg (1.54 mmol) of the dihydrochloride of the methyl ester of histidine, 300 mg (1.54 mmol) of 1-ethyl-3-(3-dimethylaminopropyl)carbodiimide hydrochloride, 18 mg (0.12 mmol) of hydroxybenzotriazole and 280 mg (2.8 mmol) of triethylamine in solution in 70 cm$^3$ of dichloromethane, after stirring for 18 hours at a temperature in the region of 20° C. and chromatographing the crude product obtained on silica gel (70–230 mesh), elution being carried out with a dichloromethane/methanol/acetic acid (96/2/2 by volume) mixture, 660 mg (89%) of the methyl ester of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindolyl-3a-carbonyl]histidine are obtained in the form of a white powder, the characteristics of which are as follows: melting point=200–204° C., mass spectrum (D.C.I.: NH3) M/Z=619 (MH$^+$)

From 640 mg (1.06 mmol) of the methyl ester of N-(3aRS, 4SR, 9SR, 9aRS)-4,9-ethano-2-(2-methoxyphenyl)acetyl-9-phenyl-2,3,3a,4,9,9a-hexahydro-1H-benzo[f]isoindolyl-3a-carbonyl]histidine, in 1.3 cm$^3$ of 1N sodium hydroxide and 30 cm$^3$ of ethanol, after heating at reflux for 18 hours and two recrystallizations of the crude product obtained from a 0.25N aqueous hydrochloric acid solution, 200 mg (29%) of the hydrochloride of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindolyl-3a-carbonyl]histidine are obtained in the form of white crystals, the characteristics of which are as follows: melting point= 245° C., mass spectrum (E.I.) M/Z=604 (M$^+$)

EXAMPLE 9

From 200 mg (0.42 mmol) of the dextrorotatory enantiomer of (3aRS, 4SR, 9SR, 9aRS)-4,9-ethano-2-[(2-methoxyphenyl)-2-methylenylacetyl]-9-phenyl-2,3,3a,4,9,9a-hexahydro-1H-benzo[f]isoindole-3a-carboxylic acid (Example 40), 60 mg (0.5 mmol) of (R)-1-phenylethylamine, 96 mg (0.5 mmol) of 1-ethyl-3-(3-dimethylaminopropyl)carbodiimide hydrochloride and 6 mg (0.045 mmol) of hydroxybenzotriazole in solution in 10 cm$^3$ of dichloromethane, after stirring for 18 hours at a temperature in the region of 20° C. and chromatographing the crude product obtained on a preparative silica plate, elution being carried out with a cyclohexane/ethyl acetate (50/50 by volume) mixture, 170 mg (71%) of the dextrorotatory enantiomer of (3aRS, 4SR, 9SR, 9aRS)-N-[(R)-1-phenylethyl)]-[4,9-ethano-2-(2-methoxyphenyl)-2-methylenylacetyl]-9-phenyl-2,3,3a,4,9,9a-hexahydro-1H-benzo[f]isoindole-3a-carboxamide are obtained in the form of a white powder, the characteristics of which are as follows: melting point=235° C., mass spectrum (E.I.) M/Z=582 (M$^+$)

EXAMPLE 10

470 mg of caesium carbonate are added to a solution of 300 mg (0.64 mmol) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-carboxylic acid in 5 cm$^3$ of dimethylformamide. After stirring for 30 minutes at a temperature in the region of 20° C., a solution of 820 mg (5 mmol) of ethyl iodide in 2.5 cm$^3$ of dimethylformamide is added and the mixture is then stirred at a temperature in the region of 20° C. for 18 hours. After diluting with 100 cm$^3$ of water, extraction is carried out twice with 50 cm$^3$ of ethyl acetate. After concentrating the solvent under reduced pressure, the residue obtained is purified by flash chromatography on silica gel (70–230 mesh), elution being carried out with a cyclohexane/ethyl acetate (70/30 by volume) mixture. 170 mg (54%) of the ethyl ester of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-carboxylic acid are thus obtained in the form of a white powder, the characteristics of which are as follows: melting point=196–7° C., mass spectrum (E.I.) M/Z=495 (M$^+$)

EXAMPLE 11

0.9 g (8.9 mmol) of triethylamine and 1.085 g (10 mmol) of ethyl chloroformate in solution in 40 cm$^3$ of acetone are successively added to a solution of 3.43 g (7.4 mmol) of (3aRS, 4SR, 9SR, 9aRS)-4,9-ethano-2-(2-methoxyphenyl) acetyl-9-phenyl-2,3,3a,4,9,9a-hexahydro-1H-benzo[f] isoindole-3a-carboxylic acid in 20 cm$^3$ of acetone and 6 cm$^3$ of water, which solution has been cooled to 0–2° C. and maintained under a nitrogen atmosphere. After stirring for 30 minutes at 0–5° C., a solution of 0.77 g (7.4 mmol) of sodium azide in 15 cm$^3$ of water is added dropwise and stirring is then maintained at 0–5° C. for 1 hour. The reaction mixture is then poured into 200 cm$^3$ of water and the acylazide is extracted with 5 times 40 cm$^3$ of ethyl ether. The combined organic phases are washed with water and then dried over magnesium sulphate. After evaporating the ether under reduced pressure, 50 cm$^3$ of toluene are added. The mixture is then gradually heated to 85–90° C. and then at reflux for 1 hour after gas evolution has ceased. The crystals formed on cooling are filtered off and then washed with petroleum ether. 2.98 g (88%) of (3aRS, 4SR, 9SR, 9aRS)-4,9-ethano-3a-isocyanate-2-(2-methoxyphenyl)acetyl-9-phenyl-2,3,3a,4,9,9a-hexahydro-1H-benzo[f]isoindole are thus obtained in the form of a white powder, the characteristics of which are as follows: melting point=185° C., mass spectrum (E.I.) M/Z=464 (M$^+$)

2.95 g (6.5 mmol) of (3aRS, 4SR, 9SR, 9aRS)-4,9-ethano-3a-isocyanate-2-(2-methoxyphenyl)acetyl-9-phenyl-2,3,3a,4,9,9a-hexahydro-1H-benzo[f]isoindole are heated at 60° C. for 12 hours with 760 mg (7 mmol) of benzyl alcohol and 123 mg (0.65 mmol) of p-toluenesulphonic acid in 100 cm$^3$ of toluene. 3.63 g (100%) of (3aRS, 4SR, 9SR, 9aRS)-3a-benzyloxycarbonylamino-4,9-ethano-2-(2-methoxyphenyl)acetyl-9-phenyl-2,3,3a,4,9,9a-hexahydro-1H-benzo[f]isoindole are thus obtained in the form of a white powder, the characteristics of which are as follows: melting point=114° C., mass spectrum (D.C.I.: NH3)=573 (MH$^+$)

3.6 g (6.48 mmol) of (3aRS, 4SR, 9SR, 9aRS)-3a-benzyloxycarbonylamino-4,9-ethano-2-(2-methoxyphenyl)acetyl-9-phenyl-2,3,3a,4,9,9a-hexahydro-1H-benzo[f]isoindole, in solution in 30 cm$^3$ of a dichloromethane/methanol (1/2 by volume) mixture, are reduced by the action of hydrogen at atmospheric pressure in the presence of 0.3 g of 5% (w/w) palladium-on-charcoal for 5 hours. After filtering off the catalyst and concentrating the solvent under reduced pressure, the residue is purified by flash chromatography on silica gel (70–230 mesh), elution being carried out with a dichloromethane/ethanol (9/1 by volume) mixture. 2.42 g (88%) of (3aRS, 4SR, 9SR, 9aRS)-3a-amino-4,9-ethano-2-(2-methoxyphenyl)acetyl-9-phenyl-2,3,3a,4,9,9a-hexahydro-1H-benzo[f]isoindole are thus obtained in the form of a white powder, the characteristics of which are as follows: melting point=92° C., $^1$H N.M.R. spectrum (300 MHz, d6-(CD$_3$) 2SO, δ in ppm): at room temperature, the mixture of two rotamers in the proportions 50/50 is observed. From 1.30 to 2.05 (mts, 6H, CH$_2$CH$_2$ and NH2), 2.35 (mt, 1H, H at 9a), from 2.85 to 3.75 (mt, 6H, CH$_2$ at 1, COCH$_2$Ar, 1H of the CH$_2$ at 3 and H at 4), 3.55 and 3.80 (2s, 3H in total, OCH$_3$), 4.10 and 4.17 (d, J=12.5 Hz, 1H in total, the other H of the CH$_2$ at 3), 6.38 and 6.43 (2 broad d, J=7.5 Hz, 1H in total, H at 8), from 6.85 to 7.55 (mt, 12H, H at 5, H at 6, H at 7, aromatic H ortho, meta and para to the OCH$_3$ and aromatic H of the phenyl at 9).

1 cm$^3$ of acetic anhydride is added, dropwise and at a temperature below 10° C., into 3 cm$^3$ of concentrated formic acid and the mixture is then heated for 1 hour at 50° C. After cooling, 438 g (1 mmol) of (3aRS, 4SR, 9SR, 9aRS)-3a-amino-4,9-ethano-2-(2-methoxyphenyl)acetyl-9-phenyl-2,3,3a,4,9,9a-hexahydro-1H-benzo[f]isoindole are added and stirring is maintained at a temperature in the region of 20° C. for 12 hours. The reaction mixture is then taken up in 50 cm$^3$ of water and 50 cm$^3$ of dichloromethane. The organic phase is separated by settling, washed with water and then dried over sodium sulphate. The crystals formed on addition of 50 cm$^3$ of isopropyl ether are filtered off. 215 mg (46%)

of (3aRS, 4SR, 9SR, 9aRS)-3a-formylamino-4,9-ethano-2-(2-methoxyphenyl)acetyl-9-phenyl-2,3,3a,4,9,9a-hexahydro-1H-benzo[f]isoindole are thus obtained in the form of white crystals, the characteristics of which are as follows: mass spectrum (D.C.I.: NH3) M/Z=429 (MH$^+$), melting point=236° C.,

EXAMPLE 12

From 400 mg (0.91 mmol) of (3aRS, 4SR, 9SR, 9aRS)-3a-amino-4,9-ethano-2-(2-methoxyphenyl)acetyl-9-phenyl-2,3,3a,4,9,9a-hexahydro-1H-benzo[f]isoindole, 200 mg (0.91 mmol) of N-(benzyloxycarbonyl)glycine, 200 mg (1.05 mmol) of 1-ethyl-3-(3-dimethylaminopropyl)carbodiimide hydrochloride and 14 mg (0.1 mmol) of hydroxybenzotriazole in solution in 20 cm$^3$ of dichloromethane, after stirring for 18 hours at a temperature in the region of 20° C. and purifying the crude product obtained by chromatography on silica (70–230 mesh), elution being carried out with ethyl acetate, 350 mg (62%) of (3aRS, 4SR, 9SR, 9aRS)-3a-[N-(benzyloxycarbonyl)glycyl]amino-[4,9-ethano-2-(2-methoxyphenyl)acetyl-9-phenyl-2,3,3a,4,9,9a-hexahydro-1H-benzo[f]isoindole are obtained in the form of a white powder, the characteristics of which are as follows: melting point=118° C., mass spectrum (D.C.I.: NH3) M/Z=630 (MH$^+$)

100 mg (0.16 mmol) of (3aRS, 4SR, 9SR, 9aRS)-3a-[N-(benzyloxycarbonyl)glycyl]amino-[4,9-ethano-2-(2-methoxyphenyl)acetyl-9-phenyl-2,3,3a,4,9,9a-hexahydro-1H-benzo[f]isoindole, in solution in 5 cm$^3$ of methanol, are treated with hydrogen at atmospheric pressure in the presence of 10 mg of 10% (w/w) palladium-on-charcoal for 4 hours. After separating the catalyst by filtration and evaporating the solvent, the residue is purified by chromatography on a preparative silica plate, elution being carried out with an ethyl acetate/methanol (98/2 by volume) mixture. 42 mg (51%) of (3aRS, 4SR, 9SR, 9aRS)-3a-glycylamino-4,9-ethano-2-(2-methoxyphenyl)acetyl-9-phenyl-2,3,3a,4,9,9a-hexahydro-1H-benzo[f]isoindole are thus obtained in the form of a white powder, the characteristics of which are as follows: melting point=210° C., mass spectrum (D.C.I.: NH3) M/Z=496 (MH$^-$)

EXAMPLE 13

From 600 mg (1.37 mmol) of (3aRS, 4SR, 9SR, 9aRS)-3a-amino-4,9-ethano-2-(2-methoxyphenyl)acetyl-9-phenyl-2,3,3a,4,9,9a-hexahydro-1H-benzo[f]isoindole, 400 mg (1.60 mmol) of N-(t-butoxycarbonyl)methionine, 303 mg (1.60 mmol) of 1-ethyl-3-(3-dimethylaminopropyl)carbodiimide hydrochloride and 20 mg (0.14 mmol) of hydroxybenzotriazole in solution in 30 cm$^3$ of dichloromethane, after stirring for 18 hours at a temperature in the region of 20° C. and purifying the crude product obtained by chromatography on silica gel (70–230 mesh), elution being carried out with a cyclohexane/ethyl acetate (30/70 by volume) mixture, 670 mg (73%) of (3aRS, 4SR, 9SR, 9aRS)-3a-[N-(t-butoxycarbonyl)methionyl]amino-[4,9-ethano-2-(2-methoxyphenyl)acetyl-9-phenyl-2,3,3a,4,9,9a-hexahydro-1H-benzo[f]isoindole are obtained in the form of a white powder, the characteristics of which are as follows: melting point=92° C., mass spectrum (D.C.I.: NH3) M/Z=670 (MH$^+$)

400 mg (0.6 mmol) of (3aRS, 4SR, 9SR, 9aRS)-3a-[N-(t-butoxycarbonyl)methionyl]amino-[4,9-ethano-2-(2-methoxyphenyl)acetyl-9-phenyl-2,3,3a,4,9,9a-hexahydro-1H-benzo[f]isoindole are heated at 50° C. for 3 hours in 40 cm$^3$ of methanol and 4 cm$^3$ of 4N hydrochloric acid. After diluting with 100 cm$^3$ of water, neutralizing to pH=8 with a 4N sodium hydroxide solution, extracting with 2 times 100 cm$^3$ of ethyl acetate, drying over magnesium sulphate and concentrating to dryness, an oil is obtained which is purified by flash chromatography on silica gel (70–230 mesh), elution being carried out with a dichloromethane/ethanol (92/8 by volume) mixture. 80 mg (22%) of (3aRS, 4SR, 9SR, 9aRS)-3a-methionylamino-4,9-ethano-2-(2-methoxyphenyl)acetyl-9-phenyl-2,3,3a,4,9,9a-hexahydro-1H-benzo[f]isoindole are thus obtained in the form of a white powder, the characteristics of which are as follows: melting point greater than 260° C., mass spectrum (D.C.I.: NH3) M/Z=569 (MH$^+$)

EXAMPLE 14

From 500 mg (1.14 mmol) of (3aRS, 4SR, 9SR, 9aRS)-3a-amino-4,9-ethano-2-(2-methoxyphenyl)acetyl-9-phenyl-2,3,3a,4,9,9a-hexahydro-1H-benzo[f]isoindole, 280 mg (1.37 mmol) of N-(t-butoxycarbonyl)serine, 262 mg (1.37 mmol) of 1-ethyl-3-(3-dimethylaminopropyl)carbodiimide hydrochloride and 15.5 mg (0.114 mmol) of hydroxybenzotriazole in solution in 20 cm$^3$ of dichloromethane, after stirring for 18 hours at a temperature in the region of 20° C. and purifying the crude product obtained by chromatography on silica gel (70–230 mesh), elution being carried out with ethyl acetate, 200 mg (28%) of (3aRS, 4SR, 9SR, 9aRS)-3a-[N-(t-butoxycarbonyl)seryl]amino-[4,9-ethano-2-(2-methoxyphenyl)acetyl-9-phenyl-2,3,3a,4,9,9a-hexahydro-1H-benzo[f]isoindole are obtained in the form of a white powder, the characteristics of which are as follows: melting point=110° C., mass spectrum (D.C.I.: NH3) M/Z=626 (MH$^+$)

EXAMPLE 15

From 600 mg (1.37 mmol) of (3aRS, 4SR, 9SR, 9aRS)-3a-amino-4,9-ethano-2-(2-methoxyphenyl)acetyl-9-phenyl-2,3,3a,4,9,9a-hexahydro-1H-benzo[f]isoindole, 220 mg (1.60 mmol) of the ethyl monoester of malonic acid, 300 mg (1.60 mmol) of 1-ethyl-3-(3-dimethylaminopropyl)carbodiimide hydrochloride and 20 mg (0.14 mmol) of hydroxybenzotriazole in solution in 20 cm$^3$ of dichloromethane, after stirring for 18 hours at a temperature in the region of 20° C. and purifying the crude product obtained by recrystallization from toluene, 680 mg (91%) of (3aRS, 4SR, 9SR, 9aRS)-4,9-ethano-3a-ethoxycarbonylacetylamino-2-(2-methoxyphenyl)acetyl-9-phenyl-2,3,3a,4,9,9a-hexahydro-1H-benzo[f]isoindole are obtained in the form of a white powder, the characteristics of which are as follows: melting point=110° C., mass spectrum (D.C.I.: NH3) M/Z=553 (MH$^+$)

EXAMPLE 16

From 490 mg (0.89 mmol) of (3aRS, 4SR, 9SR, 9aRS)-4,9-ethano-3a-ethoxycarbonylacetylamino-2-(2-methoxyphenyl)acetyl-9-phenyl-2,3,3a,4,9,9a-hexahydro-1H-benzo[f]isoindole in 0.9 cm$^3$ of 1N sodium hydroxide and 10 cm$^3$ of ethanol at reflux for 5 hours, after recrystallizing from 90% ethanol, 320 mg (70%) of (3aRS, 4SR, 9SR, 9aRS)-4,9-ethano-3a-carboxylacetylamino-2-(2-methoxyphenyl)acetyl-9-phenyl-2,3,3a,4,9,9a-hexahydro-1H-benzo[f]isoindole are obtained in the form of white crystals, the characteristics of which are as follows: melting point=228° C., mass spectrum (D.C.I.: NH3) M/Z=539 (MH$^+$)

EXAMPLE 17

90 mg (0.9 mmol) of succinic anhydride are added to a solution of 310 mg (0.7 mmol) of (3aRS, 4SR, 9SR, 9aRS)-

3a-amino-4,9-ethano-2-(2-methoxyphenyl)acetyl-9-phenyl-2,3,3a,4,9,9a-hexahydro-1H-benzo[f]isoindole in 20 cm³ of dichloromethane and the mixture is then stirred for 3 hours at a temperature in the region of 20° C. After concentrating the solvents under reduced pressure, the residue obtained is dissolved in 50 cm³ of 0.1N sodium hydroxide and the aqueous phase is then washed with 2 times 20 cm³ of ethyl acetate. After acidifying to pH=2 by addition of 0.5N ydrochloric acid, the precipitate formed is filtered off and then recrystallized from 50% ethanol. 200 mg (53%) of (3aRS, 4SR, 9SR, 9aRS)-4,9-ethano-3a-(3-carboxypropionyl)amino-2-(2-methoxyphenyl)acetyl-9-phenyl-2,3,3a,4,9,9a-hexahydro-1H-benzo[f]isoindole are thus obtained in the form of beige crystals, the characteristics of which are as follows: melting point=140° C., mass spectrum (D.C.I.: NH3) M/Z=481 [(M–COO+H)⁺]

EXAMPLE 18

A solution of 13.7 g (32 mmol) of the methyl ester of (3aRS, 4SR, 9SR, 9aRS)-2-benzyl-4,9-ethano-9-phenyl-2,3,3a,4,9,9a-hexahydro-1H-benzo[f]soindole-3a-carboxylic acid, obtained under the conditions of Example 1, in 130 cm³ of tetrahydrofuran is added, dropwise so as to maintain the temperature below 40° C., to a suspension of 1.23 g (32 mmol) of lithium aluminium hydride in 200 cm³ of dry tetrahydrofuran and the mixture is then kept stirring at 40° C. for 1 hour. After cooling, the slow addition is carried out of 12 cm³ of 1N sodium hydroxide and then magnesium sulphate. After filtering off the inorganic salts and concentrating to dryness, the residue obtained is purified on silica gel (70–230 mesh), elution being carried out with a cyclohexane/ethyl acetate (30/70 by volume) mixture. 12.15 g (96%) of (3aRS, 4SR, 9SR, 9aRS)-2-benzyl-4,9-ethano-9-phenyl-2,3,3a,4,9,9a-hexahydro-1H-benzo[f]isoindole-3a-methanol are obtained in the form of a white foam, the characteristics of which are as follows: ¹H N.M.R. spectrum (300 MHz, CDCl₃. δ in ppm): 1.43, 1.80 and from 2.35 to 2.55 (3 mts, respectively 1H, 1H and 2H, CH₂CH₂), from 2.25 to 2.45 and 2.62 (respectively mt and dd, J=9.5 and 8 Hz, 2H and 1H, CH₂ at 1 and H at 9a), 2.65 to 2.83 (2 d, J=10 Hz, each 1H, CH₂ at 3), 2.87 (mt, 1H, H at 4), from 2.95 to 3.15 (broad unresolved peak, 1H, OH), 3.03 and 3.32 (2 d, J=10.5 Hz, each 1H, CH₂O), 3.50 and 3.60 (2 d, J=13.5 Hz, each 1H, NCH₂Ar), 6.52 (broad d, J=7.5 Hz, 1H, H at 8), from 6.95 to 7.20 (mt, 3H, H at 5, H at 6 and H at 7), from 7.20 to 7.60 (mt, 10H, aromatic H of the phenyl at 9 and aromatic H of the benzyl at 2).

From 3.1 g (7.8 mmol) of (3aRS, 4SR, 9SR, 9aRS)-2-benzyl-4,9-ethano-9-phenyl-2,3,3a,4,9,9a-hexahydro-1H-benzo[f]isoindole-3a-methanol, in solution in 50 cm³ of methanol and in the presence of 300 mg of 20% (w/w) palladium hydroxide, after 2 hours under hydrogen at atmospheric pressure, filtering off the catalyst and concentrating to dryness under reduced pressure, 2.26 g (95%) of (3aRS, 4SR, 9SR, 9aRS)-4,9-ethano-9-phenyl-2,3,3a,4,9,9a-hexahydro-1H-benzo[flisoindole-3a-methanol are obtained in the form of a very viscous colourless oil, the characteristics of which are as follows: mass spectrum (E.I.) M/Z= 305 (M⁺)

From 2.25 g (7.4 mmol) of (3aRS, 4SR, 9SR, 9aRS)-4,9-ethano-9-phenyl-2,3,3a,4,9,9a-hexahydro-1H-benzo[f]isoindole-3a-methanol, 1.23 g (7.4 mmol) of 2-methoxyphenylacetic acid, 1.42 g (7.4 mmol) of 1-ethyl-3-(3-dimethylaminopropyl)carbodiimide hydrochloride and 100 mg (0.74 mmol) of hydroxybenzotriazole in solution in 60 cm³ of dichloromethane, after stirring for 18 hours at a temperature in the region of 20° C. and recrystallizing the crude product obtained from a toluene/isopropyl ether (1/1 by volume) mixture, 2.57 g (90%) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-methanol are obtained in the form of light-beige crystals, the characteristics of which are as follows: melting point=208° C., ¹H N.M.R. spectrum (250 MHz, d6-(CD₃)₂SO with the addition of a few drops of d4—CD₃COOD, at a temperature of 393 K, δ in ppm): 1.35, 1.68, from 1.90 to 2.15 (3 mts, respectively 1H, 1H and 2H, CH₂CH₂), 2.35 (mt, 1H, H at 9a), 2.95 (limit AB, J=10 Hz, 2H, CH₂0), 3.10 (mt, 1H, H at 4), from 3.20 to 3.50 (mt, 2H, CH₂ at 1), 3.58 (broad s, 2H, COCH₂Ar), from 3.55 to 3.75 (mt, 1H, 1H of the CH₂ at 3), 3.70 (unresolved peak, 3H, OCH₃), 3.90 (d, J=12.5 Hz, 1H, the other H of the CH₂ at 3), 6.41 (broad d, J=7.5 Hz, 1H, H at 8), from 6.85 to 7.00 (mt, 2H, aromatic H para and ortho to the OCH₃), 7.05 (dt, J=7.5 and 2 Hz, 1H, H at 7), from 7.10 to 7.30 (mt, 4H, H at 5, H at 6 and aromatic H meta to the OCH₃), from 7.30 to 7.55 (mt, 5H, aromatic H of the phenyl at 9).

500 mg (1.1 mmol) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-methanol are dissolved, at a temperature in the region of 20° C. under a nitrogen atmosphere, in 10 cm³ of pyridine which has been dried over potassium hydroxide and then 336 mg (1.2 mmol) of trifluoromethanesulphonic anhydride are added. After stirring for 3 hours at a temperature in the region of 20° C., 25 cm³ of water are added and extraction is carried out with 3 times 25 cm³ dichloromethane. The combined organic phases are washed with 0.1N hydrochloric acid and then with water, dried over magnesium sulphate and concentrated to dryness under reduced pressure. The residue is purified by recrystallizing from a methanol/isopropyl ether (60/40 by volume) mixture. 310 mg (42%) of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindolyl-3a-methyl] pyridinium trifluoromethanesulphonate are thus obtained in the form of pale-yellow crystals, the characteristics of which are as follows: melting point=244° C., ¹H N.M.R. spectrum (250 MHz, d6-(CD₃)₂SO, at a temperature of 393 K, δ in ppm): 1.37, 1.67, 1.98 and 2.12 (4 mts, each 1H, CH₂CH₂), 2.80 (mt, 1H, H at 9a), 3.20 (mt, 1H, H at 4), 3.38 (limit AB, 2H, CH₂ at 1), 3.52 (broad s, 2H, COCH₂Ar), 3.56 at 4.02 (2 d, J=12.5 Hz, each 1H, CH₂ at 3), 3.68 (unresolved peak, 3H, OCH₃), 4.38 and 4.50 (2 d, J=12.5 Hz, each 1H, CH₂N+), 6.51 (broad d, J=7.5 Hz, 1H, H at 8), 6.88 (broad t, J=7.5 Hz, 1H, aromatic H para to the OCH₃), 6.95 (broad d, J=7.5 Hz, 1H, aromatic H ortho to OCH₃), 7.15 (dt, J=7.5 and 2 Hz, 1H, H at 7), from 7.20 to 7.45 (mt, 4H, H at 5, H at 6 and aromatic H meta to the OCH₃), from 7.35 to 7.60 (mt, 5H, aromatic H of the phenyl at 9), 8.15 (broad t, J=7 Hz, 2H, H at 3 and H at 5 of the pyridyl), 8.65 (broad t, J=7 Hz, 1H, H at 4 of the pyridyl), 8.91 (broad t, J=7 Hz, 2H, H at 2 and H at 6 of the pyridyl).

EXAMPLE 19

9 g (23 mmol) of (3aRS, 4SR, 9SR, 9aRS)-2-benzyl-4,9-ethano-9-phenyl-2,3,3a,4,9,9a-hexahydro-1H-benzo[f]isoindole-3a-methanol are dissolved, at a temperature in the region of 20° C. and under a nitrogen atmosphere, in 100 cm³ of dry dioxane and 2.53 mg (25 mmol) of triethylamine and then 7.05 g (25 mmol) of trifluoromethanesulphonic anhydride are added. After stirring for 3 hours at a temperature in the region of 20° C., dilution is carried out with 200 cm³ of water and extraction is carried out with 3 times 250 cm³ of ethyl acetate. The organic phases are washed with water, dried over magnesium sulphate and then concentrated under reduced pressure. 12.5 g (95%) [lacuna] (3aRS, 4SR, 9SR, 9aRS)-2-benzyl-4,9-ethano-9-phenyl-3a-(trifluoromethylsulphonyloxy)methyl-2,3,3a,4,9,9a-hexahydro-1H-benzo[f]isoindole are thus obtained in the form of a colourless oil, the characteristics of which are as follows: mass spectrum (E.I.) M/Z=527 (M$^+$)

870 mg (1.65 mmol) of (3aRS, 4SR, 9SR, 9aRS)-2-benzyl-4,9-ethano-9-phenyl-3a-(trifluoromethylsulphonyloxy)methyl-2,3,3a,4,9,9a-hexahydro-1H-benzo[f]isoindole and 323 mg (6.6 mmol) of sodium cyanide are stirred for 18 hours at a temperature in the region of 20° C. in 20 cm$^3$ of dimethyl sulphoxide. After diluting with 100 cm$^3$ of water, extraction is carried out 3 times with 50 cm$^3$ of ethyl ether. The combined organic phases are washed with water, dried over magnesium sulphate and concentrated to dryness under reduced pressure. 640 mg (96%) [lacuna] (3aRS, 4SR, 9SR, 9aRS)-2-benzyl-3a-cyanomethyl-4,9-ethano-9-phenyl-2,3,3a,4,9,9a-hexahydro-1H-benzo[f]isoindole are thus obtained in the form of a white resin, the characteristics of which are as follows: mass spectrum (E.I.) M/Z=495 (M$^+$)

970 mg (2.4 mmol) of (3aRS, 4SR, 9SR, 9aRS)-2-benzyl-3a-cyanomethyl-4,9-ethano-9-phenyl-2,3,3a,4,9,9a-hexahydro-1H-benzo[f]isoindole are heated at reflux for 5 hours in 4 cm$^3$ of 50% aqueous sulphuric acid. After cooling, the reaction mixture is poured into 50 cm$^3$ of ice-cold water. The precipitate formed is filtered off, washed with 2 times 10 cm$^3$ of ice-cold water and dried under reduced pressure at 50° C., then taken up in 20 cm$^3$ of methanol in the presence of 1 cm$^3$ of concentrated sulphuric acid and heated at reflux overnight. The methanol is evaporated and the residue is then diluted with 20 cm$^3$ of water and extracted twice with 25 cm$^3$ of ethyl acetate. The organic phases are washed with water, dried over magnesium sulphate, filtered through 10 g of silica and concentrated to dryness under reduced pressure. 600 mg (59%) of the methyl ester of (3aRS, 4SR, 9SR, 9aRS)-2-benzyl-4,9-ethano-9-phenyl-2,3,3a,4,9,9a-hexahydro-1H-benzo[f]isoindole-3a-acetic acid are thus obtained in the form of a white powder, the characteristics of which are as follows: melting point=84–86° C., mass spectrum (E.I.) M/Z=437 (M$^+$)

From 800 mg (18 mmol) of the methyl ester of (3aRS, 4SR, 9SR, 9aRS)-2-benzyl-4,9-ethano-9-phenyl-2,3,3a,4,9,9a-hexahydro-1H-benzo[f]isoindole-3a-acetic acid, in solution in 20 cm$^3$ of methanol and in the presence of 100 mg of 20% (w/w) palladium hydroxide, after stirring for 2 hours under hydrogen at atmospheric pressure and at 40° C., filtering off the catalyst and concentrating to dryness under reduced pressure, 520 mg (83%) of the methyl ester of (3aRS, 4SR, 9SR, 9aRS)-4,9-ethano-9-phenyl-2,3,3a,4,9,9a-hexahydro-1H-benzo[f]isoindole-3a-acetic acid are obtained in the form of a white powder, the characteristics of which are as follows: melting point=71–73° C., mass spectrum (E.I.) M/Z=347 (M$^+$)

From 500 mg (1.44 mmol) of the methyl ester of (3aRS, 4SR, 9SR, 9aRS)-4,9-ethano-9-phenyl-2,3,3a,4,9,9a-hexahydro-1H-benzo[f]isoindole-3a-acetic acid, 260 mg (1.6 mmol) of 2-methoxyphenylacetic acid, 290 mg (1.6 mmol) of 1-ethyl-3-(3-dimethylaminopropyl)carbodiimide hydrochloride and 20 mg (0.14 mmol) of hydroxybenzotriazole in solution in 12 cm$^3$ of dichloromethane, after stirring for 18 hours at a temperature in the region of 20° C. and purifying by flash chromatography on silica gel (70–230 mesh), elution being carried out with a cyclohexane/ethyl acetate (1/1 by volume) mixture, 430 mg (61%) of the methyl ester of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-acetic acid are obtained in the form of a white powder, the characteristics of which are as follows: melting point=95° C., mass spectrum (E.I.) M/Z=495 (M$^+$)

From 394 mg (0.8 mmol) of the methyl ester of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-acetic acid, heated at reflux for 4 hours in 8 cm$^3$ of 1N sodium hydroxide and 4 cm$^3$ of methanol, 200 mg (52%) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-acetic acid are obtained, after purification by recrystallization from isopropyl ether, in the form of a white powder, the characteristics of which are as follows: melting point=171° C., $^1$H N.M.R. spectrum (250 MHz, d6-(CD$_3$)$_2$SO, at a temperature of 393 K, δ in ppm), 1.37, 1.64, from 1.85 to 2.15 (3 mts, respectively 1H, 12H and 2H, CH$_2$CH$_2$), 2.00 and 2.14 (2 d, J=15.5 Hz, each 1H, CH$_2$COO), 2.50 (mt, 1H, H at 9a), 3.20 (mt, 1H, H at 4), from 3.20 to 3.50 (mt, 2H, CH$_2$ at 1), from 3.55 to 3.70 (mt, 1H, 1H of CH$_2$ at 3), 3.56 (broad s, 2H, COCH$_2$Ar), 3.71 (unresolved peak, 3H, OCH$_3$), 4.12 (d, J=12.5 Hz, 1H, the other H of the CH$_2$ at 3), 6.43 (broad d, J=7.5 Hz, 1H, H at 8), 6.90 (t, J=7.5 Hz, 1H, aromatic H para to the OCH$_3$), 6.95 (d, J=7.5 Hz, 1H, aromatic H ortho to the OCH$_3$), from 7.05 to 7.30 (mt, 5H, H at 5, H at 6, H at 7 and aromatic H meta to the OCH$_3$), from 7.30 to 7.55 (mt, 5H, aromatic H of the phenyl at 9).

EXAMPLE 20

From 300 mg (0.6 mmol) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-acetic acid, 112.5 mg (0.9 mmol) of the methyl ester of glycine, 180 mg (0.9 mmol) of 1-ethyl-3-(3-dimethylaminopropyl)carbodiimide hydrochloride, 8 mg (0.06 mmol) of hydroxybenzotriazole and 101 mg (1 mmol) of triethylamine in solution in 10 cm$^3$ of dichloromethane, after stirring for 18 hours at a temperature in the region of 20° C. and purifying the crude product obtained by flash chromatography on silica gel (70–230 mesh), elution being carried out with a cyclohexane/ethyl acetate (4/6 by volume) mixture, 150 mg (45%) of the methyl ester of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-yl]acetylglycine are obtained in the form of a white powder, the characteristics of which are as follows: melting point=95° C., mass spectrum (D.C.I.: NH3) M/Z=553 (MH$^+$)

From 290 mg (0.525 mmol) of the methyl ester of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-yl]acetylglycine, heated at reflux for 4 hours in 10 cm$^3$ of 1N sodium hydroxide and 5 cm$^3$ of methanol, 180 mg (64%) of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-yl]acetylglycine are obtained, after purification by recrystallization from isopropyl ether, in the form of a white powder, the characteristics of which are as follows: melting point=172° C., mass spectrum (D.C.I.: NH3) M/Z=539 (MH$^+$)

EXAMPLE 21

From 300 mg (0.6 mmol) of (3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-acetic acid, 190 mg (0.9 mmol) of the methyl ester of methionine, 180 mg (0.9 mmol) of 1-ethyl-3-(3-dimethylaminopropyl)carbodiimide hydrochloride, 8 mg (0.06 mmol) of hydroxybenzotriazole and 101 mg (1 mmol) of triethylamine in solution in 10 cm³ of dichloromethane, after stirring for 18 hours at a temperature in the region of 20° C. and after purifying by flash chromatography on silica gel (70–230 mesh), elution being carried out with a cyclohexane/ethyl acetate (4/6 by volume) mixture, 200 mg (53%) of the methyl ester of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-yl]acetylmethionine are obtained in the form of a white powder, the characteristics of which are as follows: melting point= 96° C., mass spectrum (D.C.I.: NH3) M/Z=627 (MH⁺)

From 860 mg (1.4 mmol) of the methyl ester of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-yl]acetylmethionine, heated at reflux for 12 hours in 28 cm³ of 1N sodium hydroxide and 14 cm³ of methanol, 590 mg (69%) of N-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindole-3a-yl]acetylmethionine are obtained, after purification by crystallization from ethyl ether, in the form of a white powder, the characteristics of which are as follows: melting point=135° C., mass spectrum (D.C.I.: NH3) M/Z=613 (MH⁺)

EXAMPLE 22

A solution of 5 g (9.5 mmol) of (3aRS, 4SR, 9SR, 9aRS)-2-benzyl-4,9-ethano-9-phenyl-3a-(trifluoromethylsulphonyloxy)methyl-2,3,3a,4,9,9a-hexahydro-1H-benzo[f]isoindole, obtained under the conditions of Example 19, in 50 cm³ of triethyl phosphite is heated slowly to 100° C. At this point, a vigorous reaction takes place and the internal temperature reaches 145–150° C. Stirring is continued for 1 hour, the temperature being maintained between 100 and 110° C., and then for 18 hours, the temperature being allowed to fall to the region of 20° C. The reaction mixture is taken up in 100 cm³ of water and 200 cm³ of ethyl acetate. The organic phase is separated by settling, washed with water, dried over magnesium sulphate and concentrated to dryness under reduced pressure. The residue obtained is purified by flash chromatography on silica gel (70–230 mesh), elution being carried out with a cyclohexane/ethyl acetate (1/1 by volume) mixture. 1.46 g (29%) of the diethyl ester of [(3aRS, 4SR, 9SR, 9aRS)-2-benzyl-4,9-ethano-9-phenyl-2,3,3a,4,9,9a-hexahydro-1H-benzo[f]isoindol-3a-yl]methylphosphonic acid are thus obtained in the form of a pale-yellow oil, the characteristics of which are as follows: mass spectrum (E.I.) M/Z=515 (M⁺)

From 460 mg (0.9 mmol) of the diethyl ester of [(3aRS, 4SR, 9SR, 9aRS)-2-benzyl-4,9-ethano-9-phenyl-2,3,3a,4,9,9a-hexahydro-1H-benzo[f]isoindol-3a-yl]methylphosphonic acid, in solution in 20 cm³ of ethanol and in the presence of 100 mg of 20% (w/w) palladium hydroxide, after stirring for 6 hours under hydrogen at atmospheric pressure and at 60° C., filtering off the catalyst and concentrating to dryness under reduced pressure, 370 mg (97%) of the diethyl ester of [(3aRS, 4SR, 9SR, 9aRS)-4,9-ethano-9-phenyl-2,3,3a,4,9,9a-hexahydro-1H-benzo[f]isoindol-3a-yl]methylphosphonic acid are obtained in the form of a colourless oil, the characteristics of which are as follows: mass spectrum (D.C.I.: NH3) M/Z=425 (MH⁺)

From 600 mg (1.41 mmol) of the diethyl ester of [(3aRS, 4SR, 9SR, 9aRS)-4,9-ethano-9-phenyl-2,3,3a,4,9,9a-hexahydro-1H-benzo[f]isoindol-3a-yl]methylphosphonic acid, 260 mg (1.56 mmol) of 2-methoxyphenylacetic acid, 300 mg (1.56 mmol) of 1-ethyl-3-(3-dimethylaminopropyl)carbodiimide hydrochloride and 19 mg (0.14 mmol) of hydroxybenzotriazole in solution in 20 cm³ of dichloromethane, after stirring for 18 hours at a temperature in the region of 20° C. and purifying the crude product obtained by flash chromatography on silica gel (70–230 mesh), elution being carried out with a cyclohexane/ethyl acetate (1/9 by volume) mixture, 350 mg (43%) of the diethyl ester of [(3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-yl]methylphosphonic acid are obtained in the form of a white powder, the characteristics of which are as follows: melting point=130° C., ¹H N.M.R. spectrum (400 MHz, d6-(CD₃)₂SO with the addition of a few drops of d4—CD₃COOD, at a temperature of 403 K, δ in ppm): 1.23 and 1.25 (2 t, J=7 Hz, 6H, CH₃ of the ethyl), 1.37, 1.64, 190 and 2.05 (4 mts, each 1H, CH₂CH₂), from 1.55 to 1.85 (mt, 2H, CH₂P), 2.62 (mt, 1H, H at 9a), 3.28 (mt, 1H, H at 4), from 3.30 to 3.50 (mt, 2H, CH₂ at 1), 3.58 (broad s, 2H, COCH₂Ar), from 3.65 to 3.80 (mt, 1H, 1H of the CH₂ at 3), 3.70 (unresolved peak, 3H, OCH₃), from 3.85 to 4.10 (mt, 4H, OCH₂ of the ethyl), 4.09 (d, J=13 Hz, 1H, the other H of the CH₂ at 3), 6.44 (broad d, J=7.5 Hz, 1H, H at 8), 6.88 (t, J=7.5 Hz, 1H, aromatic H para to the OCH₃), 6.93 (d, J=7.5 Hz, 1H, aromatic H ortho to the OCH₃), 7.07 (dt, J=7.5 and 1.5 Hz, 1H, H at 7), from 7.15 to 7.35 (mt, 4H, H at 5, H at 6 and aromatic H meta to the OCH₃), 7.35 (mt, 3H, aromatic H in the ortho and para positions of the phenyl at 9), 7.47 (t, J=7.5 Hz, 2H, aromatic H in the meta positions of the phenyl at 9).

EXAMPLE 23

850 mg (1.5 mmol) of the diethyl ester of [(3aRS, 4SR, 9SR, 9aRS)-4,9-ethano-2-(2-methoxyphenyl)-acetyl-9-phenyl-2,3,3a,4,9,9a-hexahydro-1H-benzo[f]isoindol-3a-yl] methylphosphonic acid are dissolved in 10 cm³ of dry carbon tetrachloride, cooling is then carried out to approximately -20° C. and 600 mg (3 mmol) of trimethylsilyl iodide are added. The temperature is gradually allowed to rise to a temperature in the region of 20° C. over 2–3 hours and stirring is then carried out for a further 1 hour. 2 cm³ of water and 2 cm³ of a 0.1N aqueous sodium thiosulphate solution are then added and extraction is then carried out with ether. The organic phase is washed with water, dried over sodium sulphate and concentrated to dryness under reduced pressure. The residual oil is crystallized from 20 cm³ of 80% (by volume) aqueous ethanol and then triturated at reflux in 25 cm³ of ethanol. 230 mg (30%) of [(3aRS, 4SR, 9SR, 9aRS)-4,9-ethano-2-(2-methoxyphenyl)acetyl-9-phenyl-2, 3,3a,4,9,9a-hexahydro-1H-benzo[f3isoindol-3a-yl] methylphosphonic acid are thus obtained in the form of a white powder, the characteristics of which are as follows: melting point greater then 260° C., mass spectrum (D.C.I.: NH3) M/Z=518 (MH⁺)

EXAMPLE 24

A solution of 436 mg (3.3 mmol) of methyl malonate in 10 cm³ of dry dioxane is added dropwise to a suspension of 160 mg (3.3 mmol) of sodium hydride (at 50% in oil) in 20 cm³ of dry dioxane. The mixture is stirred at a temperature in the region of 20° C. for 30 minutes after hydrogen evolution has ceased and then a solution of 1.52 g (2.9 mmol) of (3aRS, 4SR, 9SR, 9aRS)-2-benzyl-4,9-ethano-9-phenyl-3a-(trifluoromethylsulphonyloxy)methyl-2,3,3a,4,9, 9a-hexahydro-1H-benzo[ffisoindole, obtained under the conditions of Example 19, in 20 cm³ of dry dioxane is slowly added. The reaction mixture is heated for 1 hour at reflux and then stirred for 18 hours at a temperature in the region of 20° C. After diluting with 100 cm³ of water, extraction is carried out 3 times with 50 cm³ of ethyl acetate. The organic phases are washed with water, dried over sodium sulphate, filtered through 10 g of silica and concentrated to dryness under reduced pressure. 1.21 g (82%) of the dimethyl ester of 2-[(3aRS, 4SR, 9SR, 9aRS)-2-benzyl-4,9-ethano-9-phenyl-2,3,3a,4,9,9a-hexahydro-1H-benzo[f]isoindol-3a-yl]methylmalonic acid are thus obtained in the form of a colourless oil, the characteristics of which are as follows: mass spectrum (D.C.I.: NH3) M/Z=510 (MH⁺)

From 1.2 g (2.3 mmol) of the dimethyl ester of 2-[(3aRS, 4SR, 9SR, 9aRS)-2-benzyl-4,9-ethano-9-phenyl-2,3,3a,4,9,9a-hexahydro-1H-benzo[f]isoindol-3a-yl]methylmalonic acid, in solution in 20 cm³ of methanol and in the presence of 250 mg of 20% (w/w) palladium hydroxide, after 6 hours under hydrogen at atmospheric pressure and at 60° C., filtering off the catalyst and concentrating to dryness under reduced pressure, 930 mg (96%) of the dimethyl ester of 2-[(3aRS, 4SR, 9SR, 9aRS)-4,9-ethano-9-phenyl-2,3,3a,4,9,9a-hexahydro-1H-benzo[f]isoindol-3a-yl]methylmalonic acid are obtained in the form of a colourless oil, the characteristics of which are as follows: mass spectrum (D.C.I.: NH3) M/Z=420 (MH⁺)

From 530 mg (1.27 mmol) of the dimethyl ester of 2-[(3aRS, 4SR, 9SR, 9aRS)-4,9-ethano-9-phenyl-2,3,3a,4,9,9a-hexahydro-1H-benzo[f]isoindol-3a-yl]methylmalonic acid, 232 mg (1.4 mmol) of (2-methoxyphenyl)acetic acid, 270 mg (1.4 mmol) of 1-ethyl-3-(3-dimethylaminopropyl) carbodiimide hydrochloride and 17 mg (0.13 mmol) of hydroxybenzotriazole in solution in 20 cm³ of dichloromethane, after stirring for 18 hours at a temperature in the region of 20° C. and purifying the crude product obtained by flash chromatography on silica gel (70–230 mesh), elution being carried out with a cyclohexane/ethyl acetate (1/9 by volume) mixture, 350 mg (47%) of the dimethyl ester of 2-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-yl]methylmalonic acid are obtained in the form of a white powder, the characteristics of which are as follows: melting point=75° C., mass spectrum (D.C.I.: NH3) M/Z=568 (MH⁺)

From 280 mg (0.5 mmol) of the dimethyl ester of 2-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-yl]methylmalonic acid, heated at reflux for 4 hours in 10 cm³ of 1N sodium hydroxide and 5 cm³ of methanol, 110 mg (41%) of 2-{(3aRS, 4SR, 9SR, 9aRS)-4,9-ethano-[(2-methoxyphenyl)acetyl]-9-phenyl-1,2,3,3a,9,9a-hexahydro-1H-benzo[f]isoindole-3a-}-methylmalonic acid are obtained, after purification by crystallization from isopropyl ether, in the form of a white powder, the characteristics of which are as follows: melting point=200° C., mass spectrum (D.C.I.: NH3) M/Z=539 (MH⁺)

EXAMPLE 25

A solution of 770 mg (1.4 mmol) of 2-[(3aRS, 4SR, 9SR, 9aRS)-4,9-ethano-2-(2-methoxyphenyl)acetyl-9-phenyl-1,2,3,3a,9,9a-hexahydro-1H-benzo[f]isoindol-3a-yl]methylmalonic acid in 20 cm³ of acetonitrile is heated in the presence of 19.6 mg (0.14 mmol) of cuprous oxide at approximately 80–90° C. until evolution of carbon dioxide begins. When gas evolution ceases, heating is maintained for 2 minutes and then the mixture is rapidly cooled. Dilution is carried out with 50 cm³ of ethyl acetate and 2 cm³ of a 1N aqueous ammonia solution. The gel obtained is filtered successively through celite and then through silica. After removing the solvents, the residue is taken up in 20 cm³ of dichloromethane. The organic phase is washed with 0.5N aqueous hydrochloric acid, dried over magnesium sulphate and concentrated to dryness under reduced pressure. On crystallization from isopropyl ether, 220 mg (32%) of 3-[(3aRS, 4SR, 9SR, 9aRS)-4,9-ethano-2-(2-methoxyphenyl)acetyl-9-phenyl-1,2,3,3a,9,9a-hexahydro-1H-benzo[f]isoindol-3a-yl]propionic acid are obtained in the form of a white powder, the characteristics of which are as follows: melting point=200° C., ¹H N.M.R. spectrum (250 MHz, d6-(CD₃)₂SO, at a temperature of 393 K, δ in ppm): 1.25 and 1.38 (2 mts, each 1H, CH₂ of the propionyloxy), 1.38, 1.67, 1.90 and 2.06 (4 mts, each 1H, CH₂CH₂), 2.20 and 2.35 (2 mts, each 1H, CH₂COO of the propionyloxy), 2.38 (mt, 1H, H at 9a), 3.06 (mt, 1H, H at 4), from 3.30 to 3.55 (mt, 2H, CH₂ at 1), from 3.40 to 3.70 (mt, 1H, 1H of the CH₂ at 3), 3.58 (broad s, 2H, COCH₂Ar), 3.70 (unresolved peak, 3H, OCH₃), 4.00 (d, J=12.5 Hz, 1H, the other H of the CH₂ at 3), 6.44 (broad d, J=7.5 Hz, 1H, H at 8), 6.90 (t, J=7.5 Hz, 1H, aromatic H para to the OCH₃), 6.95 (d, J=7.5 Hz, 1H, aromatic H ortho to the OCH₃), 7.07 (dt, J=7.5 and 1.5 Hz, 1H, H at 7), from 7.15 to 7.35 (mt, 4H, H at 5, H at 6 and aromatic H meta to the OCH₃), 7.35 (mt, 3H, aromatic H in the ortho and para positions of the phenyl at 9), 7.48 (broad t, J=7.5 Hz, 2H, aromatic H in the meta positions of the phenyl at 9).

EXAMPLE 26

From 436 mg (3.3 mmol) of the methyl ester of 3-mercaptopropanoic acid in 10 cm³ of dry dioxane, 160 mg (3.3 mmol) of sodium hydride (at 50% in oil) in 20 cm³ of dry dioxane and 1.52 g (2.9 mmol) of (3aRS, 4SR, 9SR, 9aRS)-2-benzyl-4,9-ethano-9-phenyl-3a-(trifluoromethylsulphonyloxy)methyl-2,3,3a,4,9,9a-hexahydro-1H-benzo[f]isoindole, obtained under the conditions of Example 19, in 20 cm³ of dry dioxane, heated for 1 hour at reflux and then stirred for 18 hours at a temperature in the region of 20° C., 1.34 g (93%) of the methyl ester of 3-[(3aRS, 4SR, 9SR, 9aRS)-2-benzyl-4,9-ethano-9-phenyl-2,3,3a,4,9,9a-hexahydro-1H-benzo[f]isoindol-3a-yl]methylthiopropanoic acid are obtained in the form of a pale-yellow oil, the characteristics of which are as follows: mass spectrum (E.I.) M/Z=497 (M⁺)

A solution of 257 mg of 1-chloroethyl chloroformate in 5 cm³ of dry dichloromethane is added dropwise, under the nitrogen atmosphere and while maintaining the temperature below 0° C., to a solution, cooled to –10° C., of 600 mg (1.2 mmol) of the methyl ester of 3-[(3aRS, 4SR, 9SR, 9aRS)-2-benzyl-4,9-ethano-9-phenyl-2,3,3a,4,9,9a-hexahydro-1H-benzo[f]isoindol-3a-yl]methylthiopropanoic acid in 10 cm³ of dry dichloromethane. After stirring for 30 minutes at 0° C. and then for 1 hour at a temperature in the region of 20° C., the reaction mixture is concentrated to dryness and the residue is taken up in 10 cm³ of dry methanol, heated at reflux for 2 hours and then stirred at a temperature in the region of 20° C. for 18 hours. After concentrating the methanol under reduced pressure, the residue is taken up in 20 cm³ of dichloromethane. The organic phase is washed with water, dried over sodium sulphate and concentrated to dryness. 400 mg (82%) of the methyl ester of 3-[(3aRS, 4SR, 9SR, 9aRS)-4,9-ethano-9-phenyl-2,3,3a,4,9,9a-hexahydro-1 H-benzo(f]isoindol-3a-yl]methylthiopropanoic acid are thus obtained in the form of a pale-yellow oil.

From 390 mg (0.96 mmol) of the methyl ester of 3-[(3aRS, 4SR, 9SR, 9aRS)-4,9-ethano-9-phenyl-2,3,3a,4,9, 9a-hexahydro-1H-benzo[f]isoindol-3a-yl] methylthiopropanoic acid, 190 mg (1.1 mmol) of 2-methoxyphenylacetic acid, 220 mg (1.1 mmol) of 1-ethyl-3-(3-dimethylaminopropyl)carbodiimide hydrochloride and 14 mg (0.1 mmol) of hydroxybenzotriazole in solution in 20 cm³ of dichloromethane, after stirring for 18 hours at a temperature in the region of 20° C. and purifying the crude product obtained by flash chromatography on silica gel (70–230 mesh), elution being carried out with a cyclohexane/ethyl acetate (6/4 by volume) mixture, 210 mg (39%) of the methyl ester of 3-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-yl] methylthiopropanoic acid are obtained in the form of a white resin, the characteristics of which are as follows: melting point=30–35° C., mass spectrum (D.C.I.: NH3) M/Z=555 (MH⁺)

From 180 mg (0.32 mmol) of the methyl ester of 3-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-yl]methylthiopropanoic acid, heated at reflux for 4 hours in 6.4 cm³ of 1N sodium hydroxide and 3.2 cm³ of methanol, 120 mg (69%) of 3-[(3aRS, 4SR, 9SR, 9aRS)-4,9-ethano-2-(2-methoxyphenyl)acetyl-9-phenyl-2,3,3a,4,9,9a-hexahydro-1H-benzo[f]isoindol-3a-yl]methylthiopropanoic acid are obtained, after purification by crystallization from isopropyl ether, in the form of a white powder, the characteristics of which are as follows: melting point=120° C., ¹H N.M.R. spectrum (250 MHz, d6-(CD3)₂SO, at a temperature of 393 K, δ in ppm): 1.38, 1.67 and from 1.85 to 2.15 (3 mts, respectively 1H, 1H and 2H, CH₂CH₂), 2.26 and 2.41 (2 d, J=12 Hz, each 1H, CH₂S), 2.40 (t, J=7 Hz, 2H, CH₂COO), 2.54 (mt, 1H, H at 9a), 2.66 (t, J=7 Hz, 2H, CH₂S), 3.16 (mt, 1H, H at 4), from 3.30 to 3.75 (mt, 3H, CH₂ at 1 and 1H of the CH₂ at 3), 3.58 (broad s, 2H, COCH₂Ar), 3.72 (unresolved peak, 3H, OCH₃), 4.00 (d, J=12.5 Hz, 1H, the other H of the CH₂ at 3), 6.44 (broad d, J=7.5 Hz, 1H, H at 8), 6.90 (t, J=7.5 Hz, 1H, aromatic H para to the OCH₃), 6.95 (d, J=7.5 Hz, 1H, aromatic H ortho to the OCH₃), 7.09 (dt, J=7.5 and 1.5 Hz, 1H, H at 7), from 7.15 to 7.35 (mt, 4H, H at 5, H at 6 and aromatic H meta to the OCH₃), from 7.35 [lacuna] 7.45 (mt, 3H, aromatic H in the ortho and para positions of the phenyl at 9), 7.49 (broad t, J=7.5 Hz, 2H, aromatic H in the meta positions of the phenyl at 9).

EXAMPLE 27

From 1.2 g (3.6 mmol) of the methyl ester of (3aRS, 4SR, 9SR, 9aRS)-4,9-ethano-9-phenyl-2,3,3a,4,9,9a-hexahydro-1H-benzo[f]isoindole-3a-carboxylic acid, obtained under the conditions of Example 1, heated at reflux for 4 hours in 36 cm³ of 2N sodium hydroxide and 36 cm³ of ethanol, after purifying the crude product obtained after concentrating by dissolving in N sodium hydroxide and reprecipitating by neutralizing to pH=6.5 with N hydrochloric acid solution, 1.12 g (97%) of (3aRS, 4SR, 9SR, 9aRS)-4,9-ethano-9-phenyl-2,3,3a,4,9,9a-hexahydro-1H-benzo[f]isoindole-3a-carboxylic acid are obtained in the form of a white powder, the characteristics of which are as follows: melting point greater than 260° C., mass spectrum (E.I.) M/Z=319 (M⁺)

500 mg (1.56 mmol) of (3aRS, 4SR, 9SR, 9aRS)-4,9-ethano-9-phenyl-1,2,3,3a,9,9a-hexahydro-1H-benzo[f]isoindole-3a-carboxylic acid are dissolved in 50 cm³ of O.1N sodium hydroxide and 50 cm³ of dioxane by heating to 60° C. After cooling to a temperature in the region of 20° C., 580 mg (3.12 mmol) of (2-methoxyphenyl)methyl chloroformate are added and the mixture is then stirred for 4 days at a temperature in the region of 20° C. After concentrating to dryness, the residue is purified by chromatography on a preparative silica plate, elution being carried out with a dichloromethane/methanol/acetic acid (90/6/4 by volume) mixture. 175 mg (24%) of (3aRS, 4SR, 9SR, 9aRS)-4,9-ethano-2-(2-methoxyphenyl)oxycarbonyl-9-phenyl-1,2,3,3a,9,9a-hexahydro-1H-benzo[f]isoindole-3a-carboxylic acid are thus obtained in the form of a white powder, the characteristics of which are as follows: melting point=251° C., ¹H N.M.R. spectrum (300 MHz, d6-(CD₃)₂S, δ in ppm): at room temperature, a mixture of rotamers in the proportions 50/50 is observed. 1.47, 1.78 and from 2.00 to 2.50 (3 mts, respectively 1H, 1H and 2H, CH₂CH₂), from 3.25 to 3.65 (mt, 5H, CH₂ at 1, 1H of the CH₂ at 3, H at 4 and H at 9a), 3.75 and 3.77 (2 s, 3H in total, OCH₃), 4.10 and 4.25 (2 d, J=11.5 Hz, 1H in total, the other H of the CH₂ at 3), 6.40 (broad d, J=7.5 Hz, 1H, H at 8), 6.93 (dt, J=7.5 and 2 Hz, 1H, H at 7), from 6.90 to 7.65 (mt, 1H, H at 5, H at 6, aromatic H ortho, meta and para to the OCH₃ and aromatic H of the phenyl at 9).

EXAMPLE 28

From 3 g (9 mmol) of the methyl ester of (3aRS, 4SR, 9SR, 9aRS)-4,9-ethano-9-phenyl-2,3,3a,4,9,9a-hexahydro-1H-benzo[f]isoindole-3a-carboxylic acid, 2.32 g (10.8 mmol) of 2-bromophenylacetic acid, 2.07 g (10.8 mmol) of 1-ethyl-3-(3-dimethylaminopropyl)carbodiimide hydrochloride and 121 g (0.9 mmol) of hydroxybenzotriazole in solution of 100 cm³ of dichloromethane, after stirring for 18 hours at a temperature in the region of 20° C. and purifying the crude product obtained by flash chromatography on silica gel (70–230 mesh), elution being carried out with a cyclohexane/ethyl acetate (5/5 by volume) mixture, 286 mg (60%) of the methyl ester of (3aRS, 4SR, 9SR, 9aRS)-4,9-ethano-2-(2-bromophenyl)acetyl-9-phenyl-2,3,3a,4,9,9a-hexahydro-1H-benzo[f]isoindole-3a-carboxylic acid are obtained in the form of a white powder, the characteristics of which are as follows: melting point=128–130° C., mass spectrum (D.C.I.: NH3) M/Z=530 (MH⁺)

From 1 g (1.82 mmol) of the methyl ester of (3aRS, 4SR, 9SR, 9aRS)-4,9-ethano-2-(2-bromophenyl)-acetyl-9-phenyl-2,3,3a,4,9,9a-hexahydro-1H-benzo[f]isoindole-3a-carboxylic acid, heated at reflux for 4 hours in 36 cm³ of 1N sodium hydroxide and 36 cm³ of ethanol, after purifying by flash chromatography on silica gel (70–230 mesh), elution being carried out with a dichloromethane/methanol/acetic acid (95/4/1 by volume) mixture, 430 mg (44%) of (3aRS, 4SR, 9SR, 9aRS)-4,9-ethano-2-(2-bromophenyl)acetyl-9-phenyl-2,3,3a,4,9,9a-hexahydro-1H-benzo[f]isoindole-3a-carboxylic acid are obtained in the form of a white powder, the characteristics of which are as follows: melting point=167° C., mass spectrum (D.C.I.: NH3) M/Z=516 (M⁺)

EXAMPLE 29

200 mg (0.44 mmol) of (3aRS, 4SR, 9SR, 9aRS)-4,9-ethano-2-(2-hydroxyphenyl)acetyl-9-phenyl-2,3,3a,4,9,9a-hexahydro-1H-benzo[f]isoindole-3a-carboxylic acid, obtained under the conditions of Example 60 below, 106 mg (1.32 mmol) of pyridine and 11 mg (0.09 mmol) of 4-(dimethylamino)pyridine are dissolved in 30 cm³ of dichloromethane and then 225 mg (2.2 mmol) of acetic anhydride are added. After stirring for 18 hours at a temperature in the region of 20° C., the excess acetic anhydride is neutralized by addition of 1N aqueous sodium hydroxide. The organic phase, separated by settling, is washed successively with water, with a 0.1N hydrochloric acid solution and then with water, dried over magnesium sulphate and concentrated to dryness under reduced pressure. The residue obtained is purified by chromatography on a preparative silica plate, elution being carried out with a dichloromethane/methanol/acetic acid (95/4.5/0.5 by volume) mixture. 78 mg (36%) of (3aRS, 4SR, 9SR, 9aRS)-4,9-ethano-2-(2-acetoxyphenyl)acetyl-9-phenyl-2,3,3a,4,9,9a-hexahydro-1H-benzo[f]isoindole-3a-carboxylic acid are thus obtained in the form of a white powder, the characteristics of which are as follows: melting point=157–158° C., mass spectrum (E.I.) M/Z=496 (M$^+$)

EXAMPLE 30

From 901 mg (2.7 mmol) of the methyl ester of (3aRS, 4SR, 9SR, 9aRS)-4,9-ethano-9-phenyl-2,3,3a,4,9,9a-hexahydro-1H-benzo[f]isoindole-3a-carboxylic acid, 600 mg (3.3 mmol) of (2-methylthiophenyl)acetic acid, which can be obtained according to J. Organomet. Chem., 178, 800 (1979), 630 mg (3.3 mmol) of 1-ethyl-3-(3-dimethylaminopropyl)carbodiimide hydrochloride and 36 mg (0.27 mmol) of hydroxybenzotriazole in solution in 30 cm$^3$ of dichloromethane, after stirring for 18 hours at a temperature in the region of 20° C. and purifying the crude product obtained by flash chromatography on silica gel (70–230 mesh), elution being carried out with a cyclohexane/ethyl acetate (7/3 by volume) mixture, 1.25 g (92%) of the methyl ester of (3aRS, 4SR, 9SR, 9aRS)-4,9-ethano-2-(2-methylthiophenyl)acetyl-9-phenyl-2,3,3a,4,9,9a-hexahydro-1H-benzo[f]isoindole-3a-carboxylic acid are obtained in the form of a white powder, the characteristics of which are as follows: melting point=155° C., mass spectrum (D.C.I.: NH3) M/Z=498 (MH$^+$)

From 1.25 g (2.5 mmol) of the methyl ester of (3aRS, 4SR, 9SR, 9aRS)-4,9-ethano-2-(2-methylthiophenyl)acetyl-9-phenyl-2,3,3a,4,9,9 a-hexahydro-1H-benzo[f]isoindole-3a-carboxylic acid, heated at reflux for 4 hours in 31.5 cm$^3$ of 1N sodium hydroxide and 31.5 cm$^3$ of ethanol, 780 mg (64%) of (3aRS, 4SR, 9SR, 9aRS)-4,9-ethano-2-(2-methylthiophenyl)acetyl-9-phenyl-2,3,3a,4,9,9a-hexahydro-1H-benzo[f]isoindole-3a-carboxylic acid are obtained, after purification by crystallization from isopropyl ether, in the form of white crystals, the characteristics of which are as follows: melting point=237° C., mass spectrum (D.C.I.: NH3) M/Z=484 (MH$^+$)

EXAMPLE 31

774 mg (1.6 mmol) of (3aRS, 4SR, 9SR, 9aRS)-4,9-ethano-2-(2-methylthiophenyl)acetyl-9-phenyl-2,3,3a,4,9,9a-hexahydro-1H-benzo[f]isoindol-3a-carboxylic acid are resolved on a chiral silica column carrying (3,5-dinitrobenzyl)phenylalanine grafts, elution being carried out with a dichloromethane/isopropanol/n-heptane (85/10/5 by volume) mixture. On collecting the second fraction eluted (retention time=15.4 minutes), 330 mg of the dextrorotatory enantiomer of (3aRS, 4SR, 9SR, 9aRS)-4,9-ethano-2-(2-methylthiophenyl)acetyl-9-phenyl-2,3,3a,4,9,9a-hexahydro-1H-benzo[f]isoindole-3a-carboxylic acid, the dextrorotatory enantiomer, are obtained in the form of white crystals, the characteristics of which are as follows: melting point=133° C., optical rotation $[\alpha]_{365}^{20}$=+187.2±3 (c=0.5, dichloromethane), mass spectrum (D.C.I.: NH3) M/Z=484 (MH$^+$)

The chiral silica can be prepared in the following way:

948 g of aminopropyl silica (100 Å, 10 μm, NH$_2$, Macherey-Nagel) are suspended in 3 liters of dimethylformamide in a 6-liter three-necked flask. 180 g of the anhydride of N-(tert-butoxycarbonyl)-11-aminoundecanoic acid are added and the reaction mixture is stirred for 18 hours at a temperature in the region of 20° C. The silica is separated by filtration and washed successively with 2 times 2500 cm$^3$ of dichloromethane and then 2 times 2500 cm$^3$ of dimethylformamide. The silica, thus washed, is resuspended in 3 liters of dimethylformamide and 180 g of the anhydride of N-(tert-butoxycarbonyl)-11-aminoundecanoic acid are added and then the reaction mixture is stirred for 18 hours at a temperature in the region of 20° C. The silica is separated by filtration, washed successively with 2 times 2500 cm$^3$ of dichloromethane, 2 times 2500 cm$^3$ of tetrahydrofuran, 2 times 2500 cm$^3$ of methanol and 2 times 2500 cm$^3$ of diethyl ether and then dried under reduced pressure at a temperature in the region of 20° C. 971 g of silica, denoted by the term "BOC-C$_{11}$-C$_3$-silica", are thus obtained in the form of a white powder, the structure of which is confirmed by the infrared spectrum and the elemental analysis (found) of which is: C %=9.85, H % =2.05, N %=1.05.

971 g of "BOC-C$_{11}$-C$_3$-silica" silica are suspended in 2.5 liters of dichloromethane and 470 g of imidazole in a 6-liter three-necked flask. 850 cm$^3$ of dimethyloctylchlorosilane are added dropwise and the reaction mixture is stirred for 16 hours at a temperature in the region of 20° C. The solid obtained is separated by filtration and washed successively with 2 times 2.5 liters of dichloromethane, 2 times 2.5 liters of methanol, 2 times 2.5 liters of tetrahydrofuran, 2 times 2.5 liters of dichloromethane and 2 times 2.5 liters of diethyl ether and then dried under reduced pressure at a temperature in the region of 20° C. 1179 g of silica, denoted by the term "BOC-C$_{11}$-C$_3$-silica-O-Si(CH$_3$)$_2$(CH$_2$)$_7$CH$_3$", are thus obtained in the form of a white powder, the structure of which is confirmed by the infrared spectrum and the elemental analysis (found) of which is: C %=13.9, H %=2.83, N %=1.16.

1178 g of "BOC-C$_{11}$-C$_3$-silica-O-Si(CH$_3$)$_2$ (CH$_2$)$_7$CH$_3$" silica are suspended in 2500 cm$^3$ of a 5% by volume solution of trifluoroacetic acid in dichloromethane in a 6-liter three-necked flask. The reaction mixture is stirred at 20° C. The silica is separated by filtration and washed successively with 2 times 2.5 liters of dichloromethane, 2 times 2.5 liters of a dichloromethane/diisopropylethylamine (70/30 by volume) mixture, 2.5 liters of dichloromethane, 2 times 2.5 liters of tetrahydrofuran, 2 times 2 liters of methanol and 2 times 2 liters of diethyl ether and then dried under reduced pressure at a temperature in the region of 50° C. 1080.5 g of silica, denoted by the term "C$_{11}$-C$_3$-silica-O-Si(CH$_3$)$_2$(CH$_2$)$_7$CH$_3$", are thus obtained in the form of a white powder, the structure of which is confirmed by the infrared spectrum and the elemental analysis (found) of which is: C %=12.6, H %=2.44, N %=1.05.

1080 g of "C$_{11}$—C$_3$—(silica)—O—Si(CH$_3$)$_2$(CH$_2$),CH$_3$" silica are suspended in 2500 cm$^3$ of dimethylformamide, which has been dried over 4 Å molecular sieve, in a 6-liter, three-necked, round-bottomed flask. 108 g of N-(3,5-dinitrobenzoyl)-L-phenylalanine and 75 g of N-ethoxycarbonyl-2-ethoxy-1,2-dihydroquinoline are added. The reaction mixture is stirred overnight. The silica is separated by filtration on sintered glass and is then washed with 2 times 2500 cm$^3$ of dichloromethane, 2 times 2500 cm$^3$ of tetrahydrofuran, 2500 cm$^3$ of dimethylformamide and 2500 cm$^3$ of dichloromethane. The silica, thus washed, is resuspended in 2500 cm$^3$ of dimethylformamide. 108 g of N-(3,5-dinitrobenzoyl)-L-phenylalanine and 75 g of N-ethoxycarbonyl-2-ethoxy-1,2-dihydroquinoline are successively added and the reaction mixture is then stirred overnight at 20° C. The silica is separated by filtration on sintered glass and is washed successively with 2 times 2500 cm³ of dichloromethane, 2 times 2500 cm³ of tetrahydrofuran, 2 times 2500 cm³ of methanol and 2 times 2500 cm³ of ethyl ether. After drying at 60° C. under reduced pressure (20 mm of mercury, 2.7 kPa), 1093.6 g of silica, denoted by the term "DNB-L-Phe-$C_{11}$-$C_3$-(silica)-O-Si $(CH_3)_2(CH_2)_7CH_3$", are obtained in the form of a pale-yellow powder, the structure of which is confirmed by its infrared spectrum and the elemental analysis (found) of which is: C %=14.5, H %=2.4, N %=1.68.

519 g of "DNB-L-Phe-$C_{11}$-$C_3$-(silica)-O-Si($CH_3)_2(CH_2$) $_7CH_3$" silica are suspended in 3000 cm³ of dimethylformamide, dried over 4Å molecular sieve, in a 4-liter, three-necked, round-bottomed flask. 450 cm³ of trimethylsilylimidazole are added over 15 minutes and the reaction mixture is then stirred overnight. The silica is separated by filtration and is washed successively with 2 times 1500 cm³ of tetrahydrofuran, 2 times 1500 cm³ of methanol, 2 times 1500 cm³ of acetone and 2 times 1500 cm³ of dichloromethane. After drying at a temperature of 60° C. under reduced pressure (2.7 kPa), 519 g of silica, denoted by the term "DNB-L-Phe-$C_{11}$-$C_3$-(silica)-[O-Si $(CH_3)_2(CH_2)_7CH_3$]-[O-Si($CH_3)_3$]", are obtained in the form of a pale-yellow powder, the structure of which is confirmed by its infrared spectrum and the elemental analysis (found) of which is: C %=15.3, H %=1.8, N %=2.6.

The anhydride of N-(tert-butoxycarbonyl)-11 -aminoundecanoic acid can be prepared in the following way:

30.1 g of N-(tert-butoxycarbonyl)-11-aminoundecanoic acid are dissolved in 480 cm³ of ethyl acetate. This solution is cooled to 5° C. and then, while maintaining it at this temperature, a solution of 10.63 g of dicyclohexylcarbodiimide in 120 cm³ of ethyl acetate is added over 10 minutes. The reaction mixture is stirred for 1 hour at 5° C. and then for 16 hours at a temperature in the region of 20° C. The precipitate formed is separated by filtration and washed with 30 cm³ of ethyl acetate. The filtrate is concentrated to dryness under reduced pressure (20 mm of mercury, 2.7 kPa) at 30° C. The solid obtained is dried at 20° C. under reduced pressure (20 mm of mercury, 2.7 kPa). 31 g of the anhydride of N-(tert-butoxycarbonyl)-11-aminoundecanoic acid are thus obtained, with a yield in the region of 100%.

N-(tert-Butoxycarbonyl)-11-aminoundecanoic acid can be prepared in the following way:

160 g of 11-aminoundecanoic acid, 2 liters of dioxane, 1.3 liters of distilled water, 208 g of sodium carbonate and 173 g of di-tert-butyl dicarbonate are successively introduced into a 4-liter three-necked flask equipped with a mechanical stirrer and a reflux condenser. The reaction mixture is heated at boiling point for 16 hours. A clear solution is thus obtained. After cooling to 20° C., the reaction mixture is poured onto 800 g of ice and then acidified to pH=3–4 by addition of 4N hydrochloric acid. A white precipitate is thus obtained which is separated by filtration, washed with 300 cm³ of water and dried at 20° C. under reduced pressure (20 mm of mercury, 2.7 kPa). 232 g of N-(tert-butoxycarbonyl)-11-aminoundecanoic acid are thus obtained, with a yield of 95%, the melting point of which (68° C.) is in agreement with that which is given in J. Org. Chem., 41, 1350 (1976).

EXAMPLE 32

From 1 g (3 mmol) of the methyl ester of (3aRS, 4SR, 9SR, 9aRS)-4,9-ethano-9-phenyl-2,3,3a,4,9,9a-hexahydro-1H-benzo[f]isoindole-3a-acetic acid, 947 mg (3.6 mmol) of the hydrochloride of 2-(3-pyrrolidinylpropyl) oxyphenylacetic acid, which can be obtained according to European Patent EP-0,514,275, 690 mg (3.6 mmol) of 1-ethyl-3-(3-dimethylaminopropyl)carbodiimide hydrochloride and 40 mg (0.3 mmol) of hydroxybenzotriazole in solution in 20 cm³ of dichloromethane, after stirring for 18 hours at a temperature in the region of 20° C., a crude product is obtained which precipitates. The precipitate formed is filtered off and washed with water and then resuspended in 25 cm³ of water and 25 cm³ of ethyl acetate. The suspension is brought to pH=8 by addition of 1N sodium hydroxide. After separating the organic phase by settling, the aqueous phase is extracted with 2 times 20 cm³ of ethyl acetate. The combined organic phases are washed with water, dried over magnesium sulphate and concentrated to dryness under reduced pressure. 1.63 g (94%) of the methyl ester of (3aRS, 4SR, 9SR, 9aRS)-4,9-ethano-2-[2- (3-pyrrolidinylpropyl)oxyphenyl]acetyl-9-phenyl-2,3,3a,4, 9,9a-hexahydro-1H-benzo[f]isoindole-3a-carboxylic acid are thus obtained in the form of a white powder, the characteristics of which are as follows: melting point=118° C., mass spectrum (D.C.I.: NH3) M/Z=579 (MH⁺)

From 1.60 g (2.77 mmol) of the methyl ester of (3aRS, 4SR, 9SR, 9aRS)-4,9-ethano-2-[2-(3-pyrrolidinylpropyl) oxyphenyl]acetyl-9-phenyl-2,3,3a,4,9,9a-hexahydro-1H-benzo[f]isoindole-3a-acetic acid, heated at reflux for 4 hours in 55 cm³ of 1N sodium hydroxide and 55 cm³ of ethanol, a residue is obtained, after concentrating to dryness under reduced pressure, which residue is taken up in 10 cm³ of ice-cold water and 5 cm³ of 1N hydrochloric acid. The hydrochloride thus formed is extracted with 3 times 50 cm³ of dichloromethane. The combined organic phases are washed with 2 times 5 cm³ of ice-cold water, dried over magnesium sulphate and concentrated to dryness under reduced pressure. On recrystallizing from a dichloromethane/ethyl ether (1/1 by volume) mixture, 1.24 g (75%) of the hydrochloride of (3aRS, 4SR, 9SR, 9aRS)- 4,9-ethano-2-[2-(3-pyrrolidinylpropyl)oxyphenyl]-acetyl-9-phenyl-2,3,3a,4,9,9a-hexahydro-1H-benzo[f]isoindole-3a-carboxylic acid are obtained in the form of white crystals, the characteristics of which are as follows: melting point= 135° C., mass spectrum (D.C.I./NH₃) M/Z=565 (MH⁺)

EXAMPLE 33

From 1.67 g (5 mmol) of the methyl ester of (3aRS, 4SR, 9SR, 9aRS)-4,9-ethano-9-phenyl-2,3,3a,4,9,9a-hexahydro-1H-benzo[f]isoindole-3a-carboxylic acid, 1.08 g (6 mmol) of (R)-2-(2-methoxyphenyl)propanoic acid, which can be obtained according to European Patent EP-0,430,771, 1.15 g (6 mmol) of 1-ethyl-3-(3-dimethylaminopropyl)- carbodiimide hydrochloride and 68 mg (0.5 mmol) of hydroxybenzotriazole in solution in 20 cm³ of dichloromethane, a mixture of diastereoisomers is obtained after stirring for 18 hours at a temperature in the region of 20° C., which diastereoisomers are separated by high pressure liquid chromatography (9 bar) on 12 μm silica gel, elution being carried out with a cyclohexane/ethyl acetate (8/2 by volume) mixture. The following are thus successively obtained:

670 mg (27%) of the A diastereoisomer of the methyl ester of (3aRS, 4SR, 9SR, 9aRS)-4,9-ethano-2-(R)-2-(2- methoxyphenyl)propanoyl-9-phenyl- 2,3,3a,4,9,9a-hexahydro-1H-benzo[f]isoindole-3a-carboxylic acid in the form of a white powder, the characteristics of which are as follows: melting point=82° C., optical rotation $[\alpha]_{365}^{20}$=− 20.3±0.6 (c=0.5, dichloromethane), mass spectrum (E.I.) M/Z=495 (M⁺)

690 mg (30%) of the B diastereoisomer of the methyl ester of (3aRS, 4SR, 9SR, 9aRS)-4,9-ethano-2-(R)-2-(2-methoxyphenyl)propanoyl-9-phenyl-2,3,3a,4,9,9a-hexahydro-1H-benzo[f]isoindole-3a-carboxylic acid in the form of a white powder, the characteristics of which are as follows: melting point=162° C., optical rotation $[\alpha]_{365}^{20}$=−480.5±3.9 (c=0.5, dichloromethane).

The preparation is carried out as in Example 2, from 570 mg (1.15 mmol) of the A diastereoisomer of the methyl ester of (3aRS, 4SR, 9SR, 9aRS)-4,9-ethano-2-(R)-2-(2-methoxyphenyl)propanoyl-9-phenyl-2,3,3a,4,9,9a-hexahydro-1H-benzo[f]isoindole-3a-carboxylic acid, by heating at reflux for 18 hours in 14.4 cm³ of 0.1N sodium hydroxide and 14.4 cm³ of ethanol. After crystallizing from isopropyl ether, 410 mg (76%) of the A diastereoisomer of (3aRS, 4SR, 9SR, 9aRS)-4,9-ethano-2-(R)-2-(2-methoxyphenyl)-propanoyl-9-phenyl-2,3,3a,4,9,9a-hexahydro-1H-benzo[f]isoindole-3a-carboxylic acid are obtained in the form of white crystals, the characteristics of which are as follows: melting point=231° C., optical rotation $[\alpha]_{365}^{20}$=−28.4±0.7 (c=0.5, dichloromethane), mass spectrum (D.C.I.: NH3) M/Z=482 (MH⁺)

EXAMPLE 34

From 1.24 g (3.7 mmol) of the methyl ester of (3aRS, 4SR, 9SR, 9aRS)-4,9-ethano-9-phenyl-2,3,3a,4,9,9a-hexahydro-1H-benzo[f]isoindole-3a-carboxylic acid, 800 mg (4.44 mmol) of (S)-2-(2-methoxyphenyl)propanoic acid, which can be obtained according to European Patent EP-0,430,771, 850 mg (4.44 mmol) of 1-ethyl-3-(3-dimethylaminopropyl)carbodiimide hydrochloride and 50 mg (0.37 mmol) of hydroxybenzotriazole in solution in 20 cm³ of dichloromethane, the diastereoisomers are obtained after stirring for 18 hours at a temperature in the region of 20° C., which diastereoisomers are separated by high pressure liquid chromatography (15 bars) on 12 μm silica gel, elution being carried out with a cyclohexane/ethyl acetate (8/2 by volume) mixture. The following are thus successively obtained:

880 mg (48%) of the A diastereoisomer of the methyl ester of (3aRS, 4SR, 9SR, 9aRS)-4,9-ethano-2-(S)-2-(2-methoxyphenyl)propionyl-9-phenyl-2,3,3a,4,9,9a-hexahydro-1H-benzo[f]isoindole-3 a-carboxylic acid in the form of a white powder, the characteristics of which are as follows: melting point=78–80° C., optical rotation $[\alpha]^{36520}$=+19.7±0.7 (c=0.5, dichloromethane), mass spectrum (D.C.I.: NH3) M/Z=496 (MH⁺)

860 mg (47%) of the B diastereoisomer of the methyl ester of (3aRS, 4SR, 9SR, 9aRS)-4,9-ethano-2-(S)-2-(2-methoxyphenyl)propionyl-9-phenyl-2,3,3a,4,9,9a-hexahydro-1H-benzo[f]isoindole-3a-carboxylic acid in the form of a white powder, the characteristics of which are as follows: melting point=160–162° C., optical rotation $[\alpha]_{365}^{20}$=+478.3±4.1 (c=0.5, dichloromethane)

From 720 mg (1.45 mmol) of the B diastereoisomer of the methyl ester of (3aRS, 4SR, 9SR, 9aRS)-4,9-ethano-2-(S)-2-(2-methoxyphenyl)propionyl-9-phenyl-2,3,3a,4,9,9a-hexahydro-1H-benzo[f]isoindole-3a-carboxylic acid, heated at reflux for 18 hours in 18 cm³ of 0.1N sodium hydroxide and 18 cm³ of ethanol, 510 mg (76%) of the B diastereoisomer of (3aRS, 4SR, 9SR, 9aRS)-4,9-ethano-2-(S)-2-(2-methoxyphenyl)propionyl-9-phenyl-2,3,3a,4,9,9a-hexahydro-1H-benzo[f]isoindole-3a-carboxylic acid are obtained, after crystallization from isopropyl ether, in the form of white crystals, the characteristics of which are as follows: melting point=160° C., optical rotation $[\alpha]_{365}^{20}$=+ 448±4.5 (c=0.5, dichloromethane), mass spectrum (D.C.I.: NH3) M/Z=482 (MH⁺)

EXAMPLE 35

From 920 mg (2.8 mmol) of the methyl ester of (3aRS, 4SR, 9SR, 9aRS)-4,9-ethano-9-phenyl-2,3,3a,4,9,9a-hexahydro-1H-benzo[f]isoindole-3a-carboxylic acid, 854 mg (3.36 mmol) of 5-bromoindole-3-acetic acid, 644 mg (3.36 mmol) of 1-ethyl-3-(3-dimethylaminopropyl) carbodiimide hydrochloride and 40 mg (0.28 mmol) of hydroxybenzotriazole in solution in 100 cm³ of dichloromethane, crystals are obtained, after stirring for 18 hours at a temperature in the region of 20° C., which are separated by filtration and washed 2 times with 2 cm³ of ice-cold dichloromethane. 1.13 g (71%) of the methyl ester of (3aRS, 4SR, 9SR, 9aRS)-4,9-ethano-2-(5-bromo-3-indolyl)acetyl-9-phenyl-2,3,3a,4,9,9a-hexahydro-1H-benzo[f]isoindole-3a-carboxylic acid are thus obtained in the form of a white powder, the characteristics of which are as follows: melting point=230° C., mass spectrum (E.I.) M/Z=569 (M⁺)

From 600 mg (1.05 mmol) of the methyl ester of (3aRS, 4SR, 9SR, 9aRS)-4,9-ethano-(5-bromo-3-indolyl)acetyl-9-phenyl-2,3,3a,4,9,9a-hexahydro-1H-benzo[f]isoindole-3a-carboxylic acid, heated at reflux for 18 hours in 13.2 cm³ of 0.1N sodium hydroxide and 13.2 cm³ of ethanol, 150 mg (26%) of (3aRS, 4SR, 9SR, 9aRS)-4,9-ethano-2-(5-bromo-3-indolyl)acetyl-9-phenyl-2,3,3a,4,9,9a-hexahydro-1H-benzo [f]isoindole-3a-carboxylic acid are obtained, after recrystallization from ethyl acetate, in the form of white crystals, the characteristics of which are as follows: melting point=262° C., mass spectrum (E.I.) M/Z=555 (M⁺)

EXAMPLE 36

From 500 mg (1.5 mmol) of the methyl ester of (3aRS, 4SR, 9SR, 9aRS)-4,9-ethano-9-phenyl-2,3,3a,4,9,9a-hexahydro-1H-benzo[f]isoindole-3a-carboxylic acid, 328 mg (1.65 mmol) of (2,3-dimethoxyphenyl)acetic acid, prepared according to J. Org. Chem., 53, 548 (1949), 320 mg (1.65 mmol) of 1-ethyl-3-(3-dimethylaminopropyl) carbodiimide hydrochloride and 20 mg (0.15 mmol) of hydroxybenzotriazole in solution in 20 cm³ of dichloromethane, after stirring for 18 hours at a temperature in the region of 20° C. and purifying by flash chromatography on silica gel (70–230 mesh), elution being carried out with a cyclohexane/ethyl acetate (4/6 by volume) mixture, 640 mg (83%) of the methyl ester of (3aRS, 4SR, 9SR, 9aRS)-4,9-ethano-2-(2,3-dimethoxyphenyl)acetyl-9-phenyl-2,3,3a,4,9,9a-hexahydro-1H-benzo[f]isoindole-3a-carboxylic acid are obtained in the form of a white powder, the characteristics of which are as follows: melting point=196–197° C., mass spectrum (E.I.) M/Z=511 (M⁺)

From 320 mg (0.625 mmol) of the methyl ester of (3aRS, 4SR, 9SR, 9aRS)-4,9-ethano-2-(2,3-dimethoxyphenyl) acetyl-9-phenyl-2,3,3a,4,9,9a-hexahydro-1H-benzo[f] isoindole-3a-carboxylic acid, heated at reflux for 6 hours in 12.5 cm³ of 1N sodium hydroxide and 12.5 cm³ of ethanol, 150 mg (50%) of (3aRS, 4SR, 9SR, 9aRS)-4,9-ethano-2-(2, 3-dimethoxyphenyl)acetyl-9-phenyl-2,3,3a,4,9,9a-hexahydro-1H-benzo[f]isoindole-3a-carboxylic acid are obtained, after crystallization from isopropyl ether, in the form of white crystals, the characteristics of which are as follows: melting point=230° C., mass spectrum (E.I.) M/Z=497 (M⁺)

EXAMPLE 37

40 cm³ of concentrated hydrochloric acid are added very slowly, while maintaining the temperature below 5° C., to a suspension, cooled to 0° C., of 3.2 g (19 mmol) of (2-methoxyphenyl)acetic acid and 0.9 g (30 mmol) of p-formaldehyde. The temperature is allowed to rise to the region of 20° C. and the reaction mixture is stirred for 18 hours. The reaction mixture is poured onto 200 g of ice and is extracted 3 times with 200 cm³ of ethyl acetate. The combined organic phases are washed with water, dried over magnesium sulphate and concentrated to dryness under reduced pressure. After purification by flash chromatography on silica gel (70–230 mesh), elution being carried out with a cyclohexane/ethyl acetate mixture, 2.5 g (61%) of (2-methoxy-5-(chloromethyl)phenyl)acetic acid are obtained in the form of a pale-yellow powder, the characteristics of which are as follows: melting point=75–78° C., From 2 g (6 mmol) of the methyl ester of (3aRS, 4SR, 9SR, 9aRS)-4,9-ethano-9-phenyl-2,3,3a,4,9,9a-hexahydro-1H-benzo[f]isoindole-3a-carboxylic acid, 1.54 g (7.2 mmol) of (2-methoxy-5-(chloromethyl)phenyl)acetic acid, 1.38 g (7.2 mmol) of 1-ethyl-3-(3-dimethylaminopropyl) carbodiimide hydrochloride and 81 mg (0.6 mmol) of hydroxybenzotriazole in solution in 20 cm³ of dichloromethane, after stirring for 18 hours at a temperature in the region of 20° C. and purifying by flash chromatography on silica gel (70–230 mesh), elution being carried out with a cyclohexane/ethyl acetate (3/7 by volume) mixture, 2.92 g (92%) of the methyl ester of (3aRS, 4SR, 9SR, 9aRS)-4,9-ethano-2-(2-methoxy-5-(chloromethyl)phenyl) acetyl-9-phenyl-2,3,3a,4,9,9a-hexahydro-1H-benzo[f] isoindole-3a-carboxylic acid are obtained, which product contains a small amount of the 5-hydroxymethylated derivative.

960 mg (6 mmol) of potassium ethyl xanthate are added to a solution of 2.9 g (-5.4 mmol) of the methyl ester of (3aRS, 4SR, 9SR, 9aRS)-4,9-ethano-2-(2-methoxy-5-(chloromethyl)phenyl)acetyl-9-phenyl-2,3,3a,4,9,9a-hexahydro-1H-benzo[f]isoindole-3a-carboxylic acid obtained above in 25 cm³ of dimethylformamide and 25 cm³ of dioxane and the reaction mixture is then stirred for 24 hours at a temperature in the region of 20° C. After concentrating to dryness under reduced pressure, the residue is poured into 100 cm³ of ice-cold water. The light-beige precipitate formed is filtered off and then redissolved in 100 cm³ of ethyl acetate. The organic phase is washed with water until the aqueous wash liquors are perfectly clear. After drying over magnesium sulphate and concentrating to dryness under reduced pressure, 2.73 g (96%) of a powder are obtained, which powder essentially contains the methyl ester of (3aRS, 4SR, 9SR, 9aRS)-4,9-ethano-2-(2-methoxy-5-(mercaptomethyl)-phenyl)acetyl-9-phenyl-2,3,3a,4,9,9a-hexahydro-1H-benzo[f]isoindole-3a-carboxylic acid in the disulphide form.

From 2.72 g (2.6 mmol) of the disulphide of the methyl ester of (3aRS, 4SR, 9SR, 9aRS)-4,9-ethano-2-(2-methoxy-5-(mercaptomethyl)phenyl)acetyl-9-phenyl-2,3,3a,4,9,9a-hexahydro-1H-benzo[f]isoindole-3a-carboxylic acid obtained above, heated at reflux for 12 hours in 5.2 cm³ of 1N sodium hydroxide and 25 cm³ of ethanol, 180 mg (7%) of the disulphide of (3aRS, 4SR, 9SR, 9aRS)-4,9-ethano-2-(2-methoxy-5-(mercaptomethyl)-phenyl)acetyl-9-phenyl-2, 3,3a,4,9,9a-hexahydro-1H-benzo[f]isoindole-3a-carboxylic acid are obtained, after purifying by flash chromatography on silica gel (70–230 mesh), elution being carried out with a dichloromethane/ethyl acetate (1/1 by volume) mixture, and then chromatography on a preparative silica plate, elution being carried out with a dichloromethane/ethyl acetate/acetic acid (19/80/1 by volume) mixture, in the form of a white powder, the characteristics of which are as follows: melting point=140° C., infrared spectrum (as a KBr disc): main characteristic absorption bands, expressed in cm⁻¹, at 3065 and 3022 (aromatic n CH), 2952 and 2874 ($n_a$ and $n_{as}$ CH$_2$), 2387 (n CH of the OCH$_3$), 3000–2300 (n OH of the acid), 1732 (n C=O of the acid), 1646 and 1610 (n C=O of the amide), 1610, 1503, 1457 and 1444 (vibrations of the aromatic rings), 1254 (nas C—O of the ether), 1031 ($n_s$ C—O of the ether), 788 (g CH of the trisubstituted phenyl), 754 (g CH of the disubstituted phenyl), 701 (g CH of the monosubstituted phenyl).

EXAMPLE 38

13.5 cm³ (0.18 mol) of thionyl chloride are added slowly to a solution of 25 g (0.15 mol) of 2-methoxyphenylacetic acid in absolute ethanol. The mixture is stirred for 3 hours at reflux. After concentrating to dryness, 30 g (100%) of the ethyl ester of 2-methoxyphenylacetic acid are obtained in the form of a liquid, the characteristics of which are as follows: mass spectrum (E.I.) M/Z=180 (M⁺)

24 g (0.12 mol) of the ethyl ester of 2-methoxyphenylacetic acid, 5.2 g (0.17 mol) of paraformaldehyde, 0.68 g (1.84 mmol) of tetrabutylammonium iodide and 28.9 g (0.21 mol) of potassium carbonate are heated at reflux in toluene for 20 hours. After washing with distilled water, the solvent is removed by concentrating to dryness. 19 g (90%) of the ethyl ester of 2-(2-methoxyphenyl)acrylic acid are obtained in the form of a liquid, the characteristics of which are as follows: mass spectrum (E.I.) M/Z=192 (M⁺)

From 6 g (29 mmol) of the ethyl ester of 2-(2-methoxyphenyl)acrylic acid, heated at reflux in 58 cm³ (58 mmol) of 1N sodium hydroxide for 4 hours, 3.4 g (66%) of 2-(2-methoxyphenyl)acrylic acid are obtained, after acidification of the reaction mixture and filtration of the precipitate obtained, the characteristics of which are as follows: melting point=144° C., mass spectrum (E.I.) M/Z=178 (M⁺)

From 4.1 g (12.3 mmol) of the methyl ester of (3aRS, 4SR,9SR,9aRS)-4,9-ethano-9-phenyl- 2,3,3a,4,9,9a-hexahydro-1H-benzo[f]isoindole-3a-carboxylic acid, 2 g (11.2 mmol) of 2-(2-methoxyphenyl)acrylic acid, 2.36 g (12.3 mmol) of 1-ethyl-3-(3-dimethylamino-propyl) carbodiimide hydrochloride and 0.17 g (1.12 mmol) of hydroxybenzotriazole in dichloromethane, stirred for 24 hours at room temperature, 3.1 g (56%) of the methyl ester of (3aRS,4SR,9SR,9aRS)-4,9-ethano-2-[2-(2-methoxyphenyl)prop-2-en-1-oyl]-9-phenyl-2,3,3a,4,9,9a-hexahydro-1H-benzo[f]isoindole-3a-carboxylic acid are obtained, after purification by flash chromatography on silica gel (70–230 mesh), elution being carried out with a cyclohexane/ethyl acetate (60/40 by volume) mixture, in the form of a foam, the characteristics of which are as follows: melting point=80–85° C., mass spectrum (D.C.I.: NH3) M/Z=494 (MH⁺)

From 3 g (6.08 mmol) of the methyl ester of (3aRS,4SR, 9SR,9aRS)-4,9-ethano-2-[2-(2-methoxy-phenyl)prop-2-en-1-oyl]-9-phenyl-2,3,3a,4,9,9a-hexahydro-1H-benzo[f] isoindole-3a-carboxylic acid, heated at reflux in 7.5 cm³ (7.30 mmol) of 1N sodium hydroxide and ethanol, an oil is obtained after acidification of the reaction mixture with 1N hydrochloric acid, which salts out and which is extracted with ethyl acetate. The organic phase is washed with distilled water, dried and then concentrated to dryness under reduced pressure. 2.5 g (86%) of (3aRS,4SR,9SR,9aRS)-4, 9-ethano-2-[2-(2-methoxyphenyl)prop-2-en-1-oyl]-9-phenyl-2,3,3a,4,9,9a-hexahydro-1H-benzo[f]isoindole-3a-carboxylic acid are thus obtained, the characteristics of which are as follows: melting point 102–108° C., ¹H N.M.R. spectrum (250 MHz, d6-(CD₃)₂SO, at a temperature of 393 K, δ in ppm): 1.41, 1.66 and from 1.95 to 2.25 (3 mts, respectively 1H, 1H and 2H, CH₂CH₂), from 3.25 to 3.65 (mt, 3H, CH₂ at 1 and H at 9a), 3.43 (mt, 1H, H at 4), 3.60 and 4.05 (respectively d and broad d, J=12.5 Hz, each 1H, CH₂ at 3), 3.72 (s, 3H, OCH₃), 5.53 and 5.66 (2 broad s, each 1H, =CH₂), 6.42 (broad d, J=7.5 Hz, 1H, H at 8), 6.90 (broad t, J=7.5 Hz, 1H, aromatic H para to the OCH₃), from 7.00 to 7.10 (mt, 2H, aromatic H ortho to the OCH₃ and H at 7), from 7.10 to 7.60 (mt, 9H, aromatic H meta to the OCH₃, H at 5, H at 6 and aromatic H of the phenyl at 9).

EXAMPLE 39

5.2 g (10.84 mmol) of (3aRS,4SR,9SR,9aRS)-4,9-ethano-2-[2-(2-methoxyphenyl)prop-2-en-1-oyl]-9-phenyl-1,2,3,3a,9,9a-hexahydro-1H-benzo[f]isoindole-3a-carboxylic acid are resolved on a chiral silica column carrying (3,5-dinitrobenzyl)phenylalanine grafts, elution being carried out with a dichloromethane/isopropanol/n-heptane (85/10/5 by volume) mixture. On collecting the second fraction eluted (retention time=21.8 minutes), 2.25 g of (3aS,4R,9R,9aS)-4,9-ethano-2-[2-(2-methoxyphenyl)prop-2-en-1-oyl]-9-phenyl-1,2,3,3a,9,9a-hexahydro-1H-benzo[f]isoindole-3a-carboxylic acid, the dextrorotatory enantiomer, are obtained in the form of white crystals, the characteristics of which are as follows: melting point=155° C., optical rotation $[\alpha]_D^{20}$=+70.1±1.3 (c=0.5, dichloromethane), mass spectrum (D.C.I.: NH3) M/Z=480 (MH⁺)

EXAMPLE 40

8.25 cm³ (0.04 mol) of diisopropyl azodicarboxylate, 10.82 g (0.04 mol) of triphenylphosphine and 3.1 cm³ (0.04 mol) of isopropanol are added to a solution of 10 g (0.04 mol) of the benzyl ester of (2-hydroxyphenyl)acetic acid in tetrahydrofuran. The mixture is heated at reflux for 3 hours and then washed with distilled water. The organic phase is dried over magnesium sulphate. After filtering, the solvent is evaporated under reduced pressure. The residue obtained is chromatographed on silica gel, elution being carried out with a cyclohexane/ethyl acetate (99/01 by volume) mixture. 4.6 g (40%) of the benzyl ester of (2-isopropoxyphenyl) acetic acid are obtained in the form of a liquid, the characteristics of which are as follows: mass spectrum (E.I.) M/Z=284 (M⁺)

2.8 g (9.86 mmol) of the benzyl ester of (2-isopropoxyphenyl)acetic acid are heated at reflux in 100 cm³ (0.1 mol) of a 1N sodium hydroxide solution for 15 hours. After acidifying, the reaction mixture is extracted with ethyl acetate, dried over magnesium sulphate and then filtered. After evaporating the solvent under reduced pressure, 1.76 g (92%) of (2-isopropoxyphenyl)acetic acid are obtained in the form of an oil, the characteristics of which are as follows: mass spectrum (E.I.) M/Z=194 (M⁺)

From 1.5 g (4.5 mmol) of the methyl ester of (3aRS,4SR,9SR,9aRS)-4,9-ethano-9-phenyl-2,3,3,3a,4,9,9a-hexahydro-1H-benzo[f]isoindole-3a-carboxylic acid and 1 g (5.4 mmol) of (2-isopropoxyphenyl)acetic acid in dichloromethane, 0.97 g (42%) of the methyl ester of (3aRS,4SR,9SR,9aRS)-4,9-ethano-2-(2-isopropyl-oxyphenyl)acetyl-9-phenyl-2,3,3a,4,9,9a-hexahydro-1H-benzo[f]isoindole-3a-carboxylic acid is obtained in the form of a white solid, the characteristics of which are as follows: melting point=135–136° C., mass spectrum (D.C.I.: NH3) M/Z=510 (MH⁺)

From 970 mg (1.9 mmol) of the methyl ester of (3aRS,4SR,9SR,9aRS)-4,9-ethano-2-(2-isopropyl-oxyphenyl)acetyl-9-phenyl-2,3,3a,4,9,9a-hexahydro-1H-benzo[f]isoindole-3a-carboxylic acid in 3.8 cm³ (3.8 mmol) of a 1N sodium hydroxide solution, 891 mg (94%) of (3aRS,4SR,9SR,9aRS)-4,9-ethano-2-(2-isopropyl-oxyphenyl)acetyl-9-phenyl-2,3,3a,4,9,9a-hexahydro-1H-benzo[f]isoindole-3a-carboxylic acid are obtained, the characteristics of which are as follows: melting point=260° C., mass spectrum (L.S.I.M.S.) M/Z=496 (MH⁺)

EXAMPLE 41

1.22 g (42.7 mmol) of sodium hydride are added portionwise and under an argon atmosphere to a suspension of 9.4 g (42.7 mmol) of trimethylulphoxonium iodide in dimethyl sulphoxide. A solution of 8 g (38.8 mmol) of the ethyl ester of 2-(2-methoxyphenyl)acrylic acid in dimethyl sulphoxide is then added. The reaction mixture is stirred at a temperature in the region of 20° C. for 2 hours 30 minutes. After hydrolysis with distilled water, extraction with ethyl acetate, drying over magnesium sulphate and evaporation of the solvent under reduced pressure, the residue is chromatographed on silica gel (70–230 mesh), elution being carried out with a cyclohexane/ethyl acetate (95/5 by volume) mixture. 4.8 g (56%) of the ethyl ester of 1-(2-methoxyphenyl)cyclopropane-1-carboxylic acid are thus obtained in the form of an oil, the characteristics of which are as follows: mass spectrum (D.C.I.: NH3) M/Z=221 (MH⁺)

4.8 g (21.8 mmol) of the ethyl ester of 1-(2-methoxyphenyl)cyclopropane-1-carboxylic acid are heated at reflux in 33 cm³ (32.7 mmol) of a 1N sodium hydroxide solution for 4 hours. After acidification of the reaction mixture and filtration of the precipitate obtained, 3.2 g (76%) of 1-(2-methoxyphenyl)cyclo-propane-1-carboxylic acid are obtained, the characteristics of which are as follows: melting point=135° C., mass spectrum (E.I.) M/Z=192 (M⁺)

From 2.6 g (7.8 mmol) of the methyl ester of (3aRs,4SR,9SR,9aRS)-4,9-ethano-9-phenyl-2,3,3a,4,9,9a-hexahydro-1H-benzo[f]isoindole-3a-carboxylic acid and 1.5 g (7.8 mmol) of 1-(2-methoxyphenyl)cyclo-propane-1-carboxylic acid in dichloromethane, 2.5 g (63%) of the methyl ester of (3aRS,4SR,9SR,9aRS)-4,9-ethano-2-[1-(2-methoxyphenyl)-cyclopropan-1-oyl]-9-phenyl-2,3,3a,4,9,9a-hexahydro-1H-benzo[f]isoindole-3a-carboxylic acid are obtained in the form of a white solid, the characteristics of which are as follows: melting point=162° C., mass spectrum (E.I.) M/Z=507 (M⁺)

From 1 g (1.9 mmol) of the methyl ester of (3aRS,4SR,9SR,9aRS)-4,9-ethano-2-[1-(2-methoxy-phenyl)cyclopropan-1-oyl]-9-phenyl-2,3,3a,4,9,9a-hexahydro-1H-benzo[f]isoindole-3 a-carboxylic acid and 3.8 cm³ (3.8 mmol) of a 1N sodium hydroxide solution, 800 mg (82%) of (3aRS,4SR,9SR,9aRS)-4,9-ethano-2-[1-(2-methoxyphenyl)-cyclopropan-1-oyl]-9-phenyl-2,3,3a,4,9,9a-hexa-hydro-1H-benzo[f]isoindole-3a-carboxylic acid are obtained in the form of a white solid, the characteristics of which are as follows: melting point=146° C., mass spectrum (D.C.I.: NH₃) M/Z=494 (MH⁺)

EXAMPLE 42

A stream of ozone is sparged at −75° C. for 3 hours 30 minutes into a solution of 1 g (5.62 mmol) of 2-(2-methoxyphenyl)acrylic acid, obtained under the conditions described in Example 38, in dichloromethane. 1.66 cm³ (22.5 mmol) of dimethyl sulphide are added and stirring is continued, the temperature being allowed to rise to the region of 20° C. After concentrating the reaction mixture to dryness, 0.7 g (69%) of (2-methoxyphenyl)oxoacetic acid is obtained in the form of crystals, the characteristics of which are as follows: mass spectrum (E.I.) M/Z=180 (M⁺)

From 1.26 g (3.78 mmol) of the methyl ester of (3aRS, 4SR,9SR,9aRS)-4,9-ethano-9-phenyl-2,3,3a,4,9,9a-hexahydro-1H-benzo[f]isoindole-3a-carboxylic acid and 620 mg (3.44 mmol) of (2-methoxyphenyl)oxoacetic acid in dichloromethane, 1.3 g (76%) of the methyl ester of (3aRS, 4SR,9SR,9aRS)-4,9-ethano-2-[2-(2-methoxy-phenyl)-2-oxoacetyl]-9-phenyl-2,3,3a,4,9,9a-hexahydro-1H-benzo[f]isoindole-3a-carboxylic acid are obtained in the form of a white solid, the characteristics of which are as follows: melting point=156° C., mass spectrum (E.I.) M/Z=495 (M⁺)

From 500 mg (1.0 mmol) of the methyl ester of (3aRS, 4SR,9SR,9aRS)-4,9-ethano-2-[2-(2-methoxy-phenyl)-2-oxoacetyl]-9-phenyl-2,3,3a,4,9,9a-hexahydro-1H-benzo[f]isoindole-3a-carboxylic acid and 1.6 cm³ (1.6 mmol) of a 1N sodium hydroxide solution, 168 mg (35%) of (3aRS, 4SR,9SR,9aRS)-4,9-ethano-2-[2-(2-methoxyphenyl)-2-oxoacetyl]-9-phenyl-2,3,3a,4,9,9a-hexahydro-1H-benzo[f]isoindole-3a-carboxylic acid are obtained, the characteristics of which are as follows: melting point greater than 260° C., mass spectrum (D.C.I.: NH3) M/Z=482 (MH⁺)

EXAMPLE 43

2 g (6 mmol) of the methyl ester of (3aRS,4SR,9SR, 9aRS)-4,9-ethano-9-phenyl-2,3,3a,4,9,9a-hexahydro-1H-benzo[f]isoindole-3a-carboxylic acid are stirred for 1 hour, at a temperature in the region of 20° C., with 6 g (6 mmol) of di-t-butyl dicarbonate in solution in dichloromethane. After evaporating the solvent, the residue obtained is crystallized from petroleum ether. 2.3 g (87%) of the methyl ester of (3aRS,4SR,9SR,9aRS)-4,9-ethano-9-phenyl-2-(t-butoxycarbonyl)-2,3,3a,4,9,9a-hexahydro-1H-benzo[f]isoindole-3a-carboxylic acid are obtained in the form of crystals, the characteristics of which are as follows: melting point=142° C., mass spectrum (D.C.I.: NH3) M/Z=434 (MH⁺)

2.2 g (5 mmol) of the methyl ester of (3aRS,4SR,9SR, 9aRS)-4,9-ethano-9-phenyl-2-(t-butoxycarbonyl)-2,3,3a,4, 9,9a-hexahydro-1H-benzo[f]isoindole-3a-carboxylic acid and 1.29 g of iodine (5 mmol) in dichloromethane are stirred at a temperature in the region of 20° C. 2.29 g (5.25 mmol) of bistrifluoroacetoxyiodobenzene are added at 0° C. and the mixture is maintained at 0° C. for 1 hour. After hydrolysis with distilled water, extraction with ethyl acetate, drying over magnesium sulphate and evaporation of the solvent under reduced pressure, the residue obtained is chromatographed on silica gel (70–230 mesh), elution being carried out with a cyclohexane/ethyl acetate (90/10 by volume) mixture. 0.9 g (31.6%) of the methyl ester of (3aRS,4SR, 9SR,9aRS)-4,9-ethano-7-iodo-9-phenyl-2-(t-butoxycarbonyl)-2,3,3a,4,9,9a-hexahydro-1H-benzo[f]isoindole-3a-carboxylic acid is thus obtained in the form of a white foam, the characteristics of which are as follows: ¹H N.M.R. spectrum (250 MHz, d6-(CD₃)₂SO, at a temperature of 383 K, δ in ppm): 1.47 (s, 9H, C(CH₃)₃), 1.45, 1.78, from 2.00 to 2.20 (3 mts, respectively 1H, 1H and 2H, CH₂CH₂), from 3.20 to 3.40 (mt, 3H, CH₂ at 1 and H at 9a), 3.48 and 4.01 (2 d, J=12.5 Hz, each 1H, CH₂ at 3), 3.52 (mt, 1H, H at 4), 3.60 (s, 3H, COOCH₃), 6.72 (broad s, 1H, H at 8), 7.07 (broad d, J=7.5 Hz, 1H, H at 5), 7.45 (mt, 3H, aromatic H in the ortho and para positions of the phenyl at 9), 7.57 (mt, 3H, H at 6 and aromatic H in the meta positions of the phenyl at 9) and 0.8 g (28%) of the methyl ester of (3aRS,4SR,9SR,9aRS)-4,9-ethano-6-iodo-9-phenyl-2-(t-butoxycarbonyl)-2,3,3a,4,9,9a-hexahydro-1H-benzo[f] isoindole-3a-carboxylic acid is thus obtained in the form of a white foam, the characteristics of which are as follows: ¹H N.M.R. spectrum (400 MHz, d6-(CD₃)₂SO, at a temperature of 393 K, δ in ppm): 1.42 (s, 9H, C(CH₃)₃), 1.45, 1.73, from 2.00 to 2.20 (3 mts, respectively 1H, 1H and 2H, CH₂CH₂), from 3.20 to 3.60 (mt, 5H, CH₂ at 1, 1H of the CH₂ at 3, H at 4 and H at 9a), 3.58 (s, 3H, COOCH₃), 3.98 (d, J=12.5 Hz, 1H, the other H of the CH₂ at 3), 6.25 (broad d, J=7.5 Hz, 1H, H at 8), from 7.25 to 7.60 (mt, 7H, H at 5, H at 7 and aromatic H of the phenyl at 9).

A solution of 235 mg (0.42 mmol) of the methyl ester of (3aRS,4SR,9SR,9aRS)-4,9-ethano-7-iodo-9-phenyl-2-(t-butoxycarbonyl)-2,3,3a,4,9,9a-hexahydro-1H-benzo[f] isoindole-3a-carboxylic acid is stirred, at a temperature in the region of 20° C., for 24 hours with a large excess of a 5N solution of hydrochloric acid in methanol. After evaporating the solvent, 200 mg (100%) of the hydrochloride of the methyl ester of (3aRS,4SR,9SR,9aRS)-4,9-ethano-7-iodo-9-phenyl-2,3,3a,4,9,9a-hexahydro-1H-benzo[f]isoindole-3a-carboxylic acid are obtained in the form of a white solid, the characteristics of which are as follows: mass spectrum (D.C.I.: NH₃) M/Z=560 (MH⁺)

From 0.4 g (0.8 mmol) of the hydrochloride of the methyl ester of (3aRS,4SR,9SR,9aRS)-4,9-ethano-7-iodo-9-phenyl-2,3,3a,4,9,9a-hexahydro-1H-benzo[f]isoindole-3a-carboxylic acid and 0.16 g (0.96 mmol) of (2-methoxyphenyl)acetic acid in dichloromethane, 0.26 g (53%) of the methyl ester of (3aRS,4SR,9SR,9aRS)-4,9-ethano-7-iodo-2-(2-methoxyphenyl)acetyl-9-phenyl-2,3,3a, 4,9,9a-hexahydro-1H-benzo[f]isoindole-3a-carboxylic acid is obtained in the form of a white solid, the characteristics of which are as follows: mass spectrum (D.C.I.: NH₃) M/Z=608 (MH⁺)

From 260 mg (0.43 mmol) of the methyl ester of (3aRS, 4SR,9SR,9aRS)-4,9-ethano-7-iodo-2-(2-methoxyphenyl) acetyl-9-phenyl-2,3,3a,4,9,9a-hexahydro-1H-benzo[f] isoindole-3a-carboxylic acid and 0.42 cm³ (0.42 mmol) of a 1N sodium hydroxide solution, 200 mg (80%) of (3aRS, 4SR,9SR,9aRS)-4,9-ethano-7-iodo-2-(2-methoxyphenyl) acetyl-9-phenyl-2,3,3a,4,9,9a-hexahydro-1H-benzo[f] isoindole-3a-carboxylic acid are obtained, the characteristics of which are as follows: melting point greater than 260° C., ¹H N.M.R. spectrum (250 MHz, d6-(CD₃)₂SO with the addition of a few drops of d4-CD₃COOD, at a temperature of 383 K, δ in ppm): 1.40, 1.65 and from 1.80 to 2.20 (3 mts, respectively 1H, 1H and 2H, CH2CH2), from 3.30 to 3.65 (mt, 7H, CH2 at 1, COCH2Ar, 1H of the CH2 at 3, H at 4 and H at 9a), 3.72 (s, 3H, OCH3), 4.18 (d, J=12.5 Hz, 1H, the other H of the CH2 at 3), 6.72 (broad s, 1H, H at 8), from 6.85 to 7.00 (mt, 2H, aromatic H ortho and para to the OCH3), 7.07 (broad d, J=7.5 Hz, 1H, H at 5), from 7.15 to 7.35 (mt, 2H, aromatic H meta to the OCH3), from 7.35 to 7.70 (mt, 6H, H at 6 and aromatic H of the phenyl at 9).

EXAMPLE 44

66.5 mg (0.80 mmol) of methoxylamine hydrochloride, 133 mg (0.69 mmol) of 1-ethyl-3-(3-dimethylaminopropyl) carbodiimide hydrochloride, 10.6 mg (0.069 mmol) of hydroxybenzotriazole and 0.1 cm3 (0.80 mmol) of triethylamine are added to a solution of 332 mg (0.69 mmol) of the dextrorotatory enantiomer of (3aRS,4SR,9SR,9aRS)-4,9-ethano-2-[2-(2-methoxyphenyl)prop-2-en-1-oyl]-9-phenyl-2,3,3a,4,9,9a-hexahydro-1H-benzo[f]isoindole-3a-carboxylic acid in dichloromethane. The reaction mixture is stirred at a temperature in the region of 20° C. for 24 hours and washed with 0.1N hydrochloric acid and then with distilled water. After drying the organic phase and concentrating it to dryness, the crude product obtained in recrystallized from a mixture of pentane and methanol. 63 mg (18%) of (3aRS,4SR,9SR,9aRS)-N-methoxy-4,9-ethano-2-[2-(2-methoxyphenyl)prop-2-en-1-oyl]-9-phenyl-2,3,3a,4,9,9a-hexahydro-1H-benzo[f]isoindole-3a-carboxamide are thus obtained in the form of a white solid, the characteristics of which are as follows: melting point=160–162° C., mass spectrum (D.C.I.: NH$_3$) M/Z=509 (MH$^+$)

EXAMPLE 45

0.41 g (2.6 mmol) of O-benzylhydroxylamine hydrochloride, 0.48 g (2.6 mmol) of 1-ethyl-3-(3-dimethylaminopropyl)carbodiimide hydrochloride, 29 mg (0.214 mmol) of hydroxybenzotriazole and 0.36 cm$^3$ (2.6 mmol) of triethylamine are added to a solution of 1 g (2.1 mmol) of (3aRS,4SR,9SR,9aRS)-4,9-ethano-2-(2-methoxyphenylacetyl)-9-phenyl-2,3,3a,4,9,9a-hexahydro-1H-benzo[f]isoindole-3a-carboxylic acid in dichloromethane. On carrying out the preparation as in Example 44, 0.83 g (68%) of (3aRS,4SR,9SR,9aRS)-N-benzyloxy-4,9-ethano- 2-(2-methoxyphenylacetyl)-9-phenyl-2,3,3a,4,9,9a-hexahydro-1H-benzo[f]isoindole-3a-carboxamide is obtained in the form of a white solid, the characteristics of which are as follows: melting point=188° C., mass spectrum (D.C.I.: NH$_3$) M/Z=573 (MH$^+$)

EXAMPLE 46

A solution of 0.75 g (1.3 mmol) of (3aRS,4SR,9SR,9aRS)-N-benzyloxy-4,9-ethano-2-(2-methoxyphenylacetyl)-9-phenyl-2,3,3a,4,9,9a-hexahydro-1H-benzo[f]isoindole-3a-carboxamide, obtained under the conditions of Example 45, is stirred in the presence of 75 mg of 10% (w/w) palladium-on-charcoal in 40 cm$^3$ of ethanol with hydrogen at atmospheric pressure at 20° C. for 2 hours. After filtering off and then washing the catalyst with ethanol, the filtrate is concentrated to dryness under reduced pressure. After purifying by flash chromatography on silica gel (70–230 mesh), elution being carried out with a dichloromethane/methanol (90/10 by volume) mixture, and after recrystallizing from an isopropyl ether/ethanol mixture, 0.34 g (54%) of (3aRS,4SR,9SR,9aRS)-4,9-ethano-2-(2-methoxyphenylacetyl)-9-phenyl-2,3,3a,4,9,9a-hexahydro-1H-benzo[f]isoindole-3a-carbohydroxamic acid is obtained in the form of a white solid, the characteristics of which are as follows: melting point=234° C., mass spectrum (L.S.I.M.S.) M/Z=483 (MH$^+$)

EXAMPLE 47

3.7 g of (3aRS,4SR,9SR,9aRS)-4,9-ethano-2-[(2-methoxyphenyl)acetyl]-9-phenyl-2,3,3a,4,9,9a-hexahydro-1H-benzo[f]isoindole-3a-carboxylic acid, obtained under the conditions of Example 2, are resolved by chromatography on a chiral silica column carrying (3,5-dinitrobenzyl)phenylalanine grafts prepared under conditions analogous to those described in European Patent EP-0,625,153, elution being carried out with a dichloromethane/2-propanol/n-heptane (30/5/65 by volume) mixture. On concentrating the fractions containing the second product eluted, 1.4 g of 4,9-ethano-2-[(2-methoxyphenyl)acetyl]-9-phenyl-2,3,3a(S),4(R),9(R),9a(S)-hexahydro-1H-benzo[f]isoindole-3a-carboxylic acid are obtained, the characteristics of which are as follows: melting point=115° C., optical rotation $[\alpha]_D^{20}$=+55.1 (c=1, methanol), mass spectrum (DCI: NH$_3$): M/Z=468 (MH$^+$).

EXAMPLE 48

From 200 mg (0.43 mmol) of 4,9-ethano-2-(2-methoxyphenyl)acetyl-9-phenyl-2,3,3a(S),4(R),9(R),9a(S)-hexahydro- 1H-benzo[f]isoindole-3a-carboxylic acid, 62 mg (0.49 mmol) of the hydrochloride of methyl glycinate, 0.068 cm$^3$ (0.4 mmol) of triethylamine, 100 mg (0.52 mmol) of 1-ethyl-3-(3-dimethylaminopropyl)carbodiimide hydrochloride and 6 mg (0.04 mmol) of hydroxybenzotriazole in solution in 5 cm$^3$ of dichloromethane, after stirring for 20 hours at a temperature in the region of 20° C., separating by settling, washing the organic phase with 2 times 10 cm$^3$ of hydrochloric acid and 3 times 10 cm$^3$ of water, drying over magnesium sulphate and then concentrating under reduced pressure, 200 mg (87%) of the methyl ester of N-[4,9-ethano-2-(2-methoxy-phenyl)acetyl-9-phenyl-2,3,3a(S),4(R),9(R),9a(S)-hexahydro-1H-benzo[f]isoindol-3a-yl]carbonylglycine are obtained in the form of a yellow oil.

200 mg (0.37 mmol) of the methyl ester of N-[4,9-ethano-2-(2-methoxy-phenyl)acetyl-9-phenyl-2,3,3a(S),4(R),9(R),9a(S)-hexahydro-1H-benzo[f]isoindol-3a-yl]carbonylglycine are heated at reflux for 3 hours in 8.6 cm$^3$ of water, 18.6 cm$^3$ of ethanol and 0.22 cm$^3$ of 30% (w/w) sodium hydroxide. After removing the ethanol under reduced pressure, the solution is acidified with 0.3 cm$^3$ of hydrochloric acid (d=1.18) and then extracted with 2 times 30 cm$^3$ of dichloromethane. After separating by settling and washing with 3 times 10 cm$^3$ of water, the organic phase is dried over magnesium sulphate and then concentrated under reduced pressure. The residue obtained is purified by chromatography on a preparative silica gel plate, elution being carried out with a dichloromethane/methanol (80/20 by volume) mixture. 85 mg (45%) of N-[4,9-ethano-2-(2-methoxyphenyl)acetyl-9-phenyl-2,3,3a(S),4(R),9(R),9a(S)-hexahydro-1H-benzo[f]isoindol-3a-yl]carbonylglycine are thus obtained in the form of a white powder, the characteristics of which are as follows: melting point=150° C., optical rotation $[\alpha]_D^{20}$=+90 (c=1, methanol), mass spectrum (DCI: NH$_3$) : M/Z=525 (MH$^+$).

EXAMPLE 49

From 1.5 g (3.2 mmol) of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid, 0.7 g (3.85 mmol) of the hydrochloride of the tert-butyl ester of N-methylglycine, 0.5 cm$^3$ (3.85 mmol) of triethylamine, 0.74 g (3.85 mmol) of 1-ethyl-3-(3-dimethylaminopropyl)carbodiimide hydrochloride and 0.04 g (0.3 mmol) of hydroxybenzotriazole in solution in 40 cm$^3$ of dichloromethane, after stirring for 18 hours at a temperature in the region of 20° C., separating by settling, washing the organic phase with 2 times 100 cm$^3$ of water, drying over magnesium sulphate and then concentrating under reduced pressure, a residue is obtained which is purified by flash chromatography on silica gel (70–230 mesh), elution being carried out with a dichloromethane/methanol (99/1 by volume) mixture. 1 g (50%) of the tert-butyl ester of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonyl-N-methylglycine is thus obtained in the form of a white powder.

700 mg (1.18 mmol) of the tert-butyl ester of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonyl-N-methylglycine are heated at reflux for 4 hours in 12 cm$^3$ of ethanol and 17.5 cm$^3$ of 0.1 N sodium hydroxide. After removing the ethanol under reduced pressure, the solution is acidified with 1N hydrochloric acid and then extracted with 50 cm³ of ethyl acetate. After washing, by separating by settling, with 20 cm³ of water, the organic phase is dried over magnesium sulphate and then concentrated under reduced pressure. The residue obtained is triturated in 20 cm³ of petroleum ether. 455 mg (72%) of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonyl-N-methylglycine are thus obtained in the form of a white powder, the characteristics of which are as follows: melting point=198° C., mass spectrum (LSIMS): M/Z=539 (MH⁺).

EXAMPLE 50

From 880 mg (1.88 mmol) of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid, 316 mg (2.26 mmol) of the hydrochloride of methyl 3-aminopropanoate, 0.32 cm³ (2.26 mmol) of triethylamine, 440 mg (2.26 mmol) of 1-ethyl-3-(3-dimethylaminopropyl) carbodiimide hydrochloride and 25 mg (0.188 mmol) of hydroxybenzotriazole in solution in 30 cm³ of dichloromethane, after stirring for 18 hours at a temperature in the region of 20° C., washing, by separating by settling, the organic phase with 2 times 30 cm³ of water, drying the organic phase over magnesium sulphate and then concentrating the organic phase under reduced pressure, a solid residue is obtained which is purified by recrystallizing from ethyl acetate. 540 mg (50%) of methyl N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonyl-3-aminopropanoate are obtained in the form of a white powder.

540 mg (0.98 mmol) of methyl N-[(3aRS,4SR,9SR,9aRS)-4,9-ethano-2-(2-methoxyphenyl)acetyl-9-phenyl-2,3,3a,4,9,9a-hexahydro- 1H-benzo[f]isoindol-3a-yl]carbonyl-3-aminopropanoate are heated at reflux for 6 hours in 20 cm³ of ethanol and 9.8 cm³ of 0.1N sodium hydroxide. After removing the ethanol under reduced pressure, the solution is acidified with 1N hydrochloric acid and then extracted with 20 cm³ of ethyl acetate. After washing, by settling by separation, with 20 cm³ of water, the organic phase is dried over magnesium sulphate and then concentrated under reduced pressure. The solid obtained is purified by recrystallizing from ethanol. 230 mg (45%) of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonyl-3-aminopropanoic acid are thus obtained in the form of a white powder, the characteristics of which are as follows: melting point=150° C., mass spectrum (DCI: NH₃): M/Z=539 (MH⁺).

EXAMPLE 51

From 1.5 g (3.2 mmol) of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid, 0.76 g (3.85 mmol) of the hydrochloride of the methyl ester of L-methionine, 0.54 ml (3.85 mmol) of triethylamine, 0.74 g (3.85 mmol) of 1-ethyl-3-(3-dimethylaminopropyl) carbodiimide hydrochloride and 0.043 g (0.32 mmol) of hydroxybenzotriazole in solution in 50 cm³ of dichloromethane, after stirring for 18 hours at a temperature in the region of 20° C., washing, by settling by separation, the organic phase with 2 times 50 cm³ of water, drying the organic phase over magnesium sulphate and then concentrating the organic phase under reduced pressure, a residue is obtained which is purified by flash chromatography on silica gel (70–230 mesh), elution being carried out with a dichloromethane/methanol (99/1 by volume) mixture. 0.86 g (45%) of the methyl ester of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonyl-L-methionine is thus obtained in the form of a white powder, the characteristics of which are as follows: melting point=192° C.

0.86 g (1.4 mmol) of the methyl ester of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonyl-L-methionine are heated at reflux for 3 hours in 16 cm³ of ethanol and 21.5 cm³ of 0.1N sodium hydroxide. After removing the ethanol under reduced pressure, the solution is acidified with 1N hydrochloric acid and then extracted with 100 cm³ of ethyl acetate. After washing, by separating by settling, the organic phase with 50 cm³ of water, drying the organic phase over magnesium sulphate and then concentrating the organic phase under reduced pressure, 0.54 g (60%) of N-[(3aRS,4SR,9SR,9aRS)-4,9-ethano-2-(2-methoxy-phenyl)acetyl-9-phenyl-2,3,3a,4,9,9a-hexahydro-1H-benzo[f]isoindol-3a-yl]carbonyl-L-methionine is obtained in the form of a white powder, the characteristics of which are as follows: melting point=196° C., mass spectrum (DCI: NH₃) : M/Z=599 (MH⁺).

EXAMPLE 52

From 1.5 g (3.2 mmol) of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid, 1 g (3.8 mmol) of the hydrochloride of the methyl ester of S-benzylcysteine, 0.53 cm³ (3.8 mmol) of triethylamine, 0.73 g (3.8 mmol) of 1-ethyl-3-(3-dimethylaminopropyl) carbodiimide hydrochloride and 0.043 g (0.32 mmol) of hydroxybenzotriazole in solution in 60 cm³ of dichloromethane, after stirring for 18 hours at a temperature in the region of 20° C., washing, by separating by settling, the organic phase with 2 times 50 cm³ of water, drying the organic phase over magnesium sulphate and then concentrating the organic phase under reduced pressure, a residue is obtained which is purified by flash chromatography on silica gel (70–230 mesh), elution being carried out with ethyl acetate. 0.72 g (33%) of the methyl ester of N-[(3aRS,4SR,9SR,9aRS)-4,9-ethano-2-(2-methoxyphenyl)acetyl-9-phenyl-2,3,3a,4,9,9a-hexahydro-1H-benzo [f]isoindol-3a-yl]carbonyl-S-benzyl-L-cysteine is thus obtained in the form of a white foam.

0.5 g (0.74 mmol) of the methyl ester of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonyl-S-benzyl-L-cysteine are heated at reflux for 3 hours in 20 cm³ of ethanol and 12.5 cm³ of 0.1N sodium hydroxide. After removing the ethanol under reduced pressure, the solution is acidified with 1N hydrochloric acid and then extracted with 100 cm³ of ethyl acetate. After washing, by separating by settling, the organic phase with 50 cm³ of water, drying the organic phase over magnesium sulphate and then concentrating the organic phase under reduced pressure, a residue is obtained which is purified by flash chromatography on silica gel (70–230 mesh), elution being carried out with a dichloromethane/methanol/acetic acid (96/2/2 by volume) mixture. The solid product obtained is recrystallized from acetonitrile. 0.24 g (50%) of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonyl-S-benzyl-L-cysteine is thus obtained in the form of a white powder, the characteristics of which are as follows: melting point=190° C., mass spectrum (DCI: $NH_3$) : M/Z=661 ($MH^+$)

EXAMPLE 53

From 1.35 g (2.9 mmol) of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid, 1.31 g (3.47 mmol) of the methyl ester of S-triphenylmethyl-L-cysteine, which can be obtained according to Liebigs Ann. Chem., 1563 (1984), 0.66 g (3.47 mmol) of 1-ethyl-3-(3-dimethylaminopropyl)carbodiimide hydrochloride and 0.039 g (0.29 mmol) of hydroxybenzotriazole in solution in 100 cm$^3$ of dichloromethane, after stirring for 48 hours at a temperature in the region of 20° C., washing, by separating by settling, the organic phase with 2 times 75 cm$^3$ of water, drying the organic phase over magnesium sulphate and then concentrating the organic phase under reduced pressure, a residue is obtained which is purified by flash chromatography on silica gel (70–230 mesh), elution being carried out with a cyclohexane/ethyl acetate (80/20 by volume) mixture. 1.72 g (72%) of the methyl ester of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonyl-S-triphenylmethyl-L-cysteine are thus obtained in the form of a pale-yellow solid, the characteristics of which are as follows: mass spectrum (LSIMS): M/Z=827 ($MH^+$).

1.66 g (2 mmol) of the methyl ester of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonyl-S-triphenylmethyl-L-cysteine are heated at reflux for 5 hours in 50 cm$^3$ of methanol and 20 cm$^3$ of 0.1N sodium hydroxide. After removing the ethanol under reduced pressure, the solution is acidified with 1N hydrochloric acid, left stirring for 1 hour and then extracted with 50 cm$^3$ of ethyl acetate. After washing, by separating by settling, the organic phase with 2 times 30 cm$^3$ of water, drying the organic phase over magnesium sulphate and then concentrating the organic phase under reduced pressure, a residue is obtained which is washed with isopropyl ether and then purified by chromatography on Sephadex® gel, elution being carried out with methanol. 0.3g (20%) of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl] carbonyl-L-cysteine is thus obtained in the form of a pale-yellow solid, the characteristics of which are as follows: mass spectrum (LSIMS): M/Z=571 ($MH^+$).

EXAMPLE 54

From 750 mg (1.6 mmol) of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid, 130 mg (1.9 mmol) of methylamine hydrochloride, 0.27 ml (1.9 mmol) of triethylamine, 370 mg (1.9 mmol) of 1-ethyl-3-(3-dimethylaminopropyl)carbodiimide hydrochloride and 21.5 mg (0.16 mmol) of hydroxybenzotriazole in suspension in 25 cm$^3$ of dichloromethane, after stirring for 18 hours at a temperature in the region of 20° C. and the addition of 520 mg (3.9 mmol) of potassium carbonate, a suspension is obtained which is stirred for 24 hours at a temperature in the region of 20° C. After washing, by separating by settling, with 2 times 20 cm$^3$ of water, the organic phase is dried over magnesium sulphate and then concentrated under reduced pressure. The residue obtained is purified by flash chromatography on silica gel (70–230 mesh), elution being carried out with a dichloromethane/methanol (98/2 by volume) mixture. 540 mg (70%) of (3aRS,4SR,9SR,9aRS)-N-methyl-4,9-ethano-2-(2-methoxyphenyl)acetyl-9-phenyl-2,3,3a,4,9,9a-hexahydro-1H-benzo[f]isoindole-3a-carboxamide are thus obtained in the form of a white powder, the characteristics of which are as follows: melting point=216° C., mass spectrum (DCI: $NH_3$) : M/Z=481 ($MH^+$)

EXAMPLE 55

From 500 mg (1.1 mmol) of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid, 105 mg (1.3 mmol) of dimethylamine hydrochloride, 0.18 cm$^3$ (1.3 mmol) of triethylamine, 246 mg (1.3 mmol) of 1-ethyl-3-(3-dimethylaminopropyl)carbodiimide hydrochloride and 14.4 mg (0.11 mmol) of hydroxybenzotriazole in suspension in 30 cm$^3$ of dichloromethane, after stirring for 20 hours at a temperature in the region of 20° C. and washing, by separating by settling, the organic phase with 2 times 25 cm$^3$ of water, drying the organic phase over magnesium sulphate and then concentrating the organic phase under reduced pressure, a residue is obtained which is purified by flash chromatography on silica gel (70–230 mesh), elution being carried out with a dichloromethane/methanol (99/1 by volume) mixture. 225 mg (40%) of (3aRS,4SR,9SR,9aRS)-N,N-dimethyl-4,9-ethano-2-(2-methoxyphenyl)acetyl-9-phenyl-2,3,3a,4,9,9a-hexahydro-1H-benzo[f]isoindole-3a-carboxamide are thus obtained in the form of a white powder, the characteristics of which are as follows: melting point=138° C., mass spectrum (DCI: $NH_3$): M/Z=495 ($MH^+$).

EXAMPLE 56

From 467 mg (1 mmol) of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid, 96 mg (1.15 mmol) of O-methylhydroxylamine hydrochloride, 0.16 cm$^3$ (1.15 mmol) of triethylamine, 230 mg (1.2 mmol) of 1-ethyl-3-(3-dimethylaminopropyl)carbodiimide hydrochloride and 13 mg (0.1 mmol) of hydroxybenzotriazole in suspension in 8.5 cm$^3$ of dichloromethane, after stirring for 20 hours at a temperature in the region of 20° C., washing, by separating by settling, the organic phase with 2 times 10 cm$^3$ of water, drying the organic phase over sodium sulphate and then concentrating under reduced pressure, a residue is obtained which is purified by successive recrystallizations from ethanol and then toluene. 300 mg (60%) of (3aRS,4SR,9SR,9aRS)-N-methoxy-4,9-ethano-2-(2-methoxyphenyl)acetyl-9-phenyl-2,3,3a,4,9,9a-hexahydro-1H-benzo[f]isoindole-3a-carboxamide are thus obtained in the form of a white powder, the characteristics of which are as follows: melting point=217° C., mass spectrum (DCI: $NH_3$) : M/Z=497 ($MH^+$).

EXAMPLE 57

From 4.2 g (10 mmol) of (3aRS,4SR,SR,9aRS)-4,9-ethano-2-benzyl-9-phenyl- 2,3,3a,4,9,9a-hexahydro-1H-benzo[f]isoindole-3a-carboxylic acid, 1.41 g (11.5 mmol) of (R)-1-phenylethylamine, 2.25 g (11.5 mmol) of 1-ethyl-3-(3-dimethylaminopropyl)carbodiimide hydrochloride and 0.13 g (1 mmol) of hydroxybenzotriazole in solution in 100 cm$^3$ of dichloromethane, after stirring for 20 hours at a temperature in the region of 20° C., washing, by separating by settling, the organic phase with 2 times 25 cm$^3$ of water, drying the organic phase over magnesium sulphate and then concentrating the organic phase under reduced pressure, a residue is obtained which is purified by recrystallizing from isopropyl ether. 4.5 g (90%) of (3aRS,4SR,9SR,9aRS)-N-[(R)-1-phenylethyl]-4,9-ethano-2-benzyl-9-phenyl-2,3,3a,4,9,9a-hexahydro-1H-benzo[f]isoindole-3a-carboxamide are thus obtained in the form of a white powder, the characteristics of which are as follows: melting point=125° C., mass spectrum (DCI: $NH_3$) : M/Z=513 ($MH^+$)

From 4.5 g of (3aRS,4SR,9SR,9aRS)-N-[(R)-1-phenylethyl]-4,9-ethano-2-benzyl-9-phenyl-2,3,3a,4,9,9a-hexahydro-1H-benzo[f]isoindole-3a-carboxamide, 2.77 g of ammonium formate and 1.5 g of 5% (w/w) palladium-on-charcoal, in suspension in 75 cm³ of methanol, after heating at reflux for 3 hours, filtering off the catalyst after cooling and concentrating the methanol under reduced pressure, a residue is obtained which is dissolved in 100 cm³ of dichloromethane. After washing, by separating by settling, with 30 cm³ of 1 N sodium hydroxide and then with 3 times 30 cm³ of water, drying over magnesium sulphate and then concentrating under reduced pressure, 2.7 g (75%) of (3aRS,4SR,9SR,9aRS)-N-[(R)-1-phenylethyl]-4,9-ethano-9-phenyl-2,3,3a,4,9,9a-hexahydro-1H-benzo[f]isoindole-3a-carboxamide are obtained in the form of a foam.

From 2.7 g (6.4 mmol) of (3aRS,4SR,9SR,9aRS)-N-[(R)-1-phenylethyl]-4,9-ethano-9-phenyl-2,3,3a,4,9,9a-hexahydro-1H-benzo[f]isoindole-3a-carboxamide, 1.24 g (7.35 mmol) of (2-methoxyphenyl)acetic acid, 1.47 g (7.66 mmol) of 1-ethyl-3-(3-dimethylaminopropyl)carbodiimide hydrochloride and 0.086 g (0.64 mmol) of hydroxybenzotriazole in solution in 70 cm³ of dichloromethane, after stirring for 20 hours at a temperature in the region of 20° C., washing, by separating by settling, the organic phase with 2 times 25 cm³ of water, drying the organic phase over magnesium sulphate and then concentrating the organic phase under reduced pressure, a residue is obtained which is purified by flash chromatography on silica gel (70–230 mesh), elution being carried out with a dichloromethane/methanol (98/2 by volume) mixture. The diastereoisomers are separated by chromatography on a preparative silica gel plate, elution being carried out with a chloroform/ethyl acetate (60/40 by volume) mixture. After recrystallizing from ethanol, 1 g (33%) of N-[(R)-1-phenylethyl]-4,9-ethano-2-(2-methoxyphenyl)acetyl-9-phenyl-2,3,3a(S),4(R),9(R),9a(S)-hexahydro-1H-benzo[f]isoindole-3a-carboxamide is obtained in the form of a white powder, the characteristics of which are as follows: melting point=250° C., optical rotation $[a]_D^{20}$=+114 (c=0.5, chloroform), mass spectrum (DCI: $NH_3$) : M/Z=571 ($MH^+$)

EXAMPLE 58

From 750 mg (1.6 mmol) of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid, 0.094 cm³ (1.93 mmol) of hydrazine hydrate, 370 mg (1.93 mmol) of 1-ethyl-3-(3-dimethylaminopropyl)carbodiimide hydrochloride and 22 mg (0.16 mmol) of hydroxybenzotriazole in solution in 40 cm³ of dichloromethane, after stirring for 20 hours at a temperature in the region of 20° C., washing, by separating by settling, the organic phase with 2 times 25 cm³ of water, drying the organic phase over magnesium sulphate and then concentrating the organic phase under reduced pressure, a residue is obtained which is purified by flash chromatography on silica gel (70–230 mesh), elution being carried out with a dichloromethane/methanol (95/5 by volume) mixture. 385 mg (50%) of the hydrazide of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid are thus obtained in the form of a white powder, the characteristics of which are as follows: melting point=243° C., $^1$H N.M.R. spectrum (250 MHz, d6-$(CD_3)_2SO$, at a temperature of 393 K, δ in ppm): 1.37, 1.63 and from 1.85 to 2.15 (3 mts, respectively 1H, 1H and 2H, $CH_2CH_2$), from 3.25 to 3.70 (mt, 6H, $CH_2$ at 1, $COCH_2Ar$, 1H of the $CH_2$ at 3 and H at 9a), 3.60 (mt, 1H, H at 4), 3.70 (unresolved peak, 3H, $OCH_3$), 4.00 (unresolved peak, 2H, NH2), 4.22 (d, J=12.5 Hz, 1H, the other H of the $CH_2$ at 3), 6.39 (broad d, J=7.5 Hz, 1H, H at 8), 6.90 (broad t, J=7.5 Hz, 1H, aromatic H para to the $OCH_3$), 6.95 (broad d, J=7.5 Hz, 1H, aromatic H ortho to the $OCH_3$), 7.02 (dt, J=7.5 and 2 Hz, 1H, H at 7), from 7.05 to 7.30 (mt, 4H, H at 5, H at 6 and aromatic H meta to the $OCH_3$), from 7.30 to 7.55 (mt, 5H, aromatic H of the phenyl at 9), 8.70 (unresolved peak, 1H, CONH).

EXAMPLE 59

The methyl ester of (3aRS,4SR,9SR,9aRS)-4,9-ethano-2-(2-methoxyphenyl)propionyl-9-phenyl-2,3,3a,4,9,9a-hexahydro-1H-benzo[f]isoindole- 3a-carboxylic acid is prepared, under the conditions described in Example 1, in the form of white crystals, the characteristics of which are as follows: melting point=171° C., mass spectrum (DCI: $NH_3$) : M/Z=496 ($MH^+$).

(3aRS,4SR,9SR,9aRS)-4,9-Ethano-2-(2-methoxyphenyl) propionyl-9-phenyl-2,3,3a,4,9,9a-hexahydro-1H-benzo[f] isoindole-3a-carboxylic acid is prepared, under the conditions described in Example 2, in the form of white crystals, the characteristics of which are as follows: melting point= 202° C., $^1$H N.M.R. spectrum (250 MHz, d6-$(CD_3)_2SO$ with the addition of a few drops of d4-$CD_3COOD$, at a temperature of 403 K, δ in ppm): 1.39, 1.66, from 1.85 to 2.15 (3 mts, respectively 1H, 1H and 2H, CH2CH2), 2.50 (mt, 2H, COCH2), 2.85 (t, J=7.5 Hz, 2H, CH2Ar), from 3.25 to 3.50 (mt, 3H, CH2 at 1 and H at 9a), 3.48 (mt, 1H, H at 4), 3.58 and 4.10 (2 d, J=12.5 Hz, each 1H, CH2 at 3), 3.75 (s, 3H, OCH3), 6.42 (broad d, J=7.5 Hz, 1H, H at 8), 6.85 (broad t, J=7.5 Hz, 1H, aromatic H para to the OCH3), 6.92 (broad d, J=7.5 Hz, 1H, aromatic H ortho to the OCH3), 7.04 (dt, J=7.5 and 2 Hz, 1H, H at 7), from 7.10 to 7.25 (mt, 4H, H at 5, H at 6 and aromatic H meta to the OCH3), from 7.35 to 7.60 (mt, 5H, aromatic H of the phenyl at 9).

EXAMPLE 60

The methyl ester of (3aRS,4SR,9SR,9aRS)-4,9-ethano-2-(2-hydroxyphenyl)acetyl-9-phenyl-2,3,3a,4,9,9a-hexahydro-1H-benzo[f]isoindole-3a-carboxylic acid is prepared, under the conditions described in Example 1, in the form of beige crystals, the characteristics of which are as follows: melting point=205° C.

(3aRS,4SR,9SR,9aRS)-4,9-Ethano-2-(2-hydroxyphenyl) acetyl-9-phenyl-2,3,3a,4,9,9a-hexahydro-1H-benzo[f] isoindole-3a-carboxylic acid is prepared, under the conditions described in Example 2, in the form of white crystals, the characteristics of which are as follows: melting point= 151° C., mass spectrum (DCI; $NH_3$): M/Z=454 ($MH^+$).

EXAMPLE 61

The methyl ester of (3aRS,4SR,9SR,9aRS)-4,9-ethano-2-(2-chlorophenyl)acetyl-9-phenyl-2,3,3a,4,9,9a-hexahydro-1H-benzo[f]isoindole-3a-carboxylic acid is prepared, under the conditions described in Example 1, in the form of white crystals, the characteristics of which are as follows: melting point=147° C., mass spectrum (DCI; $NH_3$): M/Z=486 ($MH^+$).

(3aRS,4SR,9SR,9aRS)-4,9-Ethano-2-(2-chlorophenyl) acetyl- 9-phenyl-2,3,3a,4,9,9a-hexahydro-1H-benzo[f]

isoindole-3a-carboxylic acid is prepared, under the conditions described in Example 2, in the form of white crystals, the characteristics of which are as follows: melting point=223° C., mass spectrum (DCI; $NH_3$) : M/Z=472 ($MH^+$).

EXAMPLE 62

The methyl ester of (3aRS,4SR,9SR,9aRS)-4,9-ethano-2-(2-methylphenyl)acetyl-9-phenyl-2,3,3a,4,9,9a-hexahydro-1H-benzo[f]isoindole-3a-carboxylic acid is prepared, under the conditions described in Example 1, in the form of white crystals, the characteristics of which are as follows: melting point=130° C.

(3aRS,4SR,9SR,9aRS)-4,9-Ethano-2-(2-methylphenyl)acetyl-9-phenyl-2,3,3a,4,9,9a-hexahydro-1H-benzo[f]isoindole-3a-carboxylic acid is prepared, under the conditions described in Example 2, in the form of white crystals, the characteristics of which are as follows: melting point=188° C., mass spectrum (DCI; $NH_3$): M/Z=452 ($MH^+$).

EXAMPLE 63

The methyl ester of (3aRS,4SR,9SR,9aRS)-4,9-ethano-2-(2-fluorophenyl)acetyl- 9-phenyl-2,3,3a,4,9,9a-hexahydro-1H-benzo[f]isoindole-3a-carboxylic acid is prepared, under the conditions described in Example 1, in the form of white crystals, the characteristics of which are as follows: melting point=132° C., mass spectrum (DCI; $NH_3$): M/Z=470 ($MH^+$).

(3aRS,4SR,9SR,9aRS)-4,9-Ethano-2-(2-fluorophenyl)acetyl-9-phenyl-2,3,3a,4,9,9a-hexahydro-1H-benzo[f]isoindole-3a-carboxylic acid is prepared, under the conditions described in Example 2, in the form of white crystals, the characteristics of which are as follows: melting point=251° C., mass spectrum (LSIMS): M/Z=456 ($MH^+$).

EXAMPLE 64

280 cm³ of benzyl bromide are added, at a temperature in the region of 20° C., to a solution of 1 g of the methyl ester of (3aRS,4SR,9SR,9aRS)-4,9-ethano-2-(2-hydroxyphenyl)acetyl-9-phenyl-2,3,3a,4,9,9a-hexahydro-1H-benzo[f]isoindole-3a-carboxylic acid, prepared under the conditions described in Example 58, 650 mg of potassium carbonate and 8 mg of potassium iodide in 20 cm³ of acetonitrile. The reaction mixture is heated at a temperature in the region of 85° C. for 3 hours 30 minutes and it is then concentrated to dryness under reduced pressure (2.7 kPa) at 40° C. 100 cm³ of ethyl acetate and 50 cm³ of water are added. The organic phase is separated by settling, dried over magnesium sulphate, filtered and concentrated to dryness under reduced pressure (2.7 kPa) at 40° C. 1 g of a product is obtained which crystallizes from isopropyl ether. After filtering, 837 mg of the methyl ester of (3aRS,4SR,9SR,9aRS)-4,9-ethano-2-(2-benzyloxyphenyl)acetyl-9-phenyl-2,3,3a,4,9,9a-hexahydro-1H-benzo[f]isoindole-3a-carboxylic acid are obtained in the form of white crystals, the characteristics of which are as follows: melting point=146° C.

(3aRS,4SR,9SR,9aRS)-4,9-Ethano-2-(2-benzyloxyphenyl)acetyl-9-phenyl-2,3,3a,4,9,9a-hexahydro-1H-benzo[f]isoindole-3a-carboxylic acid is prepared, under the conditions described in Example 2, in the form of white crystals, the characteristics of which are as follows: melting point=229° C., mass spectrum (D.C.I.: $NH_3$) M/Z=544 ($MH^+$)

EXAMPLE 65

101 mg of Lawesson's reagent are added, at a temperature in the region of 20° C., to a solution of 243 mg of the methyl ester of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid, prepared under the conditions described in Example 1, in 10 cm³ of tetrahydrofuran. After stirring for 17 hours at a temperature in the region of 20° C., 20 cm³ of water are added. The aqueous phase is extracted with 3 times 50 cm³ of ethyl acetate. The organic phases are combined, washed with 30 cm³ of a saturated aqueous sodium chloride solution, dried over magnesium sulphate, filtered and concentrated to dryness under reduced pressure (2.7 kPa) at 40° C. 220 mg of a product are obtained, which product is purified by preparative chromatography on a silica plate with a thickness of 0.2 mm, elution being carried out with an ethyl acetate/cyclohexane (50/50 by volume) mixture. 18.2 mg of the methyl ester of (3aRS,4SR,9SR,9aRS)-4,9-ethano-2-(2-methoxyphenyl)thioacetyl-9-phenyl-2,3,3a,4,9,9a-hexahydro-1H-benzo[f]isoindole-3a-carboxylic acid are thus obtained in the form of white crystals, the characteristics of which are as follows: melting point=165° C.

(3aRS,4SR,9SR,9aRS)-4,9-Ethano-2-(2-methoxyphenyl)thioacetyl-9-phenyl-2,3,3a,4,9,9a-hexahydro-1H-benzo[f]isoindole-3a-carboxylic acid is prepared, under the conditions described in Example 2, in the form of white crystals, the characteristics of which are as follows: melting point=224° C., $^1$H N.M.R. spectrum (300 MHz, d6-$(CD_3)_2SO$ with the addition of a few drops of d4-$CD_3COOD$, δ in ppm): at room temperature, a mixture of rotamers in the proportions 65/35 is observed. 1.30 and from 1.60 to 2.00 (2 mts, 4H in total, CH2CH2), from 3.30 to 4.20 (mt, 10H, CH2 at 1, CSCH2Ar, 1H of the CH2 at 3, H at 4, H at 9a and OCH3), 4.48 and 4.70 (2 d, J=14 Hz, 1H in total, the other H of the CH2 at 3), 6.30 and 6.35 (2 broad d, J=7.5 Hz, 1H in total, H at 8), 6.85 to 7.55 (mt, 12H, H at 5, H at 6, H at 7, aromatic H ortho, meta and para to the OCH3 and aromatic H of the phenyl at 9).

EXAMPLE 66

400 cm3 of 2-methoxyphenyl isocyanate are added, at a temperature in the region of 20° C., to a solution of 1 g of the methyl ester of (3aRS,4SR,9SR,9aRS)-4,9-ethano-9-phenyl-2,3,3a,4,9,9a-hexahydro-1H-benzo[f]isoindole-3a-carboxylic acid, prepared under the conditions described in Example 1, and 10 mg of 4-dimethylaminopyridine in 15 cm³ of tetrahydrofuran. The reaction mixture is stirred at a temperature in the region of 20° C. for 1 hour and then 50 cm³ of ethyl acetate and 50 cm³ of water are added. The organic phase is separated by settling, washed with 30 cm³ of a saturated aqueous sodium chloride solution, dried over magnesium sulphate, filtered and concentrated to dryness under reduced pressure (2.7 kPa) at 40° C. 2.3 g of a product are obtained, which product crystallizes from isopropyl ether. After filtering, 1.2 g of the methyl ester of (3aRS,4SR,9SR,9aRS)-4,9-ethano-2-(2-methoxyphenyl)aminocarbonyl-9-phenyl-2,3,3a,4,9,9a-hexahydro-1H-benzo[f]isoindole-3a-carboxylic acid are obtained in the form of white crystals, the characteristics of which are as follows: melting point=156° C., mass spectrum (DCI; $NH_3$): M/Z=483 ($MH^+$).

(3aRS,4SR,9SR,9aRS)-4,9-Ethano-2-(2-methoxyphenyl)aminocarbonyl-9-phenyl-2,3,3a,4,9,9a-hexahydro-1H-benzo[f]isoindole-3a-carboxylic acid is prepared, under the conditions described in Example 2, in the form of white crystals, the characteristics of which are as follows: melting point greater than 260° C., $^1$H N.M.R. spectrum (300 MHz, d6-$(CD_3)_2SO$ with the addition of a few drops of d4-$CD_3COOD$, δ in ppm): 1.41, 1.69 and from 2.05 to 2.30

(3 mts, respectively 1H, 1H and 2H, CH2CH2), from 3.25 to 3.65 (mt, 5H, CH2 at 1, 1H of the CH2 at 3, H at 4 and H at 9a), 3.80 (s, 3H, OCH3), 4.20 (d, J=12 Hz, 1H, the other H of the CH2 at 3), 6.40 (broad d, J=7.5 Hz, 1H, H at 8), 6.90 (dt, J=7.5 and 2 Hz, 1H, H at 7), from 6.90 to 7.00 (mt, 2H, H at 5 and H at 6), 7.07 (broad t, J=7.5 Hz, 1H, aromatic H para to the OCH3), from 7.15 to 7.30 (mt, 2H, aromatic H ortho to the OCH3 and aromatic H para to the CONH), from 7.35 to 7.60 (mt, 5H, aromatic H of the phenyl at 9), 7.65 (broad d, J=7.5 Hz, 1H, aromatic H ortho to the CONH).

EXAMPLE 67

2 cm3 of thionyl chloride are added dropwise, at a temperature in the region of 20° C., to a suspension of 2 g of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid in 40 cm³ of dichloromethane. The reaction mixture is heated at a temperature in the region of 43° C. for 4 hours and then left stirring at a temperature in the region of 20° C. for 15 hours. The reaction mixture is then evaporated to dryness under reduced pressure (2.7 kPa). An oil is thus obtained which crystallizes from 20 cm³ of isopropyl ether. After filtering, 1.9 g of the chloride of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid are obtained in the form of white crystals, the characteristics of which are as follows: melting point: 140° C.

A solution of 1.4 g of the chloride of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid in 10 cm³ of dichloromethane is added, at a temperature in the region of 20° C., to a solution of 450 mg of t-butyl glycinate in 10 ml of a saturated aqueous sodium hydrogencarbonate solution. After stirring for 4 hours at a temperature in the region of 20° C., 50 cm³ of dichloromethane and 50 cm³ of water are added. The organic phase is separated by settling, washed with 50 cm³ of water and then dried over magnesium sulphate, filtered and concentrated to dryness under reduced pressure (2.7 kPa) at 40° C. 2.05 g of a white foam are thus obtained, which foam, triturated in an isopropyl ether/petroleum ether mixture, crystallizes to give, after filtering, 1.54 g of the t-butyl ester of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonylglycine in the form of white crystals, the characteristics of which are as follows: melting point=213° C., mass spectrum (DCI; NH₃): M/Z=581 (MH⁺).

2 cm³ of trifluoroacetic acid are added, at a temperature in the region of 20° C., to a solution of 1.5 g of the t-butyl ester of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonylglycine in 25 cm³ of dichloromethane. The reaction mixture is stirred overnight at a temperature in the region of 20° C. and then 20 cm³ of dichloromethane and 50 cm³ of water are added. The organic phase is separated by settling, washed with 50 cm³ of water and then dried over magnesium sulphate, filtered and concentrated to dryness under reduced pressure (2.7 kPa) at 40° C. 1.4 g are thus obtained of a product which is recrystallized from hot ethanol to give, after filtering, 350 mg of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonylglycine in the form of white crystals, the characteristics of which are as follows: melting point=262° C., ¹H N.M.R. spectrum (250 MHz, d6-(CD₃)₂SO, at a temperature of 383 K, δ in ppm): 1.39, 1.66, 1.85 and 2.10 (4 mts, each 1H, CH₂CH₂), from 3.25 to 3.75 (mt, 9H, CH₂ at 1, COCH₂Ar, NCH₂COO, 1H of the CH₂ at 3, H at 4 and H at 9a), 3.72 (s, 3H, OCH₃), 4.28 (d, J=13 Hz, 1H, the other H of the CH₂ at 3), 6.38 (broad d, J=7.5 Hz, 1H, H at 8), 6.90 (broad t, J=7.5 Hz, 1H, aromatic H para to the OCH₃), 6.95 (broad d, J=7.5 Hz, 1H, aromatic H ortho to the OCH₃), 7.02 (dt, J=7.5 and 2 Hz, 1H, H at 7), from 7.05 to 7.30 (mt, 4H, H at 5, H at 6 and aromatic H meta to the OCH₃), from 7.35 to 7.55 (mt, 5H, aromatic H of the phenyl at 9), 7.63 (unresolved peak, 1H, CONH).

EXAMPLE 68

11 mg of 1-hydroxybenzotriazole hydrate and 150 mg of 1-ethyl-3-(3-dimethylaminopropyl)carbodiimide hydrochloride are added, at a temperature in the region of 20° C., to a solution of 340 mg of (3aRS,4SR,9SR,9aRS)-4,9-ethano-2-(2-methoxyphenyl)acetyl-9-phenyl-2,3,3a,4,9,9a-hexahydro-1H-benzo[f]isoindole-3a-carboxylic acid, 91 mg of N,O-dimethylhydroxylamine chloride and 130 cm³ of triethylamine in 15 cm³ of dichloromethane. The reaction mixture is stirred overnight at a temperature in the region of 20° C. and then 50 cm³ of dichloromethane and 50 cm³ of water are added. The organic phase is separated by settling, dried over magnesium sulphate, filtered and concentrated to dryness under reduced pressure (2.7 kPa) at 40° C. 300 mg of a white solid are obtained, which solid, triturated in isopropyl ether, crystallizes to give, after filtering, 180 mg of (3aRS,4SR,9SR,9aRS)-N-methoxy-N-methyl-4,9-ethano-2-(2-methoxy-phenyl)acetyl-9-phenyl-2,3,3a,4,9,9a-hexahydro-1H-benzo[f]isoindole-3a-carboxamide in the form of white crystals, the characteristics of which are as follows: melting point=124° C., ¹H N.M.R. spectrum (300 MHz, d6-(CD₃)₂SO, d in ppm): at a temperature in the region of 20° C.; mixture of rotamers in the approximate proportions 1/1: from 1.20 to 1.95 (mts, 4H, CH₂CH₂), 3.02 (s, 3H, NCH₃), from 3.25 to 3.85 (mt, 7H, CH₂ at 1, COCH₂Ar, 1H of the CH₂ at 3, H at 4, H at 9a), 3.78 and 3.82 (2 s, 3H in total, NOCH₃), 4.26 (mt, 1H, the other H of the CH₂ at 3), 6.35 (broad d, J=7.5 Hz, 1H, H at 8), from 6.95 to 7.60 (mt, 13H, H at 5, H at 6, H at 7, aromatic H of the benzyl and aromatic H of the phenyl at 9).

EXAMPLE 69

The methyl ester of N-[(3aRS,4SR,9SR,9aRS)-4,9-ethano-2-(2-methoxyphenyl)acetyl-9-phenyl-2,3,3a,4,9,9a-hexahydro-1H-benzo[f]isoindol-3a-yl]carbonylglycine is prepared, under the conditions described in Example 66, in the form of white crystals, the characteristics of which are as follows: melting point=227° C., mass spectrum (D.C.I.: NH₃) M/Z=539 (MH⁺)

EXAMPLE 70

4 cm³ of a SM solution, prepared at the time of use, of sodium methoxide in methanol and 87 mg (0.97 mmol) of cupric chloride are added, under an argon atmosphere, to a solution of 1.1 g (1.97 mmol) of the methyl ester of (3aRS,4SR,9SR,9aRS)-4,9-ethano-7-iodo-9-phenyl-2-(t-butoxycarbonyl)-2,3,3a,4,9,9a-hexahydro-1H-benzo[f]isoindole-3a-carboxylic acid, obtained as in Example 43, in dimethylformamide. After stirring for 1 hour 30 minutes at 60° C. and then for 20 hours at a temperature in the region of 20° C., excess ammonium chloride is added until a strong blue colouring develops, the reaction mixture is then stirred for 1 hour and the methanol is evaporated under reduced pressure. The residue is taken up in water and ethyl acetate. After separation by settling, washing with water to neutrality, drying over magnesium sulphate and concentrating the solvent under reduced pressure, the oily brown residue is purified by flash chromatography on silica gel (230–400 mesh), elution being carried out with a mixture of dichloromethane and methanol (99/1 by volume). 0.7 g (79.5%) of the methyl ester of (3aRS,4SR,9SR,9aRS)-4,9-ethano-7-methoxy-9-phenyl-2-(t-butoxycarbonyl)-2,3,3a,4,9,9a-hexahydro-1H-benzo[f]isoindole-3a-carboxylic acid is thus obtained in the form of an oil which partially crystallizes, the characteristics of which are as follows: $^1$H N.M.R. spectrum (400 MHz, d6-(CD$_3$)$_2$SO, at a temperature of 383° K., δ in ppm): 1.45 (s, 9H, OC(CH$_3$)$_3$), 1.45, 1.75 and from 2.00 to 2.20 (3 mts, respectively 1H, 1H and 2H, CH$_2$CH$_2$), from 3.20 to 3.35 (mt, 3H, CH$_2$ at 1 and H at 9a), 3.45 (mt, 1H, H at 4), 3.45 and 3.98 (2 d, J=12.5 Hz, each 1H, CH$_2$ at 3), 3.55 (s, 3H, COOCH$_3$), 3.60 (s, 3H, OCH$_3$), 6.00 (d, J=1 Hz, 1H, H at 8), 6.75 (dd, J=8 and 1 Hz, 1H, H at 6), 7.09 (d, J=8 Hz, 1H, H at 5), 7.42 (broad t, J=7.5 Hz, 1H, aromatic H in the para position of the phenyl at 9), 7.45 (broad d, J=7.5 Hz, 2H, aromatic H in the ortho positions of the phenyl at 9), 7.53 (broad t, J=7.5 Hz, 2H, aromatic H in the para positions of the phenyl at 9).

From 0.58 g (1.20 mmol) of the methyl ester of (3aRS,4SR,9SR,9aRS)-4,9-ethano-7-methoxy-9-phenyl-2-(t-butoxycarbonyl)-2,3,3a,4,9,9a-hexahydro-1H-benzo[f]isoindole-3a-carboxylic acid in a large excess of methanolic hydrochloric acid, 0.49 g (98%) of the hydrochloride of the methyl ester of (3aRS,4SR,9SR,9aRS)-4,9-ethano-7-methoxy-9-phenyl-2,3,3a,4,9,9a-hexahydro-1H-benzo[f]isoindole-3a-carboxylic acid is obtained in the form of a white powder, the characteristics of which are as follows: melting point: greater than 260° C., mass spectrum (D.C.I.: NH$_3$) M/Z=363 (MH$^+$).

From 0.79 g (1.97 mmol) of the hydrochloride of the methyl ester of (3aRS,4SR,9SR,9aRS)-4,9-ethano-7-methoxy-9-phenyl-2,3,3a,4,9,9a-hexahydro-1H-benzo[f]isoindole-3a-carboxylic acid and 0.39 g (2.37 mmol) of 2-methoxyphenylacetic acid, in the presence of 0.2 g (1.97 mmol) of triethylamine, 0.45 g (2.37 mmol) of 1-ethyl-3-(3-dimethylaminopropyl)carbodiimide hydrochloride and 26 mg (0.2 mmol) of hydroxybenzotriazole, in solution in 20 cm$^3$ of dichloromethane, 147 mg (15%) of the methyl ester of (3aRS,4SR,9SR,9aRS)-4,9-ethano-7-methoxy-2-(2-methoxyphenyl)acetyl-9-phenyl-2,3,,3a,4,9,9a-hexahydro1H-benzo[f]isoindole-3a-carboxylic acid are obtained, after purification by flash chromatography on silica gel (230–400 mesh), elution being carried out with a mixture of dichloromethane and methanol (98/2 by volume), followed by recrystallization from 50% aqueous methanol, in the form of a white powder, the characteristics of which are as follows: melting point=146° C., mass spectrum (D.C.I.: NH$_3$) M/Z=511 (MH$^+$).

From 0.49 g (0.96 mmol) of the methyl ester of (3aRS,4SR,9SR,9aRS)-4,9-ethano-7-methoxy-2-(2-methoxyphenyl)acetyl-9-phenyl-2,3,3a,4,9,9a-hexahydro-1H-benzo[f]isoindole-3a-carboxylic acid and 1 cm$^3$ of 1N sodium hydroxide in 30 cm$^3$ of ethanol, 165 mg (35%) of (3aRS,4SR,9SR,9aRS)-4,9-ethano-7-methoxy-2-(2-methoxy-phenyl)acetyl-9-phenyl-2,3,3a,4,9,9a-hexahydro-1H-benzo[f]isoindole-3a-carboxylic acid are obtained, after purification by recrystallization from 80% aqueous ethanol, in the form of a white powder, the characteristics of which are as follows: melting point=226° C., $^1$H N.M.R. spectrum (300 MHz, d6-(CD$_3$)$_2$SO, δ in ppm), at a temperature of 393° K., a 50/50 mixture of two rotamers is observed: from 1.30 to 2.30 (mts, 4H in total, CH$_2$CH$_2$), from 3.10 to 3.90 (mt, 7H, CH$_2$ at 1, NCOCH$_2$, 1H of the CH$_2$ at 3, H at 4 and H at 9a), 3.52, 3.55, 3.60 and 3.80 (4 s, 6H in total, ArOCH$_3$), 4.12 and 4.22 (2 d, J=12.5 Hz, 1H in total, the other H of the CH$_2$ at 3), 5.90 and 5.92 (2 d, J=1 Hz, 1H in total, H at 8), 6.75 (mt, 1H, H at 6), from 6.90 to 7.60 (mt, 10H, aromatic H).

EXAMPLE 71

From 150 mg (0.312 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 40 mg (0.375 mmol) of benzylamine, 72 mg (0.375 mmol) of 1-ethyl-3-(3-dimethylaminopropyl)carbodiimide hydrochloride and 4.2 mg (0.03 mmol) of hydroxybenzotriazole in solution in 10 cm$^3$ of dichloromethane, after stirring for 18 hours at a temperature in the region of 20° C. and chromatographing the crude product obtained on a preparative silica plate, elution being carried out with a mixture of cyclohexane and ethyl acetate (50/50 by volume), 160 mg (94%) of (3aS,4R,9R,9aS)-N-[benzyl]-[4,9-ethano-2-(2-methoxyphenyl)-2-methylenylacetyl]-9-phenyl-2,3,3a,4,9,9a-hexahydro-1H-benzo[f]isoindole-3a-carboxamide are obtained in the form of a white powder, the characteristics of which are as follows: melting point=235° C., mass spectrum (E.I.) M/Z=568 (M$^+$).

EXAMPLE 72

From 300 mg (0.625 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 151 mg (0.75 mmol) of the hydrochloride of the methyl ester of (S)-phenylglycine, 144 mg (0.75 mmol) of 1-ethyl-3-(3-dimethylaminopropyl)carbodiimide hydrochloride, 7 mg (0.065 mmol) of hydroxybenzotriazole and 76 mg (0.75 mmol) of triethylamine in solution in 10 cm$^3$ of dichloromethane, after stirring for 18 hours at a temperature in the region of 20° C. and chromatographing the crude product obtained on a preparative silica plate, elution being carried out with a mixture of cyclohexane and ethyl acetate (60/40 by volume), 230 mg (59%) of N-[(S)-methyl phenylglycinoyl)]-[(3aS,4R,9R,9aS)-4,9-ethano-2-(2-methoxyphenyl)-2-methylenylacetyl]-9-phenyl-2,3,3a,4,9,9a-hexahydro-1H-benzo[f]isoindole-3a-carboxamide are obtained in the form of a white powder, the characteristics of which are as follows: melting point=214–215° C., mass spectrum (E.I.) M/Z=626 (M$^+$).

EXAMPLE 73

0.2 cm$^3$ (0.67 mmol) of tri(n-butyl)vinylstannane and 50 mg (0.05 mmol) of tetrakis(triphenylphosphine)palladium are successively added, under an argon atmosphere, to a solution of 0.3 g (0.53 mmol) of the methyl ester of (3aRS,4SR,9SR,9aRS)-4,9-ethano-7-iodo-9-phenyl-2-(t-butoxycarbonyl)-2,3,3a,4,9,9a-hexahydro-1H-benzo[f]isoindole-3a-carboxylic acid, obtained as in Example 43, in 10 cm$^3$ of dimethylformamide. After stirring for 3 hours at 90° C. and then for 20 hours at a temperature in the region of 20° C., 50 cm$^3$ of a 10% aqueous ammonia solution and 50 cm$^3$ of dichloromethane are added and the reaction mixture is stirred vigorously for 30 minutes. After separating by settling, washing with water to neutrality, drying over magnesium sulphate and concentrating the solvent under reduced pressure, the black oily residue is purified by flash chromatography on silica gel (230–400 mesh), elution being carried out with a gradient of mixtures of cyclohexane and ethyl acetate (from 99/1 to 90/10 by volume). 0.1 g (40.5%)

of the methyl ester of (3aRS,4SR,9SR,9aRS)-4,9-ethano-9-phenyl-2-(t-butoxycarbonyl)-7-vinyl-2,3,3a,4,9,9a-hexahydro-1H-benzo[f]isoindole-3a-carboxylic acid is thus obtained in the form of a colourless oil, the characteristics of which are as follows: $^1$H N.M.R. spectrum (400 MHz, d6-(CD$_3$)$_2$SO, δ in ppm): 1.45 (s, 9H, C(CH$_3$)$_3$), 1.46, 1.75 and from 2.05 to 2.20 (3 mts, respectively 1H, 1H and 2H, CH$_2$CH$_2$), from 3.20 to 3.40 (mt, 3H, CH$_2$ at 1 and H at 9a), 3.47 and 4.00 (2d, J=12.5 Hz, each 1H, CH$_2$ at 3), 3.50 (mt, 1H, H at 4), 3.58 (s, 3H, COOCH$_3$), 5.10 (broad d, J=11 Hz, 1H, H in the cis position of the =CH$_2$), 5.45 (broad d, J=17 Hz, 1H, H in the trans position of the =CH$_2$), 6.49 (d, J=1 Hz, 1H, H at 8), 6.57 (dd, J=17 and 11 Hz, 1H, ArCH=), 7.17 (d, J=8 Hz, 1H, H at 5), 7.26 (dd, J=8 and 1 Hz, 1H, H at 6), from 7.35 to 7.50 (mt, 3H, aromatic H in the ortho and para positions for the phenyl at 9), 7.56 (broad t, J=8 Hz, 2H, aromatic H in the meta positions for the phenyl at 9).

From 0.7 g (1.50 mmol) of the methyl ester of (3aRS,4SR,9SR,9aRS)-4,9-ethano-9-phenyl-2-(t-butoxycarbonyl)-7-vinyl-2,3,3a,4,9,9a-hexahydro-1H-benzo[f]isoindole-3a-carboxylic acid in a large excess of methanolic hydrochloric acid, 0.44 g (73%) of the hydrochloride of the methyl ester of (3aRS,4SR,9SR,9aRS)-4,9-ethano-9-phenyl-7-vinyl-2,3,3a,4,9,9a-hexahydro-1H-benzo[f]isoindole-3a-carboxylic acid is obtained in the form of a white powder, the characteristics of which are as follows: $^1$H N.M.R. spectrum (300 MHz, d6-(CD$_3$)$_2$SO, δ in ppm): 1.48, 1.82 and from 2.15 to 2.40 (3 mts, respectively 1H, 1H and 2H, CH$_2$CH$_2$), from 2.80 to 3.80 (mt, 6H, CH$_2$ at 1, CH$_2$ at 3, H at 4 and H at 9a), 3.55 (s, 3H, COOCH$_3$), 5.10 (broad d, J=11 Hz, 1H, H in the cis position of the =CH$_2$), 5.45 (broad d, J=17 Hz, 1H, H in the trans position of the =CH$_2$), 6.42 (d, J=1 Hz, 1H, H at 8), 6.55 (dd, J=17 and 11 Hz, 1H, ArCH=), 7.15 (d, J=8 Hz, 1H, H at 5), 7.29 (dd, J=8 and 1 Hz, 1H, H at 6), from 7.35 to 7.50 (mt, 3H, aromatic H in the ortho and para positions for the phenyl at 9), 7.56 (broad t, J=8 Hz, 2H, aromatic H in the meta positions for the phenyl at 9).

From 0.51 g (1.30 mmol) of the hydrochloride of the methyl ester of (3aRS,4SR,9SR,9aRS)-4,9-ethano-9-phenyl-7-vinyl-2,3,3a,4,9,9a-hexahydro-1H-benzo[f]isoindole-3a-carboxylic acid and 0.26 g (1.50 mmol) of 2-methoxyphenylacetic acid, in the presence of 0.132 g (1.30 mmol) of triethylamine, 0.30 g (1.50 mmol) of 1-ethyl-3-(3-dimethylaminopropyl)carbodiimide hydrochloride and 20 mg (0.13 mmol) of hydroxybenzotriazole in solution in 50 cm$^3$ of dichloromethane, 230 mg (48%) of the methyl ester of (3aRS,4SR,9SR,9aRS)-4,9-ethano-2-(2-methoxyphenyl)acetyl-9-phenyl-7-vinyl-2,3,3a,4,9,9a-hexahydro-1H-benzo[f]isoindole-3a-carboxylic acid are obtained, after purification by flash chromatography on silica gel (230–400 mesh), elution being carried out with a mixture of dichloromethane and methanol (98/2 by volume), in the form of a white powder, the characteristics of which are as follows: melting point=45–50° C., mass spectrum (D.C.I.: NH$_3$) M/Z=507 (MH$^+$).

From 0.32 g (0.63 mmol) of the methyl ester of (3aRS,4SR,9SR,9aRS)-4,9-ethano-2-(2-methoxyphenyl)acetyl-9-phenyl-7-vinyl-2,3,3a,4,9,9a-hexahydro-1H-benzo[f]isoindole-3a-carboxylic acid and 0.65 cm$^3$ of 1N sodium hydroxide in 40 cm$^3$ of ethanol, 138 mg (46%) of (3aRS,4SR,9SR,9aRS)-4,9-ethano-2-(2-methoxyphenyl)acetyl-9-phenyl-7-vinyl-2,3,3a,4,9,9a-hexahydro-1H-benzo[f]isoindole-3a-carboxylic acid are obtained, after purifying by high performance liquid chromatography on "Hyperprep" C$_{18}$-grafted silica gel, elution being carried out with an acetonitrile/water (50/50 by volume) mixture containing 0.05% of trifluoroacetic acid, in the form of a white powder, the characteristics of which are as follows: melting point=220° C., $^1$H N.M.R. spectrum (400 MHz, d6-(CD$_3$)$_2$SO, at a temperature of 383° K., δ in ppm): 1.40, 1.68, 1.95 and 2.10 (4 mts, each 1H, CH$_2$CH$_2$), from 3.30 to 3.65 (mt, 5H, CH$_2$ at 1, NCOCH$_2$, 1H of the CH$_2$ at 3 and H at 9a), 3.48 (mt, 1H, H at 4), 3.72 (broad s, 3H, OCH$_3$), 4.18 (d, J=12.5 Hz, 1H, the other H of the CH$_2$ at 3), 5.08 (broad d, J=11 Hz, 1H, H in the cis position of the =CH$_2$), 5.42 (broad d, J=17 Hz, 1H, H in the trans position of the =CH$_2$), 6.47 (d, J=1 Hz, 1H, H at 8), 6.57 (dd, J=17 and 11 Hz, 1H, ArCH=), 6.90 (broad t, J=7.5 Hz, 1H, aromatic H para to the OCH$_3$), 6.96 (broad d, J=7.5 Hz, 1H, aromatic H ortho to the OCH$_3$), from 7.15 to 7.30 (mt, 4H, H at 5, H at 6 and aromatic H meta to the OCH$_3$), 7.42 (mt, 3H, aromatic H in the ortho and para positions for the phenyl at 9), 7.54 (broad t, J=8 Hz, 2H, aromatic H in the meta positions for the phenyl at 9).

EXAMPLE 74

From 0.93 g (2.8 mmol) of the methyl ester of (3aRS,4SR,9SR,9aRS)-4,9-ethano-9-phenyl-2,3,3a,4,9,9a-hexahydro-1H-benzo[f]isoindole-3a-carboxylic acid, 0.51 g (2.8 mmol) of 2-ethoxyphenylacetic acid, 0.64 g (3.3 mmol) of 1-ethyl-3-(3-dimethylamino-propyl)carbodiimide hydrochloride and 37 mg (0.27 mmol) of hydroxybenzotriazole in solution in 30 cm$^3$ of dichloromethane, after stirring for 18 hours at a temperature in the region of 20° C. and purifying the crude product obtained by flash chromatography on silica gel (230–400 mesh), elution being carried out with a cyclohexane/ethyl acetate (70/30 by volume) mixture, 1.18 g (86%) of the methyl ester of (3aRS,4SR,9SR,9aRS)-4,9-ethano-2-(2-ethoxyphenyl)acetyl-9-phenyl-2,3,3a,4,9,9a-hexahydro-1H-benzo[f]isoindole-3a-carboxylic acid are obtained in the form of a white powder, the characteristics of which are as follows: melting point=142–144° C., mass spectrum (D.C.I.: NH$_3$) M/Z=495 (MH$^+$).

From 1.17 g (2.4 mmol) of the methyl ester of (3aRS,4SR,9SR,9aRS)-4,9-ethano-2-(2-ethoxyphenyl)acetyl-9-phenyl-2,3,3a,4,9,9a-hexahydro-1H-benzo[f]isoindole-3a-carboxylic acid, heated at reflux for 4 hours in 30 cm$^3$ of 1N sodium hydroxide and 30 cm$^3$ of ethanol, 890 mg (86%) of (3aRS,4SR,9SR,9aRS)-4,9-ethano-2-(2-ethoxyphenyl)acetyl-9-phenyl-2,3,3a,4,9,9a-hexahydro-1H-benzo[f]isoindole-3a-carboxylic acid are obtained, after purification by recrystallization from 90% ethanol, in the form of a white powder, the characteristics of which are as follows: melting point=251–253° C., mass spectrum (D.C.I.: NH$_3$) M/Z=481 (MH$^+$).

EXAMPLE 75

460 mg (0.96 mmol) of (3aRS,4SR,9SR,9aRS)-4,9-ethano-2-(2-ethoxyphenyl)acetyl-9-phenyl-2,3,3a,4,9,9a-hexahydro-1H-benzo[f]isoindole-3a-carboxylic acid are resolved on a chiral silica column carrying (3,5-dinitrobenzoyl)phenylalanine grafts prepared as in Example 31, elution being carried out with a dichloromethane/isopropanol/n-heptane (75/20/2.5 by volume) mixture. On collecting the second fraction eluted (retention time=17.2 minutes), 210 mg of (3aS,4R,9R,9S)-4,9-ethano-2-(2-ethoxyphenyl)acetyl-9-phenyl-2,3,3a,4,9,9a-hexahydro-1H-benzo(f]isoindole-3a-carboxylic acid, the dextrorotatory enantiomer, are obtained in the form of white crystals, the characteristics of which are as follows: melting point=221–223° C., optical rotation [α]$_{365}^{20}$=+53.6±1 (c=0.5, dichloromethane), mass spectrum (D.C.I.: NH$_3$) M/Z=481 (MH$^+$).

EXAMPLE 76

From 1.04 g (3.12 mmol) of the methyl ester of (3aRS,4SR,9SR,9aRS)-4,9-ethano-9-phenyl-2,3,3a,4,9,9a- hexahydro-1H-benzo[f]isoindole-3a-carboxylic acid, 0.60 g (3.12 mmol) of 8-chromanylacetic acid, 0.72 g (3.75 mmol) of 1-ethyl-3-(3-dimethylaminopropyl)carbodiimide hydrochloride and 40 mg (0.38 mmol) of hydroxybenzotriazole in solution in 30 cm³ of dichloromethane, after stirring for 18 hours at a temperature in the region of 20° C. and purifying the crude product obtained by flash chromatography on silica gel (230–400 mesh), elution being carried out with a cyclohexane/ethyl acetate (80/20 by volume) mixture, 1.41 g (89%) of the methyl ester of (3aRS,4SR,9SR,9aRS)-2-(8-chromanyl)acetyl-4,9-ethano-9-phenyl-2,3,3a,4,9,9a-hexahydro-1H-benzo[f]isoindole-3a-carboxylic acid are obtained in the form of a white powder, the characteristics of which are as follows: melting point=176–178° C., mass spectrum (D.C.I.: NH₃) M/Z=507 (MH⁺).

8-Chromanylacetic acid can be prepared in three stages from chroman, with an overall yield of 60%, as illustrated by Synth. Comm., 12, 763–70 (1982). On treatment with n-butyllithium and then with dimethylformamide in tetrahydrofuran, chroman results in 8-chromanal, which is then treated with trimethylsilyl cyanide in the presence of zinc iodide in dichloromethane. The trimethylsilylated cyanohydrin thus obtained is treated with stannous chloride in a mixture of acetic acid and hydrochloric acid, to provide 8-chromanylacetic acid.

From 0.92 g (1.8 mmol) of the methyl ester of (3aRS, 4SR,9SR,9aRS)-2-(8-chromanyl)acetyl-4,9-ethano-9-phenyl-2,3,3a,4,9,9a-hexahydro-1H-benzo[f]isoindole-3a-carboxylic acid, heated at reflux for 4 hours in 2.3 cm³ of 1N sodium hydroxide and 30 cm³ of ethanol, 500 mg (56%) of (3aRS,4SR,9SR,9aRS)-2-(8-chromanyl)acetyl-4,9-ethano-9-phenyl-2,3,3a,4,9,9a-hexahydro-1H-benzo[f]isoindole-3a-carboxylic acid are obtained, after purification by recrystallization from 90% ethanol, in the form of a white powder, the characteristics of which are as follows: melting point= 265–266° C., mass spectrum (D.C.I.: NH₃) M/Z=493 (MH⁺).

EXAMPLE 77

2.6 cm³ (5.2 mmol) of a 2M lithium diisopropylamide solution and 1.04 g (5 mmol) of the ethyl ester of (2-methoxyphenyl)oxoacetic acid in 10 cm³ of diethyl ether are successively added to a solution, cooled to approximately 0C, of 1.86 g (5 mmol) of triphenylphosphonioethyl bromide in 25 cm³ of diethyl ether. After stirring for 20 hours at a temperature in the region of 20° C., 30 cm³ of water are added. After separating by settling, the organic phase is washed with a 10% sodium dithionite solution, dried over magnesium sulphate and concentrated under reduced pressure. After purifying by flash chromatography on silica gel (230–400 mesh), elution being carried out with a mixture of cyclohexane and ethyl acetate (90/10 by volume), 0.5 g (46%) of the ethyl ester of 2-(2-methoxyphenyl)-2-butenoic acid is obtained in the form of a colourless oil containing an 80/20 mixture of the E and Z isomers, the characteristics of which are as follows: ¹H N.M.R. spectrum (300 MHz, CDCl₃, δ in ppm) (mixture of E and Z isomers in the proportions 80/20): 1.23 and 1.25 (2 t, J=7 Hz, 3H in total, CH₃ of the ethyl of the two isomers), 1.70 and 2.10 (2 d, J=6.5 Hz, 3H in total, respectively CH₃ of the major isomer and CH₃ of the minor isomer), 3.78 (s, 3H, COOCH₃ of the two isomers), 4.20 and 4.22 (2 q, J=7 Hz, 2H in total, respectively CH₂ of the major isomer and CH₂ of the minor isomer), 6.12 and 7.10 (2 q, J=6.5 Hz, 1 H in total, respectively =CH of the minor isomer and =CH of the major isomer), from 6.80 to 7.35 (mt, 4H, aromatic H).

The ethyl ester of (2-methoxyphenyl)oxoacetic acid can be obtained according to Synth. Comm., 20, 1781–91 (1990).

From 0.3 g (1.3 mmol) of the ethyl ester of 2-(2-methoxyphenyl)-2-butenoic acid in 13 cm³ of 1N sodium hydroxide and 13 cm³ of ethanol, 0.24 g (96%) of 2-(2-methoxyphenyl)-2-butenoic acid is obtained in the form of a white powder, the characteristics of which are as follows: melting point=205–206° C., mass spectrum (D.C.I. : NH₃) M/Z=192 (MH⁺).

From 0.42 g (1.26 mmol) of the methyl ester of (3aRS, 4SR,9SR,9aRS)-4,9-ethano-9-phenyl-2,3,3a,4,9,9a-hexahydro-1H-benzo[f]isoindole-3a-carboxylic acid, 0.25 g (1.26 mmol) of 2-(2-methoxyphenyl)-2-butenoic acid, 0.25 g (1.26 mmol) of 1-ethyl-3-(3-dimethylaminopropyl) carbodiimide hydrochloride and 17 mg (0.126 mmol) of hydroxybenzotriazole in solution in 20 cm³ of dichloromethane, after stirring for 18 hours at a temperature in the region of 20° C. and purifying the crude product obtained by flash chromatography on silica gel (230–400 mesh), elution being carried out with a cyclohexane/ethyl acetate (40/60 by volume) mixture, 0.39 g (61%) of the methyl ester of (3aRS,4SR,9SR,9aRS)-4,9-ethano-2-[2(E)-(2-methoxyphenyl)-2-butenoyl]-9-phenyl-2,3,3a,4,9,9a-hexahydro-1H-benzo[f]isoindole-3a-carboxylic acid is obtained in the form of a white powder, the characteristics of which are as follows: melting point=177–178° C., ¹H N.M.R. spectrum (400 MHz, d6-(CD₃)₂SO, at a temperature of 393° K., δ in ppm): 1.37, 1.60, 1.88 and 2.02 (4 mts, each 1H, CH₂CH₂), 1.58 (d, J=6.5 Hz, 3H, CH₃), 3.28 and 3.36 (respectively dd and broad d, J=11 and 8 Hz and J=11 Hz, each 1H, CH₂ at 1), 3.42 (mt, 2H, H at 9a and H at 4), 3.55 and 4.15 (2 d, J=12.5 Hz, each 1H, CH₂ at 3), 3.55 (s, 3H, COOCH₃), 3.63 (s, 3H, OCH₃), 6.19 (q, J=6.5 Hz, 1H, =CH), 6.41 (d, J=7.5 Hz, 1H, H at 8), 6.95 (broad t, J=7.5 Hz, 1H, aromatic H para to the OCH₃), 7.00 (broad d, J=7.5 Hz, 1H, aromatic H ortho to the OCH₃), from 7.00 to 7.45 (mt, 5H, H at 5, H at 6, H at 7 and aromatic H meta to the OCH₃), from 7.30 to 7.45 (mt, 3H, aromatic H in the ortho and para positions for the phenyl at 9), 7.53 (broad t, J=8 Hz, 2H, aromatic H in the meta positions for the phenyl at 9).

EXAMPLE 78

From 0.35 g (0.69 mmol) of the methyl ester of (3aRS, 4SR,9SR,9aRS)-4,9-ethano-2-[2(E)-(2-methoxyphenyl)-2-butenoyl]-9-phenyl-2,3,3a,4,9,9a-hexahydro-1H-benzo[f] isoindole-3a-carboxylic acid in 7 cm³ of 1N sodium hydroxide and 7 cm³ of ethanol, 0.18 g (52%) of (3aRS, 4SR,9SR,9aRS)-4,9-ethano-2-[2(E)-(2-methoxyphenyl)-2-butenoyl]-9-phenyl-2,3,3a,4,9,9a-hexahydro-1H-benzo[f] isoindole-3a-carboxylic acid is obtained, after recrystallization from a mixture of dichloromethane and pentane, in the form of a white powder, the characteristics of which are as follows: melting point=190–193° C., ¹H N.M.R. spectrum (400 MHz, d6-(CD₃)₂SO, at a temperature of 403° K., δ in ppm): 1.37, 1.60, 1.88 and 2.05 (4 mts, each 1H, CH₂CH₂), 1.60 (d, J=6.5 Hz, 3H, CH₃), 3.25 and 3.35 (respectively dd and broad d, J=12 and 8 Hz and J=12 Hz, each 1H, CH₂ at 1), 3.44 (mt, 2H, H at 9a and H at 4), 3.55 and 4.15 (2 d, J=12.5 Hz, each 1H, CH₂ at 3), 3.65 (s, 3H, OCH₃), 6.19 (q, J=6.5 Hz, 1H, =CH), 6.39 (d, J=7.5 Hz, 1H, H at 8), 6.95 (broad t, J=7.5 Hz, 1H, aromatic H para to the OCH₃), 7.00 (broad d, J=7.5 Hz, 1H, aromatic H ortho to the OCH₃), from 6.95 to 7.45 (mt, 5H, H at 5, H at 6, H at 7 and aromatic H meta to the OCH₃), from 7.30 to 7.45 (mt, 3H, aromatic H in the ortho and para positions of the phenyl at 9), 7.52 (broad t, J=8 Hz, 2H, aromatic H in the meta positions for the phenyl at 9).

EXAMPLE 79

From a solution of 2.16 g (5 mmol) of triphenylphosphonio(i-propyl) iodide in 25 cm³ of diethyl ether, 2.6 cm³ (5.2 mmol) of a 2M lithium diisopropylamide solution and 1.04 g (5 mmol) of the ethyl ester of (2-methoxyphenyl)oxoacetic acid in 10 cm³ of diethyl ether, 0.31 g (25%) of the ethyl ester of 2-(2-methoxyphenyl)-3-methyl-2-butenoic acid is obtained, after purification by flash chromatography on silica gel (230–400 mesh), elution being carried out with a cyclohexane/ethyl acetate (90/10 by volume) mixture, is obtained in the form of a colourless oil, the characteristics of which are as follows: mass spectrum (D.C.I.: NH₃) M/Z=234 (MH⁺).

From 0.3 g (1.28 mmol) of the ethyl ester of 2-(2-methoxyphenyl)-3-methyl-2-butenoic acid in 13 cm³ of 1N sodium hydroxide and 13 cm³ of ethanol, 0.21 g (80%) of 2-(2-methoxyphenyl)-3-methyl-2-butenoic acid is obtained in the form of a white powder, the characteristics of which are as follows: melting point=142–144° C., mass spectrum (D.C.I.: NH₃) M/Z=206 (MH⁺).

From 0.32 g (0.9 mmol) of the methyl ester of (3aRS,4SR,9SR,9aRS)-4,9-ethano-9-phenyl-2,3,3a,4,9,9a-hexahydro-1H-benzo[f]isoindole-3a-carboxylic acid, 0.21 g (0.9 mmol) of 2-(2-methoxyphenyl)-3-methyl-2-butenoic acid, 0.19 g (0.9 mmol) of 1-ethyl-3-(3-dimethylaminopropyl)-carbodiimide hydrochloride and 13.5 mg (0.1 mmol) of hydroxybenzotriazole in solution in 20 cm³ of dichloromethane, after stirring for 18 hours at a temperature in the region of 20° C. and purifying the crude product obtained by flash chromatography on silica gel (230–400 mesh), elution being carried out with a cyclohexane/ethyl acetate (10/90 by volume) mixture, and then recrystallization from pentane, 0.29 g (62%) of the methyl ester of (3aRS,4SR,9SR,9aRS)-4,9-ethano-2-[2-(2-methoxyphenyl)-3-methyl-2-butenoyl]-9-phenyl-2,3,3a,4,9,9a-hexahydro-1H-benzo[f]isoindole-3a-carboxylic acid is obtained in the form of a white powder, the characteristics of which are as follows: melting point=132–134° C., mass spectrum (D.C.I.: NH₃) M/Z=521 (MH⁺).

From 0.20 g (0.38 mmol) of the methyl ester of (3aRS,4SR,9SR,9aRS)-4,9-ethano-2-[2-(2-methoxyphenyl)-3-methyl-2-butenoyl]-9-phenyl-2,3,3a,4,9,9a-hexahydro-1H-benzo[f]isoindole-3a-carboxylic acid in 4 cm³ of 1N sodium hydroxide and 8 cm³ of ethanol, 0.16 g (83%) of (3aRS,4SR,9SR,9aRS)-4,9-ethano-2-[2-(2-methoxyphenyl)-3-methyl-2-butenoyl]-9-phenyl-2,3,3a,4,9,9a-hexahydro-1H-benzo[f]isoindole-3a-carboxylic acid is obtained, after recrystallization from a mixture of dichloromethane and pentane, in the form of a white powder, the characteristics of which are as follows: melting point=170–172° C., mass spectrum (D.C.I.: NH₃) M/Z=507 (MH⁺).

EXAMPLE 80

From 0.69 g (2.1 mmol) of the methyl ester of (3aRS,4SR,9SR,9aRS)-4,9-ethano-9-phenyl-2,3,3a,4,9,9a-hexahydro-1H-benzo[f]isoindole-3a-carboxylic acid, 0.40 g (2.1 mmol) of 2-n-propoxy-phenylacetic acid, 0.47 g (2.47 mmol) of 1-ethyl-3-(3-dimethylamino-propyl)carbodiimide hydrochloride and 30 mg (0.29 mmol) of hydroxybenzotriazole in solution in 20 cm³ of dichloromethane, after stirring for 18 hours at a temperature in the region of 20° C. and purifying the crude product obtained by flash chromatography on silica gel (230–400 mesh), elution being carried out with a cyclohexane/ethyl acetate (80/20 by volume) mixture, 0.95 g (91%) of the methyl ester of (3aRS,4SR,9SR,9aRS)-4,9-ethano-9-phenyl-2-(2-n-propoxyphenyl)acetyl-2,3,3a,4,9,9a-hexahydro-1H-benzo[f]isoindole-3a-carboxylic acid is obtained in the form of a white powder, the characteristics of which are as follows: melting point=140–145° C., mass spectrum (D.C.I.: NH₃) M/Z=495 (MH⁺).

2-n-Propoxyphenylacetic acid can be prepared in two stages from the methyl ester of 2-hydroxyphenylacetic acid, with an overall yield of 86%, by treatment with n-propyl iodide in the presence of potassium carbonate in dimethylformamide, followed by saponification of the ester obtained with 1N sodium hydroxide in ethanol.

From 0.95 g (1.8 mmol) of the methyl ester of (3aRS,4SR,9SR,9aRS)-4,9-ethano-9-phenyl-2-(2-n-propoxyphenyl)acetyl-2,3,3a,4,9,9a-hexahydro-1H-benzo[f]isoindole-3a-carboxylic acid, heated at reflux for 4 hours in 2.3 cm³ of 1N sodium hydroxide and 30 cm³ of ethanol, 260 mg (36%) of (3aRS,4SR,9SR,9aRS)-4,9-ethano-9-phenyl-2-(2-n-propoxyphenyl)acetyl-2,3,3a,4,9,9a-hexahydro-1H-benzo[f]isoindole-3a-carboxylic acid are obtained, after purification by recrystallization from 90% ethanol, in the form of a white powder, the characteristics of which are as follows: melting point=243–246° C., mass spectrum (D.C.I.: NH₃) M/Z=509 (MH⁺).

EXAMPLE 81

From 350 mg (0.73 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 214 mg (0.87 mmol) of the hydrochloride of t-butyl (S)-phenylglycinate, 168 mg (0.87 mmol) of 1-ethyl-3-(3-dimethylamino-propyl)carbodiimide hydrochloride and 10 mg (0.07 mmol) of hydroxybenzotriazole in solution in 10 cm³ of dichloromethane, after stirring for 18 hours at a temperature in the region of 20° C. and purifying by flash chromatography on silica gel (230–400 mesh), elution being carried out with a cyclohexane/ethyl acetate (80/20 by volume) mixture, 470 mg (94%) of N-[(S)-t-butyl-phenylglycinoyl)]-(3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxamide are obtained in the form of a white foam, the characteristics of which are as follows: melting point=170–175° C., mass spectrum (E.I.) M/Z=668 (M⁺).

460 mg (0.687 mmol) of N-[(S)-t-butyl-phenylglycinoyl)]-[(3aS,4R,9R,9aS)-4,9-ethano-2-(2-methoxy-phenylprop-2-en-1-oyl]-9-phenyl-2,3,3a,4,9,9a-hexahydro-1H-benzo[f]isoindole-3a-carboxamide and 1.6 cm³ (2.06 mmol) of trifluoroacetic acid in solution in 10 cm³ [lacuna] are stirred for 48 hours at a temperature in the region of 20° C. After concentrating under reduced pressure, the residue is taken up in 10 cm³ of petroleum ether. The precipitate formed is filtered off and then recrystallized from 90% ethanol. 330 mg (79%) of N-[(3aS,4R,9R,9aS)-4,9-ethano-2-[(2-methoxy-phenyl)prop-2-en-1-oyl]-9-phenyl-2,3,3a,4,9,9a-hexahydro-1H-benzo[f]isoindol-3a-ylcarboxamide]-(S)-phenylglycine are thus obtained in the form of a white powder, the characteristics of which are as follows: melting point=205–210° C., mass spectrum (E.I.) M/Z=612 (M⁺).

EXAMPLE 82

From 200 mg (0.417 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 69 mg (0.5 mmol) of 2-methoxybenzylamine, 96 mg (0.5 mmol) of 1-ethyl-3-(3- dimethylaminopropyl)carbodiimide hydrochloride and 6 mg (0.045 mmol) of hydroxybenzotriazole in solution in 10 cm$^3$ of dichloromethane, after stirring for 18 hours at a temperature in the region of 20° C. and purifying by flash chromatography on silica gel (230–400 mesh), elution being carried out with a cyclohexane/ethyl acetate (50/50 by volume) mixture, 210 mg (84%) of (3aS,4R,9R,9aS)-N-[2-methoxybenzyl)]- 4,9-ethano-2-[(2-methoxyphenyl)prop-2-en-1-oyl]-9-phenyl-2,3,3a,4,9,9a-hexahydro-1H-benzo[f]isoindole-3a-carboxamide are obtained in the form of a white powder, the characteristics of which are as follows: melting point=114–116° C., mass spectrum (E.I.) M/Z=598 (M$^+$).

EXAMPLE 83

From 200 mg (0.417 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 89 mg (0.5 mmol) of (R)-1-(1-naphthyl)ethylamine, 96 mg (0.5 mmol) of 1-ethyl-3-(3-dimethylaminopropyl)carbodiimide hydrochloride and 6 mg (0.045 mmol) of hydroxybenzotriazole in solution in 10 cm$^3$ of dichloromethane, after stirring for 18 hours at a temperature in the region of 20° C. and purifying by flash chromatography on silica gel (230–400 mesh), elution being carried out with a cyclohexane/ethyl acetate (50/50 by volume) mixture, 200 mg (77%) of (3aS,4R,9R,9aS)-N-[(R)-1-(1-naphthyl)ethyl]-4,9-ethano-2-[(2-methoxyphenyl)prop-2-en-1-oyl]-9-phenyl-2,3,3a,4,9,9a-hexahydro-1H-benzo[f]isoindole-3a-carboxamide are obtained in the form of a white powder, the characteristics of which are as follows: melting point=139–143° C., mass spectrum (E.I.) M/Z=632 (M$^+$).

EXAMPLE 84

From 250 mg (0.52 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 83 mg (0.625 mmol) of (R,S)-1-aminoindane, 120 mg (0.625 mmol) of 1-ethyl-3-(3-dimethylaminopropyl)carbodiimide hydrochloride and 7 mg (0.052 mmol) of hydroxybenzotriazole in solution in 10 cm$^3$ of dichloromethane, after stirring for 18 hours at a temperature in the region of 20° C. and purifying by flash chromatography on silica gel (230–400 mesh), elution being carried out with dichloromethane containing 0.25% of methanol, 270 mg (90%) of (3aS,4R,9R,9aS)-N-[(R,S)-1-indanyl]-4,9-ethano-2-[(2-methoxyphenyl)prop-2-en-1-oyl]-9-phenyl-2,3,3a,4,9,9a-hexahydro-1H-benzo[f]isoindole-3a-carboxamide are obtained in the form of a white powder, the characteristics of which are as follows: melting point= 174–175° C., mass spectrum (E.I.) M/Z=594 (M$^+$).

EXAMPLE 85

From 250 mg (0.52 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-)carboxylic acid (Example 39), 70 mg (0.52 mmol) of (S)-2-phenylglycinol, 120 mg (0.625 mmol) of 1-ethyl-3-(3-dimethylaminopropyl)carbodiimide hydrochloride and 7 mg (0.052 mmol) of hydroxybenzotriazole in solution in 10 cm$^3$ of dichloromethane, after stirring for 18 hours at a temperature in the region of 20° C. and purifying by flash chromatography on silica gel (230–400 mesh), elution being carried out with a cyclohexane/ethyl acetate (80/20 by volume) mixture, 170 mg (55%) of (3aS,4R,9R,9aS)-N-[1-(S)-1-phenyl-2-hydroxyethyl]-4,9-ethano-2[-(2-methoxyphenyl)prop-2-en-1-oyl]-9-phenyl-2,3,3a,4,9,9a-hexahydro-1H-benzo[f]isoindole-3a-carboxamide are obtained in the form of a white powder, the characteristics of which are as follows: melting point=230–231° C., mass spectrum (E.I.) M/Z=598 (M$^+$).

EXAMPLE 86

From 240 mg (0.5 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 81 mg (0.6 mmol) of cumylamine, 115 mg (0.6 mmol) of 1-ethyl-3-(3-dimethylaminopropyl)carbodiimide hydrochloride and 13 mg (0.1 mmol) of hydroxybenzotriazole in solution in 10 cm$^3$ of dichloromethane, after stirring for 18 hours at a temperature in the region of 20° C. and purifying by flash chromatography on silica gel (230–400 mesh), elution being carried out with mixtures of cyclohexane and ethyl acetate (95/5 then 80/20 by volume), 69 mg (23%) of (3aS,4R,9R,9aS)-N-(2,2-dimethylbenzyl)-4,9-ethano-2[-(2-methoxyphenyl)prop-2-en-1-oyl]-9-phenyl-2,3,3a,4,9,9a-hexahydro-1H-benzo[f]isoindole-3a-carboxamide are obtained in the form of a white powder, the characteristics of which are as follows: melting point=142–143° C., mass spectrum (E.I.) M/Z=596 (M$^+$).

EXAMPLE 87

From 250 mg (0.52 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 84 mg (0.52 mmol) of (R,S)-2-phenylglycinonitrile, 115 mg (0.6 mmol) of 1-ethyl-3-(3-dimethylaminopropyl)carbodiimide hydrochloride and 10 mg (0.075 mmol) of hydroxybenzotriazole in solution in 10 cm$^3$ of dichloromethane, after stirring for 18 hours at a temperature in the region of 20° C. and purifying by flash chromatography on silica gel (230–400 mesh), elution being carried out with cyclohexane/ethyl acetate (80/20 then 50/50 by volume) mixtures, 70 mg (23%) of (3aS,4R,9R,9aS)-N-[1-(R,S)-1-cyano-1-phenylmethyl]-4,9-ethano-2-[(2-methoxyphenyl)prop-2-en-1-oyl]-9-phenyl-2,3,3a,4,9,9a-hexahydro-1H-benzo[f]isoindole-3a-carboxamide are obtained in the form of a white powder, the characteristics of which are as follows: melting point=98–100° C., mass spectrum (E.I.) M/Z=593 (M$^+$).

EXAMPLE 88

From 200 mg (0.42 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 100 mg (0.5 mmol) of (R,S)-4-aminobenzo[b]thiopyran hydrochloride, 96 mg (0.5 mmol) of 1-ethyl-3-(3-dimethylaminopropyl)-carbodiimide hydrochloride and 6 mg (0.042 mmol) of hydroxybenzotriazole in solution in 10 cm$^3$ of dichloromethane, after stirring for 18 hours at a temperature in the region of 20° C. and purifying by flash chromatography on silica gel (230–400 mesh), elution being carried out with a cyclohexane/ethyl acetate (60/40 by volume) mixture, 170 mg (65%) of (3aS,4R,9R,9aS)-N-[(R,S)-4-benzo[b]thiopyranyl]-4,9-ethano-2-[(2-methoxyphenyl)prop-2-en-1-oyl]-9-phenyl-2,3,3a,4,9,9a-hexahydro-1H-benzo[f]isoindole-3a-carboxamide are obtained in the form of a white powder, the characteristics of which are as follows: melting point=143–146° C., mass spectrum (E.I.) M/Z=626 (M$^+$).

EXAMPLE 89

From 200 mg (0.42 mmol) of (3aS,4R,9R,9aS)-4,9-ethano-2-[(2-methoxyphenyl)prop-2-en-1-oyl]- 9-phenyl-2,3,3a,4,9,9a-hexahydro-1H-benzo[f]isoindole-3a-carboxylic acid (Example 39), 88 mg (0.5 mmol) of 3-trifluorobenzylamine, 96 mg (0.5 mmol) of 1-ethyl-3-(3-dimethylaminopropyl)carbodiimide hydrochloride and 6 mg (0.042 mmol) of hydroxybenzotriazole in solution in 15 cm³ of dichloromethane, after stirring for 18 hours at a temperature in the region of 20° C. and purifying by flash chromatography on silica gel (230–400 mesh), elution being carried out with a cyclohexane/ethyl acetate (50/50 by volume) mixture, 217 mg (81%) of (3aS,4R,9R,9aS)-N-[3-trifluorobenzyl]-4,9-ethano-2-[(2-methoxyphenyl)prop-2-en-1-oyl]-9-phenyl-2,3,3a,4,9,9a-hexahydro-1H-benzo[f] isoindole-3a-carboxamide are obtained in the form of a pale-yellow powder, the characteristics of which are as follows: melting point=118–120° C., mass spectrum (E.I.) M/Z=636 (M⁺).

EXAMPLE 90

From 200 mg (0.42 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 84 mg (0.5 mmol) of veratrylamine, 96 mg (0.5 mmol) of 1-ethyl-3-(3-dimethylaminopropyl) carbodiimide hydrochloride and 6 mg (0.042 mmol) of hydroxybenzotriazole in solution in 15 cm³ of dichloromethane, after stirring for 18 hours at a temperature in the region of 20° C. and purifying by flash chromatography on silica gel (230–400 mesh), elution being carried out with a cyclohexane/ethyl acetate (80/20 by volume) mixture, 190 mg (73%) of (3aS,4R,9R,9aS)-N-(3,4-dimethoxybenzyl)-4,9-ethano-2-[(2-methoxyphenyl)prop-2-en-1-oyl]-9-phenyl-2,3,3a,4,9,9a-hexahydro-1H-benzo[f] isoindole-3a-carboxamide are obtained in the form of a white powder, the characteristics of which are as follows: melting point=102–105° C., mass spectrum (E.I.) M/Z=628 (M⁺).

EXAMPLE 91

From 200 mg (0.42 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 54 mg (0.5 mmol) of 3-picolylamine, 96 mg (0.5 mmol) of 1-ethyl-3-(3-dimethylaminopropyl) carbodiimide hydrochloride and 6 mg (0.042 mmol) of hydroxybenzotriazole in solution in 15 cm³ of dichloromethane, after stirring for 18 hours at a temperature in the region of 20° C. and purifying by flash chromatography on silica gel (230–400 mesh), elution being carried out with an ethyl acetate/methanol (90/10 by volume) mixture, 176 mg (74%) of (3aS,4R,9R,9aS)-N-[(3-pyridyl)methyl]-4,9-ethano-2-[(2-methoxyphenyl)prop-2-en-1-oyl]-9-phenyl-2,3,3a,4,9,9a-hexahydro-1H-benzo[f]isoindole-3a-carboxamide are obtained in the form of a white powder, the characteristics of which are as follows: melting point=150–154° C., mass spectrum (E.I.) M/Z=569 (M⁺).

EXAMPLE 92

From 200 mg (0.42 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 88 mg (0.5 mmol) of 4-trifluorobenzylamine, 96 mg (0.5 mmol) of 1-ethyl-3-(3-dimethylaminopropyl)carbodiimide hydrochloride and 6 mg (0.042 mmol) of hydroxybenzotriazole in solution in 15 cm³ of dichloromethane, after stirring for 18 hours at a temperature in the region of 20° C. and purifying by flash chromatography on silica gel (230–400 mesh), elution being carried out with a cyclohexane/ethyl acetate (60/40 by volume) mixture, 200 mg (77%) of (3aS,4R,9R,9aS)-N-[4-trifluorobenzyl]-[4,9-ethano-2-(2-methoxyphenyl)prop-2-en-1-oyl]-9-phenyl-2,3,3a,4,9,9a-hexahydro-1H-benzo[f] isoindole-3a-carboxamide are obtained in the form of a pale-yellow powder, the characteristics of which are as follows: melting point=149–151° C., mass spectrum (E.I.) M/Z=636 (M⁺).

EXAMPLE 93

From 200 mg (0.42 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 54 mg (0.5 mmol) of 2-picolylamine, 96 mg (0.5 mmol) of 1-ethyl-3-(3-dimethylaminopropyl) carbodiimide hydrochloride and 6 mg (0.042 mmol) of hydroxybenzotriazole in solution in 15 cm³ of dichloromethane, after stirring for 18 hours at a temperature in the region of 20° C. and purifying by flash chromatography on silica gel (230–400 mesh), elution being carried out with ethyl acetate/methanol (95/5 then 90/10 by volume) mixtures, 210 mg (91%) of (3aS,4R,9R,9aS)-N-[(2-pyridyl)-methyl]-4,9-ethano-2-[(2-methoxyphenyl)prop-2-en-1-oyl]-9-phenyl-2,3,3a,4,9,9a-hexahydro-1H-benzo[f] isoindole-3a-carboxamide are obtained in the form of a white powder, the characteristics of which are as follows: melting point=137–139° C., mass spectrum (E.I.) M/Z=569 (M⁺).

EXAMPLE 94

From 200 mg (0.42 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 49 mg (0.5 mmol) of furfurylamine, 96 mg (0.5 mmol) of 1-ethyl- 3-(3-dimethylaminopropyl) carbodiimide hydrochloride and 6 mg (0.042 mmol) of hydroxybenzotriazole in solution in 15 cm³ of dichloromethane, after stirring for 18 hours at a temperature in the region of 20° C. and purifying by flash chromatography on silica gel (230–400 mesh), elution being carried out with a cyclohexane/ethyl acetate (50/50 by volume) mixture, 200 mg (87%) of (3aS,4R,9R,9aS)-N-[(2-furyl)-methyl]-4,9-ethano-2-[(2-methoxyphenyl)prop-2-en-1-oyl]-9-phenyl-2,3,3a,4,9,9a-hexahydro-1H-benzo[f]isoindole-3a-carboxamide are obtained in the form of an orangey-yellow powder, the characteristics of which are as follows: melting point=170–171° C., mass spectrum (E.I.) M/Z=558 (M⁺).

EXAMPLE 95

From 200 mg (0.42 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 56 mg (0.5 mmol) of 2-(aminomethyl) thiophene, 96 mg (0.5 mmol) of 1-ethyl-3-(3-dimethylaminopropyl)carbodiimide hydrochloride and 6 mg (0.042 mmol) of hydroxybenzotriazole in solution in 15 cm³ of dichloromethane, after stirring for 18 hours at a temperature in the region of 20° C. and purifying by flash chromatography on silica gel (230–400 mesh), elution being carried out with a cyclohexane/ethyl acetate (50/50 by volume) mixture, 180 mg (75%) of (3aS,4R,9R,9aS)-N-[(2-thienyl)- methyl]-4,9-ethano-2-[(2-methoxyphenyl)prop-2-en-1-oyl]-9-phenyl-2,3,3a,4,9,9a-hexahydro-1H-benzo[f]isoindole-3a-carboxamide are obtained in the form of a beige powder, the characteristics of which are as follows: melting point= 133–135° C., mass spectrum (E.I.) M/Z=574 (M+).

EXAMPLE 96

From 200 mg (0.42 mmol) of (3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxylic acid (Example 39), 56 mg (0.5 mmol) of 4-(aminomethyl)thiazole, 96 mg (0.5 mmol) of 1-ethyl-3-(3-dimethylaminopropyl)carbodiimide hydrochloride and 6 mg (0.042 mmol) of hydroxybenzotriazole in solution in 15 cm³ of dichloromethane, after stirring for 18 hours at a temperature in the region of 20° C. and purifying by flash chromatography on silica gel (230–400 mesh), elution being carried out with a cyclohexane/ethyl acetate (60/40 by volume) mixture, 115 mg (48%) of (3aS,4R,9R,9aS)-N-[(4-thiazolyl)-methyl]-4,9-ethano-2-[(2-methoxyphenyl)prop-2-en-1-oyl]-9-phenyl-2,3,3a,4,9,9a-hexahydro-1H-benzo[f]isoindole-3a-carboxamide are obtained in the form of a beige powder, the characteristics of which are as follows: melting point=136–138° C., mass spectrum (E.I.) M/Z=573 (M+).

4-(Aminomethyl)thiazole can be prepared according to Zhur. Obshchei. Khim., 31, 1356–1361 (1961).

EXAMPLE 97

From 2 g (3.6 mmol) of the methyl ester of (3aRS,4SR,9SR,9aRS)-4,9-ethano-6-iodo-9-phenyl-2-(t-butoxycarbonyl)-2,3,3a,4,9,9a-hexahydro-1H-benzo[f]isoindole-3a-carboxylic acid, obtained as in Example 43, 1.3 cm³ of tri(n-butyl)vinylstannane and 310 mg (0.27 mmol) of tetrakis(triphenylphosphine)-palladium in 65 cm³ of dimethylformamide, the preparation being carried out as in Example 73, 740 mg (45%) of the methyl ester of (3aRS,4SR,9SR,9aRS)-4,9-ethano-9-phenyl-2-(t-butoxycarbonyl)-6-vinyl-2,3,3a,4,9,9a-hexahydro-1H-benzo[f]isoindole-3a-carboxylic acid are obtained, after purification by flash chromatography on silica gel (230–400 mesh), elution being carried out with a cyclohexane/ethyl acetate (95/5 by volume) mixture, in the form of a pale-yellow foam, the characteristics of which are as follows: mass spectrum (E.I.) M/Z=459 (M+).

From 280 mg (0.62 mmol) of the methyl ester of (3aRS,4SR,9SR,9aRS)-4,9-ethano-9-phenyl-2-(t-butoxycarbonyl)-6-vinyl-2,3,3a,4,9,9a-hexahydro-1H-benzo[f]isoindole-3a-carboxylic acid in an excess of hydrochloric acid in methanol, 235 mg (98%) of the hydrochloride of the methyl ester of (3aRS,4SR,9SR,9aRS)-4,9-ethano-9-phenyl-6-vinyl-2,3,3a,4,9,9a-hexahydro-1H-benzo[f]isoindole-3a-carboxylic acid are obtained in the form of a white powder, the characteristics of which are as follows: mass spectrum (E.I.) M/Z=395 (M+).

From 230 mg (0.58 mmol) of the methyl ester of (3aRS,4SR,9SR,9aRS)-4,9-ethano-9-phenyl-6-vinyl-2,3,3a,4,9,9a-hexahydro-1H-benzo[f]isoindole-3a-carboxylic acid, 116 mg (0.7 mmol) of (2-methoxyphenyl)acetic acid, 137 mg (0.7 mmol) of 1-ethyl-3-(3-dimethylaminopropyl)carbodiimide hydrochloride and 8 mg (0.06 mmol) of hydroxybenzotriazole in solution in 350 cm³ of dichloromethane, after stirring for 18 hours at a temperature in the region of 20° C. and purifying the crude product obtained by flash chromatography on silica gel (230–400 mesh), elution being carried out with dichloromethane, 260 mg (88%) of the methyl ester of (3aRS,4SR,9SR,9aRS)-4,9-ethano-2-[(2-methoxyphenyl)-acetyl]-9-phenyl-6-vinyl-2,3,3a,4,9,9a-hexahydro-1H-benzo[f]isoindole-3a-carboxylic acid are obtained in the form of a white powder, the characteristics of which are as follows: melting point= 54–56° C., mass spectrum (D.C.I.: NH₃) m³/z=507 (MH+).

350 mg (0.69 mmol) of the methyl ester of (3aRS,4SR,9SR,9aRS)-4,9-ethano-2-[(2-methoxyphenyl)-acetyl]-9-phenyl-6-vinyl-2,3,3a,4,9,9a-hexahydro-1H-benzo[f]isoindole-3a-carboxylic acid are dissolved in 35 cm³ of dichloromethane in a 100 cm³ three-necked flask connected to an ozonizer, 0.35 cm³ of methanol is then added and the mixture is cooled to −70° C. Ozone is then sparged into the reaction mixture at −70° C. for approximately 1 hour 45 minutes, until a stable bluish colouring appears. After stirring for an additional 1 hour at this temperature, sparging is carried out with compressed air in order to drive off the excess ozone, 170 mg (2.8 mmol) of dimethyl sulphide are then added and the reaction mixture is allowed to return to room temperature. After concentrating under reduced pressure, the oily residue is taken up in ethyl acetate and washed with water to neutrality. After drying over magnesium sulphate and concentrating under reduced pressure, the yellow oil obtained is purified by flash chromatography on silica gel (230–400 mesh), elution being carried out with a cyclohexane/ethyl acetate (80/20 by volume) mixture. 68 mg (19%) of the methyl ester of (3aRS,4SR,9SR,9aRS)-4,9-ethano-6-formyl-2-[(2-methoxyphenyl)acetyl]-9-phenyl-2,3,3a,4,9,9a-hexahydro-1H-benzo[f]isoindole-3a-carboxylic acid are thus obtained in the form of a white powder, the characteristics of which are as follows: melting point=109–110° C., mass spectrum (D.C.I.: NH₃) M/Z=509 (MH+).

The inhibitory activity with respect to farnesyl transferase and to farnesylation of the Ras protein may be demonstrated in the following test:

Farnesyl transferase activity is determined by the amount of ($^3$H) farnesyl transferred from ($^3$H) farnesylpyrophosphate [($^3$H) FPP] to the p21 H-ras protein. The standard reaction mixture is composed, for a final volume of 60 ml, of 50 mM Tris-HCl, 5 mM MgCl₂, 5 mM dithiotreitol, 0.2% octyl b-D-glucopyranoside, 200 picomol p21 H-ras, 4.5 picomol ($^3$H) FPP (activity 61000 dpm/picomol).

Reaction is initiated by adding approximately 5 ng of human farnesyl transferase purified from THP1 cell cultures. After incubation for 20 minutes at 37° C. in a microtitration plate containing 96 1-cm³ wells per plate (Titer Plate®, Beckman), the reaction is stopped by adding 0.4 cm³ of 0.1% SDS in methanol at 0° C. The mixture is then treated with 0.4 cm³ of 30% trichloroacetic® acid (TCA) in methanol. The plates are left in ice for 1 hour. The precipitated contents are then retained on Filtermat®, Pharmacia), glass® fibre membranes with the filtration unit (Combi Cell Harvester®, Skatron), and rinsed with 6% trichloroacetic acid in distilled water. The membranes are dried in a microwave oven, then impregnated with scintillation medium by melting of Meltilex® (Pharmacia) under hot air, and lastly counted in cpm in a b-Plate counter® (LKB). Each test is repeated 3 times.

The unit of activity is defined as 1 picomole of ($^3$H) FPP transferred to p21 H-ras in 20 minutes.

The percentage inhibition values are obtained by comparison of the tests with and without inhibitor after deduction of blanks, the IC₅₀ values being measured on the basis of the inhibitions obtained with 9 different concentrations using Enzfitter® or Grafit® software.

The results obtained are collated in Table I.

TABLE I

| Product | vitro inhibitory activity IC$_{50}$ ($\mu$M) |
|---|---|
| Example 1 | 0.41 |
| Example 2 | 0.31 |
| Example 3 | 4.70 |
| Example 4 | 9.40 |
| Example 5 | 7.0 |
| Example 6 | 1.10 |
| Example 7 | 0.58 |
| Example 8 | 0.19 |
| Example 9 | 0.19 |
| Example 10 | 4.35 |
| Example 11 | 6.95 |
| Example 12 | 7.50 |
| Example 13 | 8.80 |
| Example 14 | 8.70 |
| Example 15 | 9.0 |
| Example 16 | 3.03 |
| Example 17 | 4.90 |
| Example 18 | 10.0 |
| Example 19 | 5.60 |
| Example 20 | 4.80 |
| Example 21 | 3.75 |
| Example 22 | 10.0 |
| Example 23 | 2.60 |
| Example 24 | 4.20 |
| Example 25 | 2.60 |
| Example 26 | 2.30 |
| Example 27 | 5.80 |
| Example 28 | 3.05 |
| Example 29 | 2.30 |
| Example 30 | 0.60 |
| Example 31 | 0.62 |
| Example 32 | 1.33 |
| Example 33 | 2.03 |
| Example 34 | 0.59 |
| Example 35 | 2.15 |
| Example 36 | 3.70 |
| Example 37 | 7.40 |
| Example 38 | 0.10 |
| Example 39 | 0.05 |
| Example 40 | 2.95 |
| Example 41 | 1.10 |
| Example 42 | 8.45 |
| Example 43 | 0.70 |
| Example 44 | 0.11 |
| Example 45 | 1.27 |
| Example 46 | 1.25 |
| Example 47 | 0.14 |
| Example 48 | 0.74 |
| Example 49 | 1.10 |
| Example 50 | 1.30 |
| Example 51 | 0.15 |
| Example 52 | 0.44 |
| Example 53 | 0.59 |
| Example 54 | 4.70 |
| Example 55 | 3.90 |
| Example 56 | 8.40 |
| Example 57 | 0.86 |
| Example 58 | 5.05 |
| Example 59 | 5.00 |
| Example 60 | 1.80 |
| Example 61 | 4.70 |
| Example 62 | 1.15 |
| Example 63 | 7.00 |
| Example 64 | 0.75 |
| Example 65 | 0.41 |
| Example 66 | 9.20 |
| Example 67 | 0.95 |
| Example 68 | 2.25 |
| Example 69 | 9.10 |
| Example 70 | 2.85 |
| Example 71 | 0.50 |
| Example 72 | 0.69 |
| Example 73 | 3.15 |
| Example 74 | 0.19 |
| Example 75 | 0.37 |
| Example 76 | 3.65 |
| Example 77 | 6.70 |
| Example 78 | 0.65 |
| Example 79 | 5.05 |
| Example 80 | 0.80 |
| Example 81 | 0.05 |
| Example 82 | 0.21 |
| Example 83 | 5.15 |
| Example 84 | 0.33 |
| Example 85 | 0.26 |
| Example 86 | 4.85 |
| Example 87 | 0.25 |
| Example 88 | 2.50 |
| Example 89 | 0.78 |
| Example 90 | 0.97 |
| Example 91 | 0.16 |
| Example 92 | 4.80 |
| Example 93 | 0.45 |
| Example 94 | 0.43 |
| Example 95 | 0.27 |
| Example 96 | 0.36 |
| Example 97 | 3.95 |

The activity against cells can be determined in the following way:

The cell line is the THAC line (CCL 39 cells transfected with activated Ha-Ras) according to K. Seuwen et al., EMBO J., 7(1) 161–168 (1988). The cells are cultured in Petri dishes with a diameter of 6 cm containing a DMEM medium, 5% foetal calf serum and 1% G418.

After culturing for 24 hours, the culture medium is changed (with or without the serum) and the product to be studied is added in solution in dimethylformamide (DMF), in the presence or in the absence of DTT (final concentrations of 0.5% in DMF and 0.1 mM in DTT). After culturing for 24 hours at 37° C., the cells are lysed in 1 cm$^3$ of lysis buffer (20 mM Tris, HCl, 1% Triton X114, 5 mM MgCl$_2$, 7 mM DTT, 150 mM NaCl, pH=7.4). The lysates are clarified by centrifuging at 4000 revolutions/minute for 10 minutes. Extraction with Triton X114 makes it possible to separate the farnesylated Ras protein from the non-farnesylated Ras protein (C. Bordier, J. Biol. Chem., 256 (4), 1604–1607 (1981)]. The farnesylated Ras protein, which is more hydrophobic, is found in the detergent phase whereas the non-farnesylated Ras protein is in the aqueous phase. The samples are denatured by heating at 95° C. in the denaturation buffer for electrophoresis and deposited on a 14% polyacrylamide gel. When the dye reaches the bottom of the gel, the proteins of the gel are transferred onto a PVDF membrane. The Ras protein is visualized by the Western blot technique: the membrane is incubated with an anti-Ras specific monoclonal antibody (pan-Ras Ab3, Oncogene Science) and then with protein A labelled with $^{125}$I. After autoradiography, the bands are identified, cut out and counted in a γ counter. The radioactivity of the bands corresponding to farnesylated Ras and to non-farnesylated Ras makes it possible to determine the percentage of inhibition of farnesylation of the Ras protein.

The products according to the invention inhibit farnesylation of the Ras protein by 50% at concentrations of between 100 nM and 100 $\mu$M.

The new products of general formula (I) can be in the form of non-toxic and pharmaceutically acceptable salts. These non-toxic salts comprise the salts with inorganic acids (hydrochloric, sulphuric, hydrobromic, phosphoric and nitric acids) or with organic acids (acetic, propionic, succinic, maleic, hydroxymaleic, benzoic, fumaric, methanesulphonic, trifluoroacetic or oxalic acid), or with inorganic bases (sodium hydroxide, potassium hydroxide, lithium hydroxide, calcium hydroxide) or organic bases (tertiary amines such as triethylamine, piperidine, benzylamine), depending on the nature of the amino acids which constitute the peptide of general formula (I).

The new products according to the invention, which inhibit farnesyl transferase and farnesylation of the Ras protein, are notable anticancer agents which act against both solid and non-solid tumours.

The products of general formula (I) in which one of the $R_1$ and $R_2$ symbols represents a hydrogen atom and the other represents an alkyloxy radical containing from 1 to 4 carbon atoms, $R_3$ represents a hydrogen atom, X represents a methylene radical, Y represents an oxygen atom and R represents a radical of general formula —$(CH_2)_m$—$X_1$—$(CH_2)_n$—Z, in which m is equal to 0 or 1, $X_1$ represents a bond and n is equal to 0 and Z represents a carboxyl radical or a —$COOR_4$ radical for which $R_4$ represents an alkyl radical containing 1 to 6 carbon atoms or a $CON(R_5)(R_6)$ radical in which $R_5$ and $R_6$ are defined as above, are very particularly advantageous.

Mention may even more particularly be made of (3aS,4R,9R,9aS)-4,9-ethano-2-[2-(2-methoxyphenyl)prop-2-en-1-oyl]-9-phenyl-1,2,3,3a,9,9a-hexahydro-1H-benzo[f]isoindole-3a-carboxylic acid, the dextrorotatory enantiomer, optionally in the form of an ester containing 1 to 3 carbon atoms, of the amide or of an N-substituted amide, and N-[(S)-t-butyl-phenylglycinoyl]-(3aS,4R,9R,9aS)-4,9-ethano-2-[(2-methoxy-phenyl)prop-2-en-1-oyl]-9-phenyl-2,3,3a,4,9,9a-hexahydro-1H-benzo[f]isoindole-3a-carboxamide.

The present invention also relates to pharmaceutical compositions which contain at least one product of general formula (I), in combination with one or a number of pharmaceutically acceptable diluents or adjuvants, which may be either inert or physiologically active.

These compositions may be administered orally, parenterally or rectally.

The compositions for oral administration comprise tablets, pills, powders or granules. In these compositions, the active product according to the invention is mixed with one or a number of inert diluents such as sucrose, lactose or starch. These compositions can comprise substances other than diluents, for example a lubricant such as magnesium stearate.

As liquid compositions for oral administration, solutions, suspensions, syrups, elixirs and pharmaceutically acceptable emulsions, containing inert diluents such as water or liquid paraffin, may be used. These compositions can also comprise substances other than diluents, for example wetting, sweetening or flavouring products.

The compositions according to the invention for parenteral administration can be suspensions, emulsions or aqueous or non-aqueous sterile solutions. As solvent or vehicle, propylene glycol, a polyethylene glycol, vegetable oils, especially olive oil, or injectable organic esters, for example ethyl oleate, may be employed. These compositions can also contain adjuvants, especially wetting, emulsifying and dispersing agents. The sterilization may be carried out in several ways, for example using a bacteriological filter, by incorporating sterilizing agents in the composition or by heating. They may also be prepared in the form of sterile solid compositions which can be dissolved at the time of use in sterile water or any other sterile injectable medium.

The compositions for rectal administration are suppositories which can contain, besides the active product, excipients such as cocoa butter.

The compositions according to the invention are particularly useful in human therapy in the treatment of cancers of various origins.

In human therapy, the doses depend on the effect sought, the period of treatment and factors specific to the subject to be treated.

Generally, in man, the doses are between 0.1 and 20 mg/kg per day via the intraperitoneal route.

We claim:

1. A compound of formula (I):

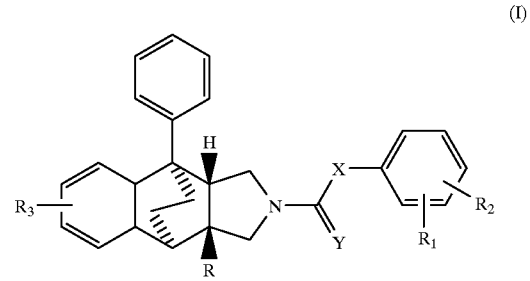

(I)

in which:

R represents:
a group of formula —$(CH_2)_m$—$X_1$—$(CH_2)_n$—Z in which
$X_1$ represents a single bond or an oxygen or sulphur atom,
m represents an integer equal to 0 or 1, and
n represents an integer equal to 0, 1 or 2;
wherein one or more methylene groups in said R group may be substituted by at least one carboxyl group, an alkoxycarbonyl group, a carbamoyl group, an alkylcarbamoyl group, a dialkylcarbamoyl group, an amino group, an alkylamino group, or a dialkylamino group, wherein each alkyl portion in the definition of R contains 1 to 4 carbon atoms; and Z represents
a carboxyl group, or
a $COOR_4$ group, in which $R_4$ represents a straight or branched alkyl group containing 1 to 3 carbon atoms, or
a $CON(R_5)(R_6)$ group, in which $R_5$ represents a hydrogen atom or a straight or branched alkyl group containing 1 to 6 carbon atoms, and $R_6$ represents a hydrogen atom, an indanyl or thiochromanyl group, or a straight or branched alkyl group containing 1 to 6 carbon atoms optionally substituted by one or more amino, alkylamino, dialkylamino, hydroxyl, alkyloxy, mercapto, alkylthio, aralkylthio, alkyloxycarbonyl, carboxyl, cyano, phenyl optionally substituted by one or more identical or different groups selected from halogen atoms and alkyl, alkyloxy, dialkylamino, cyano, and trifluoromethyl groups, or a 1- or 2-naphthyl, 2- or 3-furyl, 2- or 3-thienyl, 4- or 5-imidazolyl, 2-, 4- or 5-thiazolyl, 2-, 4- or 5-thiazolidinyl, or 2-, 3- or 4-pyridyl, wherein each of the alkyl portions provided in the definition of $R_6$ that is not of a specifically defined carbon length contains 1 to 4 carbon atoms; or $R_5$ represents a hydrogen atom or a straight or branched alkyl group containing 1 to 6 carbon atoms, and $R_6$ represents a hydroxyl group, an amino group or an alkyloxy group containing 1 to 6 straight- or branched-chain carbon atoms optionally substituted by a phenyl group, or a $PO(OR_7)_2$ group, in which $R_7$ represents a hydrogen atom or a straight or branched alkyl group containing 1 to 6 carbon atoms, or an aromatic heterocycle, or R represents an —NH—CO—T group in which T represents a hydrogen atom or a straight or branched alkyl group containing 1 to 6 carbon atoms optionally substituted by one or more amino, carboxyl, alkyloxycarbonyl, hydroxyl, alkyloxy, mercapto or alkylthio groups, wherein each of the alkyl portions provided in the definition of T contains 1 to 4 carbon atoms;

$R_1$ and $R_2$, which are identical or different, are selected from a hydrogen atom, a halogen atom, a hydroxyl group, an alkyl group, a straight or branched chain alkyloxy or aralkyloxy group optionally substituted by a dialkylamino group wherein the two alkyl portions of said dialkylamino group may form, together with the nitrogen atom to which they are attached, a saturated heterocycle containing 5 or 6 ring carbon atoms, an alkylthio group, and an alkyloxycarbonyl group; or $R_1$ and $R_2$, situated at the ortho position with respect to one another, together with the ring carbon atoms to which they are attached form a saturated or unsaturated heterocycle containing 1 or 2 heteroatoms selected from nitrogen and oxygen, optionally substituted by a halogen atom or by an alkyl or alkyloxy group; or $R_1$ represents a hydrogen atom, a halogen atom, an alkyl group, an alkyloxy group optionally substituted by a dialkylamino group, an alkylthio group, or an alkyloxycarbonyl group, and $R_2$ represents a thioalkyl group, wherein, in this case, the compound of formula (I) exists in the form of a dimer compound wherein the two parts of the dimer are connected via a disulphide bridge formed from the two thioalkyl $R_2$ groups, and further wherein each of the alkyl portions and groups provided in the definition of $R_1$ and $R_2$ contains 1 to 4 carbon atoms;

$R_3$ represents a hydrogen atom, a halogen atom, an alkyl group, an acyl group, an alkenyl group containing 2 to 4 carbon atoms, an alkyloxy group, or an alkylthio group, wherein each of the alkyl portions and groups provided in the definition of $R_3$ contains 1 to 4 carbon atoms;

X represents an oxygen or sulphur atom, or an —NH—, —CO—, optionally substituted methylene, ethylene, alkylidene, or 1,1-cycloalkyl group containing 3 to 6 carbon atoms; and Y represents an oxygen or sulphur atom; or a pharmaceutically acceptable salt thereof.

2. A compound of formula (I) or a pharmaceutically acceptable salt thereof according to claim 1, wherein one of $R_1$ and $R_2$ represents a hydrogen atom and the other represents an alkyloxy group containing from 1 to 4 carbon atoms; $R_3$ represents a hydrogen atom; X represents a methylene group; Y represents an oxygen atom; and R represents a group of formula —$(CH_2)_m$—$X_1$—$(CH_2)_n$—Z in which m is equal to 0 or 1, $X_1$ represents a bond, n is equal to 0, and Z represents a carboxyl group, a —$COOR_4$ group in which $R_4$ represents an alkyl group containing 1 to 3 carbon atoms, or a $CON(R_5)(R_6)$ group in which $R_5$ and $R_6$ are defined according to claim 1.

3. The dextrorotatory enantiomer of (3aS,4R,9R,9aS)-4,9-ethano-2-[2-(2-methoxyphenyl)prop-2-en-1-oyl]-9-phenyl-1,2,3,3a,9,9a-hexahydro-1H-benzo[f]isoindole-3a-carboxylic acid, a pharmaceutically acceptable salt thereof or an ester thereof containing 1 to 3 carbon atoms.

4. The t-butyl ester of N-[(3aS,4R,9R,9aS)-4,9-ethano-2-[2-(2-methoxyphenyl)prop-2-en-1-oyl]-9-phenyl-2,3,3a,4,9,9a-hexahydro-1H-benzo[f]isoindol-3a-ylcarbonyl]-(S)-phenylglycine.

5. A process for preparing a compound of formula (I) or a pharmaceutically acceptable salt thereof according to claim 1, in which R, $R_1$, $R_2$ and $R_3$ are defined according to claim 1, Y represents an oxygen or sulphur atom, and X represents a —CO—, methylene, ethylene, alkylidene or 1,1-cycloalkyl group containing 3 to 6 carbon atoms, said process comprising reacting an acid of formula (II):

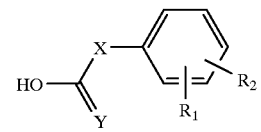

(II)

in which $R_1$, $R_2$ and X are defined as above and Y represents an oxygen or sulphur atom, or reacting the methyl ester of said acid of formula (II) or another derivative of said acid of formula (II), with a compound of formula (III):

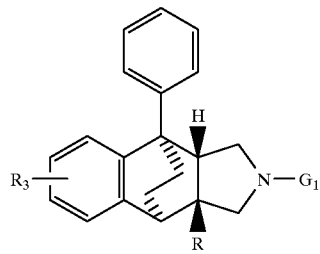

(III)

in which R and $R_3$ are defined as above and $G_1$ represents a hydrogen atom, under conditions sufficient to obtain said compound of formula (I) or salt thereof, and optionally, when R represents or contains a —$COOR_4$ group in which $R_4$ represents an alkyl group, saponifying the product obtained from said reaction under conditions sufficient to obtain said compound of formula (I) or salt thereof in which R represents or contains a carboxyl group, and optionally, when R represents or contains a —$PO(OR_7)_2$ group in which $R_7$ represents an alkyl group, converting the product obtained from said reaction by means of a nucleophilic agent, under conditions sufficient to obtain said compound of formula (I) or salt thereof in which R represents or contains a —$PO_3H_2$ group.

6. A process for preparing a compound of formula (I) or a pharmaceutically acceptable salt thereof according to claim 1, in which Y represents an oxygen or sulphur atom and X represents an oxygen atom, said process comprising reacting a haloformate or halothioformate of formula (IV):

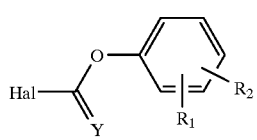

in which Y represents an oxygen or sulphur atom, $R_1$ and $R_2$ are defined according to claim 1 and Hal represents a halogen atom, with a compound of formula (III):

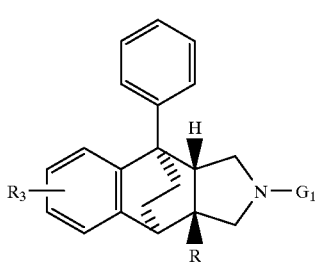

in which R and $R_3$ are defined according to claim 1 and $G_1$ represents a hydrogen atom under conditions sufficient to obtain said compound of formula (I) or salt thereof, and optionally, when R represents or contains a —$COOR_4$ group in which $R_4$ represents an alkyl group, saponifying the product obtained from said reaction under conditions sufficient to obtain said compound of formula (I) or salt thereof in which R represents or contains a carboxyl group, and optionally, when R represents or contains a —$PO(OR_7)_2$ group in which $R_7$ represents an alkyl group, converting the product obtained from said reaction by means of a nucleophilic agent, under conditions sufficient to obtain said compound of formula (I) or salt thereof in which R represents or contains a —$PO_3H_2$ group.

7. A process for preparing a compound of formula (I) or a pharmaceutically acceptable salt thereof according to claim 1, in which Y represents an oxygen or sulphur atom and X represents an NH group, said process comprising reacting an isocyanate or an isothiocyanate of formula (V):

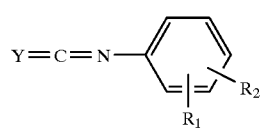

in which Y represents an oxygen or sulphur atom, and $R_1$ and $R_2$ are defined according to claim 1, with a compound of formula (III):

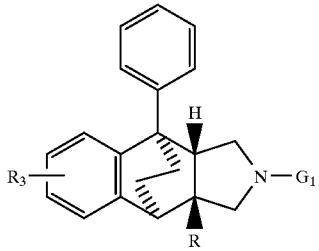

in which R and $R_3$ are defined according to claim 1 and $G_1$ represents a hydrogen atom, under conditions sufficient to obtain said of compound said formula (I) or salt thereof, and optionally, when R represents or contains a —$COOR_4$ group in which $R_4$ represents an alkyl group, saponifying the product obtained from said reaction under conditions sufficient to obtain said compound of formula (I) or salt thereof in which R represents or contains a carboxyl group, and optionally, when R represents or contains a —$PO(OR_7)_2$group in which $R_7$ represents an alkyl group, converting the product obtained from said reaction by means of a nucleophilic agent, under conditions sufficient to said compound of formula (I) or salt thereof in which R represents or contains a —$PO_3H_2$ group.

8. A process for preparing a compound of formula (I) or a pharmaceutically acceptable salt thereof according to claim 1, in which $R_1$, $R_2$ and $R_3$ are defined according to claim 1, X represents an oxygen or sulphur atom or an —NH—, —CO—, methylene, ethylene, alkylidene or 1,1-cycloalkyl group containing 3 to 6 carbon atoms, Y represents an oxygen or sulphur atom, and R represents a group of formula —$(CH_2)_m$—$X_1$—$(CH_2)_n$—Z in which $X_1$, m and n are defined according to claim 1, and Z represents a —$COOR_4$ group in which $R_4$ represents a straight or branched alkyl group containing 1 to 3 carbon atoms, said process comprising esterifying a compound of formula (I) or a salt thereof in which $R_1$, $R_2$, $R_3$, X, Y, $X_1$, m and n are defined as above and Z represents a carboxyl group, under conditions sufficient to obtain said compound of formula (I) or a salt thereof.

9. A process for preparing a compound of formula (I) or a pharmaceutically acceptable salt thereof according to claim 1, in which $R_1$, $R_2$ and $R_3$ are defined according to claim 1, X represents an oxygen or sulphur atom or an —NH—, —GO—, methylene, ethylene, alkylidene or 1,1-cycloalkyl group containing 3 to 6 carbon atoms, Y represents an oxygen or sulphur atom, and R represents a group of formula —$(CH_2)_m$—$X_1$—$(CH_2)_n$—Z in which $X_1$, m and n are defined according to claim 16, and Z represents a $CON(R_5)(R_6)$ group in which $R_5$ represents a hydrogen atom or a straight or branched alkyl group containing 1 to 6 carbon atoms and $R_6$ represents a hydrogen atom or a straight or branched alkyl group containing 1 to 6 carbon atoms optionally substituted by an amino, alkylamino, dialkylamino, alkyloxy, alkylthio, alkyloxycarbonyl, carboxyl, cyano, phenyl optionally substituted by one or more identical or different groups selected from alkyloxy and trifluoromethyl groups, 1- or 2-naphthyl, 2- or 3-furyl, 2- or 3-thienyl, 4- or 5-imidazolyl, 4- or 5-thiazolyl, 2-, 3-or 4-pyridyl, indanyl, and thiochromanyl groups, wherein the alkyl portions and groups in the definition of $R_6$ contain 1 to 4 carbon atoms, or $R_5$ represents a hydrogen atom or a straight or branched alkyl group containing 1 to 6 carbon atoms and $R_6$ represents a hydroxyl group, an amino group or an alkyloxy group containing 1 to 6 straight- or branched-chain carbon atoms optionally substituted by a phenyl group, said process comprising reacting a compound of formula $HN(R_5)(R_6)$, in which $R_5$ and $R_6$ are defined as above, with a compound of formula (I) in which $R_1$, $R_2$, $R_3$, X, Y, $X_1$, m and n are defined as above and Z represents a carboxyl group, under conditions sufficient to obtain said compound of formula (I) or a salt thereof.

10. A process for preparing a compound of formula (I) or a pharmaceutically acceptable salt thereof according to claim 1, in which $R_1$, $R_2$ and $R_3$ are defined according to claim 1, X represents an oxygen or sulphur atom or an —NH—, —CO—, methylene, ethylene, alkylidene or 1,1-cycloalkyl group containing 3 to 6 carbon atoms, Y represents an oxygen or sulphur atom, and R represents a group of formula —NHCO—T in which T represents a hydrogen atom or an alkyl group containing 1 to 6 carbon atoms optionally substituted by an amino, carboxyl, alkyloxycarbonyl, hydroxyl, alkyloxy, mercapto or alkylthio group, wherein the alkyl portions provided in the definition of T contain 1 to 4 carbon atoms, said process comprising reacting an acid of formula T—CO—OH, in which T is defined as above, with a compound of formula (VI):

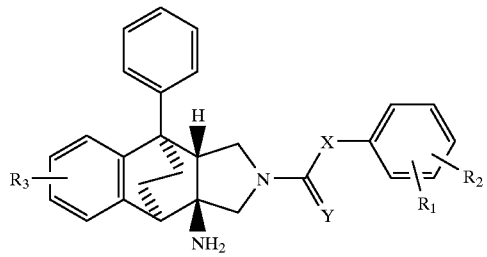
(VI)

in which $R_1$, $R_2$, $R_3$, X and Y are defined as above, and optionally, replacing any protected ester functional group or protected amine functional group carried by T with a carboxyl or amino group, respectively, under conditions sufficient to obtain said compound of formula (I) or a salt thereof.

11. A process for preparing a compound of formula (I) according to claim 1, in which R represents a group of formula

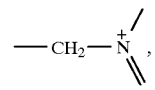, said process comprising reacting an excess of a tertiary amine and of a strong acid or of a derivative of a strong acid with a compound of formula (VII):

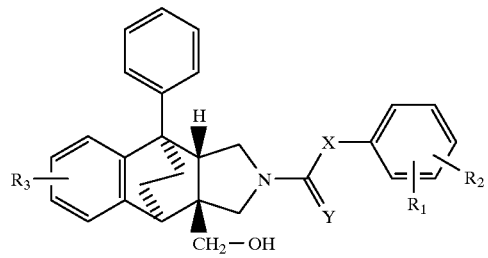
(VII)

in which $R_1$, $R_2$, $R_3$, X and Y are defined according to claim 1, under conditions sufficient to obtain said compound of formula (I) or a salt thereof.

12. A process for preparing a compound of formula (I) or a pharmaceutically acceptable salt thereof according to claim 1 in which Y represents a sulphur atom, said process comprising thionating a compound according to claim 1 in which Y represents an oxygen atom, under conditions sufficient to obtain said compound of formula (I) or a salt thereof.

13. A pharmaceutical composition, said composition comprising a pharmaceutically effective amount of at least one compound of formula (I) or pharmaceutically acceptable salt thereof according to claim 1, in combination with at least one pharmaceutically acceptable carrier.

14. A compound of formula (I) or a pharmaceutically acceptable salt thereof according to claim 1, wherein said compound or salt is in the racemic form or in the nonracemic form as one or more of its isomers.

15. A compound of formula (I) according to claim 1, wherein R represents a

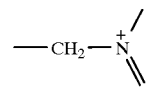

group.

16. A compound of formula (I) according to claim 15, wherein in said

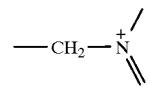

group, the

portion represents a pyridinium group.

17. A compound of formula (I) according to claim 1, wherein X represents vinylidene.

18. A process according to claim 5, wherein said another derivative of said acid of formula (II) is a halide or an anhydride.

19. A pharmaceutical composition according to claim 13, wherein said pharmaceutically acceptable carrier is inert.

20. The compound (3aS,4R,9R,9aS)-N-(3,4-dimethoxybenzyl)-4,9-ethano-2-[2-(2-methoxyphenyl)

prop-2-en-1-oyl]-9-phenyl-2,3,3a,4,9,9a-hexahydro-1H-benzo(f)isoindole-3a-carboxamide or a pharmaceutically acceptable salt thereof.

21. The compound (3aS,4R,9R,9aS)-N-[(2-pyridyl)-methyl]-4,9-ethano-2-[2-(2-methoxyphenyl)prop-2-en-1-oyl]-9-phenyl-2,3,3a,4,9,9a-hexahydro-1H-benzo(f)isoindole-3a-carboxamide or a pharmaceutically acceptable salt thereof.

22. N-[(S)-t-butyl-phenylglycinoyl)]-(3aS,4R,9R,9aS)-4,9-ethano-2-[(2-methoxyphenyl)prop-2-en-1-oyl]-9-phenyl-2,3,3a,4,9,9a-hexahydro-1H-benzo[f]isoindole-3a-carboxamide or a pharmaceutically acceptable salt thereof.

23. (3aS,4R,9R,9aS)-N-[(3-pyridyl)methyl]-4,9-ethano-2-[(-methoxyphenyl)prop-2-en-1-oyl]-9-phenyl- 2,3,3a,4,9,9a-hexahydro-1H-benzo[f]isoindole-3a-carboxamide or a pharmaceutically acceptable salt thereof.

24. A method for treating a cancer or a leukaemia, said method comprising administering to a host for the purpose of effecting said treatment an effective amount of a compound of formula (I) according to claim 1 or a salt thereof.

25. A compound of formula (I):

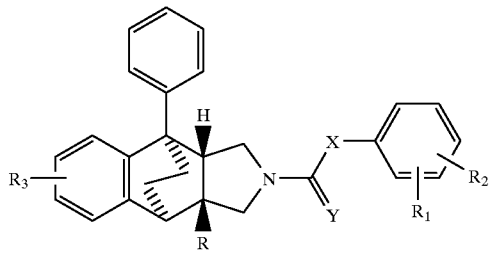

(I)

in which:
R represents:
  a group of formula —(CH$_2$)$_m$—X$_1$—(CH$_2$)$_n$—Z in which
    X$_1$ represents a single bond or a sulphur atom,
    m represents an integer equal to 0 or 1, and
    n represents an integer equal to 0, 1 or 2;
  wherein one or more methylene groups in said R group may be substituted by at least one alkoxycarbonyl group containing 1 to 4 carbon atoms; and
  Z represents
    a carboxyl group, or
    a COOR$_4$ group, in which R$_4$ represents a straight or branched alkyl group containing 1 to 2 carbon atoms, or
    a CON(R$_5$)(R$_6$) group, in which R$_5$ represents a hydrogen atom or a straight or branched alkyl group containing 1 to 6 carbon atoms, and R$_6$ represents a hydrogen atom, an indanyl or thiochromanyl group, or a straight or branched alkyl group containing 1 to 6 carbon atoms optionally substituted by one or more amino, alkylamino, dialkylamino, hydroxyl, alkyloxy, mercapto, alkylthio, aralkylthio, alkyloxycarbonyl, carboxyl, cyano, phenyl optionally substituted by one or more identical or different groups selected from halogen atoms and alkyl, alkyloxy, and trifluoromethyl groups, or a 1- or 2-naphthyl, 2- or 3-furyl, 2- or 3-thienyl, 4- or 5-imidazolyl, 2-, 4- or 5-thiazolyl, 2-, 3- or 4-pyridyl group, wherein each of the alkyl portions provided in the definition of R$_6$ that is not of a specifically defined carbon length contains 1 to 4 carbon atoms; or R$_5$ represents a hydrogen atom or a straight or branched alkyl group containing 1 to 6 carbon atoms, and R$_6$ represents a hydroxyl group, an amino group or an alkyloxy group containing 1 to 6 straight- or branched-chain carbon atoms optionally substituted by a phenyl group, or
    a PO(OR$_7$)$_2$ group, in which R$_7$ represents a hydrogen atom or a straight or branched alkyl group containing 1 to 2 carbon atoms, or
    an aromatic heterocycle,
  or R represents an —NH—CO—T group in which T represents a hydrogen atom or a straight or branched alkyl group containing 1 to 3 carbon atoms optionally substituted by one or more amino, carboxyl, alkyloxycarbonyl, or alkylthio groups, wherein each of the alkyl portions provided in the definition of T that is not of a specifically defined carbon length contains 1 to 4 carbon atoms;

R$_1$ and R$_2$, which are identical or different, are selected from a hydrogen atom, a halogen atom, a hydroxyl group, an alkyl group, a straight or branched chain alkyloxy or aralkyloxy group, optionally substituted by a dialkylamino group wherein the two alkyl portions of said dialkylamino group may form, together with the nitrogen atom to which they are attached, a saturated heterocycle containing 5 or 6 ring carbon atoms, an alkylthio group, and an alkyloxycarbonyl group; or R$_1$ and R$_2$, situated at the ortho position with respect to one another, together with the ring carbon atoms to which they are attached form a saturated or unsaturated heterocycle containing 1 or 2 heteroatoms selected from nitrogen and oxygen, optionally substituted by a halogen atom; or R$_1$ represents a hydrogen atom, a halogen atom, an alkyl group, an alkyloxy group optionally substituted by a dialkylamino group, an alkylthio group, or an alkyloxycarbonyl group, and R$_2$ represents a thioalkyl group, wherein, in this case, the compound of formula (I) exists in the form of a dimer compound wherein the two parts of the dimer are connected via a disulphide bridge formed from the two thioalkyl R$_2$ groups, and further wherein each of the alkyl portions and groups provided in the definition of R$_1$ and R$_2$ contains 1 to 4 carbon atoms;

R$_3$ represents a hydrogen atom, a halogen atom, an acyl group, an alkenyl group containing 2 to 4 carbon atoms, or an alkyloxy group, wherein each of the alkyl portions provided in the definition of R$_3$ that is not of a specifically defined carbon length contains 1 to 4 carbon atoms;

X represents an oxygen, or an —NH—, —CO—, an optionally substituted methylene, ethylene, alkylidene, or 1,1-cycloalkyl group containing 3 to 6 carbon atoms; and Y represents an oxygen or sulphur atom; or a pharmaceutically acceptable salt thereof.

26. A compound of formula (I):

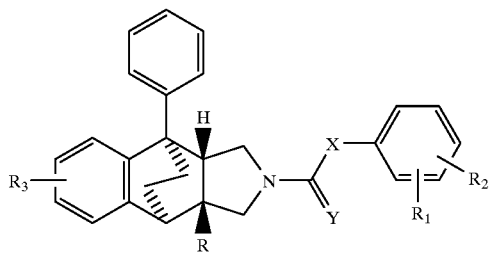

in which:

R represents:
a group of formula —(CH$_2$)$_m$—X$_1$—(CH$_2$)$_n$—Z in which
X$_1$ represents a single bond,
m represents an integer equal to 0, and
n represents an integer equal to 0; and
Z represents
a carboxyl group, or
a COOR$_4$ group, in which R$_4$ represents an alkyl group containing 1 carbon atom, or
a CON(R$_5$)(R$_6$) group, in which R$_5$ represents a hydrogen atom or a straight or branched alkyl group containing 1 to 6 carbon atoms, and R$_6$ represents a hydrogen atom, an indanyl group, or a straight or branched alkyl group containing 1 to 6 carbon optionally substituted by one or more alkyloxy, mercapto, alkylthio, aralkylthio, carboxyl, cyano, phenyl optionally substituted by one or more identical or different groups selected from alkyl, alkyloxy, and trifluoromethyl groups, or a 2- or 3-furyl, 2- or 3-thienyl, 4- or 5-imidazolyl, 2-, 4- or 5-thiazolyl, or a 2-, 3- or 4-pyridyl group, wherein each of the alkyl portions provided in the definition of R$_6$ that is not of a specifically defined carbon length contains 1 to 4 carbon atoms; or R$_5$ represents a hydrogen atom or a straight or branched alkyl group containing 1 to 6 carbon atoms, and R$_6$ represents an alkyloxy group containing 1 to 6 straight- or branched-chain carbon atoms optionally substituted by a phenyl group;

R$_1$ and R$_2$, which are identical or different, are selected from a hydrogen atom, a straight or branched chain alkyloxy or aralkyloxy group optionally substituted by a dialkylamino group wherein the two alkyl portions of said dialkylamino group may form, together with the nitrogen atom to which they are attached, a saturated heterocycle containing 5 or 6 ring carbon atoms, and an alkylthio group, and further wherein each of the alkyl portions and groups provided in the definition of R$_1$ and R$_2$ contains 1 to 4 carbon atoms;

R$_3$ represents a hydrogen atom, or a halogen atom, or an aralkyloxy group, wherein each of the alkyl portions and groups provided in the definition of R$_3$ contains 1 to 4 carbon atoms;

X represents an optionally substituted methylene or vinylidene group; and

Y represents an oxygen or sulphur atom; or a pharmaceutically acceptable salt thereof.

27. A compound of formula (I):

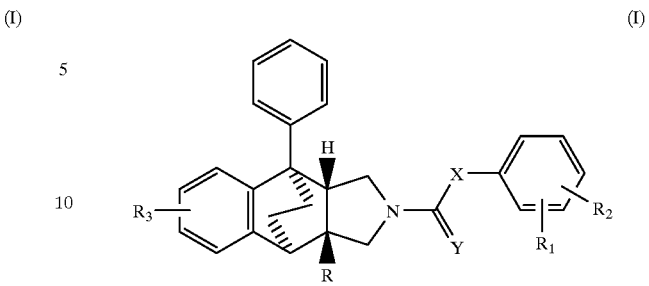

in which:

R represents:
a group of formula —(CH$_2$)$_m$—X$_1$—(CH$_2$)$_n$—Z in which
X$_1$ represents a single bond,
m represents an integer equal to 0, and
n represents an integer equal to 0; and
Z represents
a carboxyl group, or
a COOR$_4$ group, in which R$_4$ represents a straight or branched alkyl group containing 1 carbon atom, or
a CON(R$_5$)(R$_6$) group, in which R$_5$ represents a hydrogen atom or a straight or branched alkyl group containing 1 to 6 carbon atoms, and R$_6$ represents a hydrogen atom, an indanyl group, or a straight or branched alkyl group containing 1 to 6 carbon atoms optionally substituted by one or more, alkyloxy, aralkylthio, alkyloxycarbonyl, carboxyl, cyano, phenyl optionally substituted by one or more identical or different groups selected from alkyl, and alkyloxy groups, or a 2- or 3-furyl, 2- or 3-thienyl, 4- or 5-imidazolyl, 2-, 4- or 5-thiazolyl, or 2-, 3- or 4-pyridyl group, wherein each of the alkyl portions provided in the definition of R$_6$ that is not of a specifically defined carbon length contains 1 to 4 carbon atoms; or R$_6$ represents a hydrogen atom or a straight or branched alkyl group containing 1 to 6 carbon atoms, and R$_6$ represents a hydroxyl group, an amino group or an alkyloxy group containing 1 to 6 straight- or branched-chain carbon atoms optionally substituted by a phenyl group;

R$_1$ and R$_2$, which are identical or different, are selected from a hydrogen atom, and a straight or branched chain alkyloxy group optionally substituted by a dialkylamino group wherein the two alkyl portions of said dialkylamino group may form, together with the nitrogen atom to which they are attached, a saturated heterocycle containing 5 or 6 ring carbon atoms, wherein each of the alkyl portions provided in the definition of R$_1$ and R$_2$ contains 1 to 4 carbon atoms;

R$_3$ represents a hydrogen atom;

X represents an optionally substituted methylene or vinylidene; and

Y represents an oxygen or sulphur atom; or a pharmaceutically acceptable salt thereof.

* * * * *

UNITED STATES PATENT AND TRADEMARK OFFICE
CERTIFICATE OF CORRECTION

PATENT NO. : 5,936,097
DATED : August 10, 1999
INVENTOR(S) : Alain Commercon, et. al.

It is certified that error appears in the above-identified patent and that said Letters Patent is hereby corrected as shown below:

Claim 7, column 78, line 16, "of compound" should read --compound of--.
Claim 9, column 78, line 48, "-GO-" should read -- -CO- --.
Claim 23, column 81, line 14, "2-[(-methoxyphenyl)" should read --2-[(2-methoxyphenyl)--.
Claim 26, column 83, line 46, "l to 6" should read --1 to 6--.
Claim 27, column 84, line 44, "$R_6$ represents" should read --$R_5$ represents--.

Signed and Sealed this

Fifth Day of December, 2000

Attest:

Q. TODD DICKINSON

Attesting Officer

Director of Patents and Trademarks